(12) United States Patent
Wong et al.

(10) Patent No.: US 10,274,488 B2
(45) Date of Patent: Apr. 30, 2019

(54) GLYCAN ARRAYS ON PTFE-LIKE ALUMINUM COATED GLASS SLIDES AND RELATED METHODS

(71) Applicant: Academia Sinica, Taipei (TW)

(72) Inventors: Chi-Huey Wong, La Jolla, CA (US); Chung-Yi Wu, Taipei (TW); Susan Y. Tseng, Taipei (TW)

(73) Assignee: ACADEMIA SINICA, Taipei (TW)

( * ) Notice: Subject to any disclaimer, the term of this patent is extended or adjusted under 35 U.S.C. 154(b) by 283 days.

(21) Appl. No.: 14/182,290

(22) Filed: Feb. 18, 2014

(65) Prior Publication Data

US 2017/0038378 A1    Feb. 9, 2017

Related U.S. Application Data

(62) Division of application No. 12/503,797, filed on Jul. 15, 2009, now Pat. No. 8,680,020.

(60) Provisional application No. 61/107,624, filed on Oct. 22, 2008, provisional application No. 61/080,931, filed on Jul. 15, 2008.

(51) Int. Cl.
| | |
|---|---|
| C40B 50/00 | (2006.01) |
| C40B 50/12 | (2006.01) |
| G01N 33/553 | (2006.01) |
| C40B 40/12 | (2006.01) |
| C40B 50/14 | (2006.01) |
| G01N 33/58 | (2006.01) |
| C40B 60/00 | (2006.01) |
| H01J 49/40 | (2006.01) |

(52) U.S. Cl.
CPC .......... *G01N 33/553* (2013.01); *C40B 40/12* (2013.01); *C40B 50/14* (2013.01); *G01N 33/582* (2013.01); *G01N 2333/942* (2013.01); *G01N 2400/10* (2013.01); *H01J 49/40* (2013.01)

(58) Field of Classification Search
CPC .............................. G01N 33/553; G01N 33/58
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |

(Continued)

FOREIGN PATENT DOCUMENTS

| | | |
|---|---|---|
| EP | 404097 A2 | 12/1990 |
| EP | 0341735 B1 | 9/1992 |

(Continued)

OTHER PUBLICATIONS

Hsu et al., Desorption Ionization of Biomolecules on Metals, Analytical Chemistry, 2008, 80(13), 5203-5210. (Year: 2008).*

(Continued)

*Primary Examiner* — Amy M Bunker
(74) *Attorney, Agent, or Firm* — Duane Morris LLP

(57) ABSTRACT

Aluminum coated glass slides provide a novel glycan array platform. Specifically, aluminum coated glass slides increase sensitivity of fluorescent based assay methods. Additionally, aluminum coated glass slides allows for mass spectroscopic analysis of carbohydrates and provide a platform for examining activity of cellulases. The unique properties of ACG slides include: 1) the metal oxide layer on the surface can be activated for grafting organic compounds such as modified oligosaccharides; 2) the surface remains electrically conductive, and the grafted oligosaccharides can be simultaneously characterized by mass spectrometry and carbohydrate-binding assay; and 3) the slides are more sensitive than transparent glass slides in binding analysis.

8 Claims, 33 Drawing Sheets

Specification includes a Sequence Listing.

(56) References Cited

U.S. PATENT DOCUMENTS

| | | |
|---|---|---|
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 * | 2/2006 | Dukler ............... C07H 15/02 435/6.14 |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,759,726 B2 | 9/2017 | Wong et al. |
| 9,803,177 B2 | 10/2017 | Rossi et al. |
| 9,914,956 B2 | 3/2018 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |

(56) References Cited

U.S. PATENT DOCUMENTS

| | | |
|---|---|---|
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1* | 5/2004 | Wohlstadter .......... B01L 3/5027 422/52 |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1* | 10/2005 | Seeberger .......... C07H 3/06 435/6.16 |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1* | 9/2007 | Wong .......... A61K 31/716 514/23 |
| 2007/0213297 A1 | 9/2007 | Wong |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0145838 A1 | 6/2008 | Suda et al. |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Powers |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| JP | 2002-371087 A | 12/2002 |
| JP | 2008-025989 A | 2/2008 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |

(56) References Cited

FOREIGN PATENT DOCUMENTS

| WO | WO 03/077945 A1 | 9/2003 |
|---|---|---|
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO2010/029302 A2 | 3/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/106937 A1 | 7/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/031762 A1 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |

OTHER PUBLICATIONS

Moal et al., Enhanced Fluorescence Cell Imagine with Metal-Coated Slides, Biophysical Journal, 2007, 92(6), 2150-2161. (Year: 2007).*
Abrahmsén et al, "Analysis of signals for secretion in the staphylococcal protein A gene," *EMBO J.*, Dec. 30, 1985, 4(13B):3901-3906.
Altschul SF et al., "Basic local alignment search tool", *J Mol Biol.* Oct. 5, 1990;215(3):403-10.
Altschul SF, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli*," *Mol. Microbiol.*, Jan. 2001, 39(1):199-210.
Bachmann, *Cellular and Molecular Biology*, vol. 2. Chapter 72: Derivations and Genotypes of Some Mutant Derivatives of *Escherichia coli* K-12, Neidhardt et al., eds., 1987, pp. 1190-1219, American Society for Microbiology, Washington, D.C.
Baldwin et al., "Monoclonal antibodies in cancer treatment," *Lancet*, Mar. 15, 1986, 327(8481):603-605.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Barnes et al., "Methods for growth of cultured cells in serum-free medium," *Anal. Biochem.*, Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Bass et al., "Hormone phage: an enrichment method for variant proteins with altered binding properties," *Proteins*, 1990, 8(4):309-314.
Beck A., "Biosimilar, biobetter and next generation therapeutic antibodies" *MAbs.* Mar.-Apr. 2011;3(2):107-10. Epub Mar. 1, 2011.
Berra et al., "Correlation between ganglioside distribution and histological grading of human astrocytomas," *Int. J. Cancer*, Sep. 15, 1985, 36(3):363-366.
Birklé et al., "Role of tumor-associated gangliosides in cancer progression," *Biochimie*, Mar.-Apr. 2003, 85(3-4):455-463.
Bobo et al., "Convection-enhanced delivery of macromolecules in the brain," *Proc. Natl. Acad. Sci. U.S.A.*, Mar. 15, 1994, 91(6) 2076-2080.
Boerner et al., "Production of antigen-specific human monoclonal antibodies from in vitro-primed human splenocytes," *J. Immunol.*, Jul. 1, 1991, 147(1):86-95.
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Brennan et al., "Preparation of bispecific antibodies by chemical recombination of monoclonal immunoglobulin $G_1$ fragments," *Science*, Jul. 5, 1985, 229(4708):81-83.
Brimble et al., "The cell surface glycosphingolipids SSEA-3 and SSEA-4 are not essential for human ESC pluripotency," *Stem Cells*, Jan. 2007, 25(1):54-62.
Brodeur et al. *Monoclonal Antibody Production Techniques and Applications*, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," *Year in Immunol.*, 1993, 7:33-40.
Capel PJ et al., "Heterogeneity of human IgG Fc receptors" *Immunomethods.* Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.

(56) References Cited

OTHER PUBLICATIONS

Chen et al., "Chaperone activity of DsbC," *J. Bio. Chem.*, Jul. 9, 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Chiari, M. et al., "Advanced polymers for molecular recognition and sensing at the interface", *J Chromatography B*, Apr. 15, 2008, 866(1-2):89-103.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res.* 1989;52:81-149.
Clynes R, et al., "Fc receptors are required in passive and active immunity to melanoma" *Proc Natl Acad Sci U S A.* Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGκ monoclonal antibodies from a novel strain of minilocus transgenic mice," *Nature Biotechnol.*, Jul. 1996, 14(7):845-851.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Galfrè et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2):163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice* 2nd ed., Chapter 3: Production of Monoclonal Antibodies, 1986, pp. 59-103, Academic Press, London.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gottschling et al., "Stage-specific embryonic antigen-4 is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Hakomori et al., "Glycosphingolipid antigens and cancer therapy," *Chem. Biol.*, Feb. 1997,4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hata, K. et al., "Limited Inhibitory Effects of Oseltamivir and Zanamivir on Human Sialidases," Antimicrobial Agents and Chemotherapy, vol. 52, No. 10, Oct. 2008, in 8 pages.
Hawkins et al., "Selection of phage antibodies by binding affinity. Mimicking affinity maturation," *J. Mol. Biol.*, 1992, 226(3):889-896.
Heyman, "Complement and Fc-receptors in regulation of the antibody response," *Immunol. Lett.*, Dec. 1996, 54(2-3):195-199.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.

(56) References Cited

OTHER PUBLICATIONS

Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jenkins N, Curling EM., "Glycosylation of recombinant proteins: problems and prospects", *Enzyme Microb Technol.* May 1994;16(5):354-64.
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells,"*EMBO J.*, 1983, 2(12):2355-2361.
Karlin S. et al., "Methods for assessing the statistical significance of molecular sequence features by using general scoring schemes", *Proc Natl Acad Sci U S A*. Mar. 1990;87(6):2264-8.
Kato et al., "GMab-1, a high-affinity anti-3'-isoLM1/3'6'-isoLD1 IgG monoclonal antibody, raised in lacto-series ganglioside-defective knockout mice,"*Biochem. Biophys. Res. Commun.*, Jan. 1, 2010, 391(1):750-755.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Kudo et al., "Up-regulation of a set of glycosyltransferase genes in human colorectal cancer," *Lab. Invest.*, Jul. 1998, 78(7):797-811.
Lau et al., "N-Glycans in cancer progression," *Glycobiology*, Oct. 2008, 18(10):750-760.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood.* May 15, 2007;109(10):4336-42. Epub Jan. 23, 2007.
Liu et al., "Eradication of large colon tumor xenografts by targeted delivery of maytansinoids," *Proc. Natl., Acad. Sci. U.S.A.*, Aug. 6, 1996, 93(16):8618-8623.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I_1$, effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Louis et al., "The 2007 WHO classification of tumours of the central nervous system," *Acta. Neuropathol.*, Aug. 2007, 114(2):97-109.
Lu et al, "Single chain anti-c-Met antibody conjugated nanoparticles for in vivo tumor-targeted imaging and drug delivery," *Biomaterials*, Apr. 2011, 32(12):3265-3274.
MacFarlane GT, et al., "Formation of glycoprotein degrading enzymes by Bacteroides fragilis" *FEMS Microbiol Lett.* Jan. 15, 1991;61(2-3):289-93.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.

(56) References Cited

OTHER PUBLICATIONS

Marks et al., "By-passing immunization. Human antibodies from V-gene libraries displayed on phage," *J. Mol. Biol.*, Dec. 5, 1991, 222(3):581-597.

Marks et al., "By-passing immunization. Building high affinity human antibodies by chain shuffling," *Nature Biotechnology*, Jul. 1992, 10(7):779-783.

Mather et al., "Culture of testicular cells in hormone-supplemented serum-free medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17):1850.

Mimura et al., "Role of oligosaccharide residues of IgG1-Fc in FcγRIIb binding," *J. Biol. Chem.*, Dec. 7, 2001, 276(49):45539-45547.

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.

Morelle, W. et al., "The Mass Spectrometric Analysis of Glycoproteins and their Glycan Sturctures", *Review in Current Analytical Chemistry*, vol. 1, No. 1 (2005), pp. 29-57.

Mori K, et al., "Non-fucosylated therapeutic antibodies: the next generation of therapeutic antibodies" *Cytotechnology.* Dec. 2007;55(2-3):109-14. Epub Oct. 31, 2007.

Morimoto et al., "Single-step purification of F(ab')₂ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.

Morrison et al., "Chimeric human antibody molecules: mouse antigen-binding domains with human constant region domains," *Proc. Natl. Acad. Sci. U.S.A.*, Nov. 1984, 81(21):6851-6855.

Morrison, "Immunology. Success in specification," *Nature*, Apr. 28, 1994, 368(6474):812-813.

Munson et al., "Ligand: a versatile computerized approach for characterization of ligand-binding systems," *Anal. Biochem.*, Sep. 1, 1980, 107(1):220-239.

Neuberger et al., "Recombinant antibodies possessing novel effector functions," *Nature*, Dec. 13-19, 1984, 312(5995):604-608.

Neuberger, "Generating high-avidity human Mabs in mice," *Nature Biotechnol.*, Jul. 1996, 14(7):826.

Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.

Niculescu-Duvaz et al., "Antibody-directed enzyme prodrug therapy (ADEPT): A review," *Adv. Drg. Del. Rev.*, Jul. 7, 1997, 26(2-3):151-172.

Noto et al., "CD44 and SSEA-4 positive cells in an oral cancer cell line HSC-4 possess cancer stem-like cell characteristics," *Oral Oncol.*, Aug. 2013, 49(8):787-795.

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.

Pearlman et al. *Peptide and Protein Drug Delivery*, Chapter 6: Analysis of Protein Drugs, Lee, ed., 1991, pp. 247-301, Marcel Dekker Publishing, New York.

Peipp et al., "Antibody fucosylation differentially impacts cytotoxicity mediated by NK and PMN effector cells," *Blood*, 2008, 112(6):2390-2399.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology*, vol. 113: The Pharacology of Monoclonal Antibodies, Chapter 11: Antibodies from *Escherichia coli*, Rosenberg et al., eds., 1994, pp. 269-315, Springer-Verlag, Berlin.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.

Presta, "Antibody engineering," *Curr. Opin. Struct. Biol.*, Aug. 1992, 2(4):593-596.

Proba et al., "Functional antibody single-chain fragments from the cytoplasm of *Escherichia coli*: influence of thioredoxin reductase (TrxB)," *Gene*, Jul. 4, 1995, 159(2):203-207.

Puigbò P, Guzmán E, Romeu A, Garcia-Vallvé S. OPTIMIZER: a web server for optimizing the codon usage of DNA sequences. *Nucleic Acids Res.* Jul. 2007;35(Web Server Issue):W126-31. Epub Apr. 16, 2007.

Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.

Ravetch et al., "Divergent roles for Fc receptors and complement in vivo," *Ann. Rev. Immunol.*, 1998, 16:421-432.

Ravetch et al., "Fc receptors," *Annu. Rev. Immunol.*, 1991, 9:457-492.

Reyes et al., "Expression of human β-interferon cDNA under the control of a thymidine kinase promoter from herpes simplex virus," *Nature*, Jun. 17, 1982, 297(5867):598-601.

Riechmann et al., "Reshaping human antibodies for therapy," *Nature*, Mar. 24, 1988, 332(6162):323-327.

Roguska et al., "Humanization of murine monoclonal antibodies through variable domain resurfacing," *Proc. Natl. Acad. Sci. U.S.A.*, Feb. 1, 1994, 91(3):969-973.

Roos et al., "Specific inhibition of the classical complement pathway by C1q-binding peptides," *J. Immunol.*, Dec. 15, 2001, 167(12):7052-7059.

Rowland et al, "Drug localisation and growth inhibition studies of vindesine-monoclonal anti-CEA conjugates in a human tumour xenograft," *Cancer Immunol Immunother.*, 1986, 21(3):183-187.

Ruiz et al., "IMGT, the international ImMunoGeneTics database," *Nucl. Acids Res.*, Jan. 1, 2000, 28(1):219-221.

Saito et al., "Expression of globo-series gangliosides in human renal cell carcinoma," *Jpn. J. Cancer Res.*, Jul. 1997, 88(7):652-659.

Saito et al., "Human α2,3-sialyltransferase (ST3Gal II) is a stage-specific embryonic antigen-4 synthase," *J. Biol. Chem.*, Jul. 18, 2003, 278(29):26474-26479.

Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.

Schenkel-Brunner, *Human Blood Groups*, Chapter 8: P System, 1995, pp. 211-234, Springer-Verlag, Vienna.

(56) References Cited

OTHER PUBLICATIONS

Schier et al., "Identification of functional and structural amino-acid residues by parsimonious mutagenesis," *Gene*, Mar. 9, 1996, 169(2):147-155.

Sell, "Cancer-associated carbohydrates identified by monoclonal antibodies," *Hum. Pathol.*, Oct. 1990, 21(10):1003-1019.

Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.

Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.

Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.

Sidhu et al., "Phage-displayed antibody libraries of synthetic heavy chain complementarity determining regions," *J. Mol. Biol.*, Apr. 23, 2004, 338(2):299-310.

Siebenlist et al., "*E. coli* RNA polymerase interacts homologously with two different promoters," *Cell*, Jun. 1980, 20(2):269-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Skerra, "Bacterial expression of immunoglobulin fragments," *Curr. Opinion in Immunol.*, Apr. 1993, 5(2):256-262.

Slamon DJ, et al., "Human breast cancer: correlation of relapse and survival with amplification of the HER-2/neu oncogene" *Science*. Jan. 9, 1987; 235(4785):177-82.

Smith RA et al., "The active form of tumor necrosis factor is a trimer" *J Biol Chem*. May 25, 1987;262(15):6951-4.

Smyth MJ, et al., "CD4+CD25+ T regulatory cells suppress NK cell-mediated immunotherapy of cancer" *J Immunol*. Feb. 1, 2006;176(3):1582-7.

Suresh et al., "Bispecific monoclonal antibodies from hybrid hybridomas," *Methods in Enzymology*, 1986, 121:210-228.

Suzuki E, et al., "A nonfucosylated anti-HER2 antibody augments antibody-dependent cellular cytotoxicity in breast cancer patients" *Clin Cancer Res*. Mar. 15, 2007;13(6):1875-82.

Svennerholm et al., "Human brain gangliosides: Developmental changes from early fetal stage to advanced age," *Biochim. Biophys. Acta*, Sep. 25, 1989, 1005(2):109-117.

Syrigos et al., "Antibody directed enzyme prodrug therapy (ADEPT): a review of the experimental and clinical considerations," *Anticancer Research*, Jan.-Feb. 1999, 19(1A):605-614.

Takeda et al., "Construction of chimaeric processed immunoglobulin genes containing mouse variable and human constant region sequences," *Nature*, Apr. 4-10, 1985, 314(6010):452-454.

Taylor-Papadimitriou et al., "Exploiting altered glycosylation patterns in cancer: Progress and challenges in diagnosis and therapy," *Trends Biotechnol.*, Jun. 1994, 12(6):227-233.

Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.

Tomlinson et al., "The repertoire of human germline $V_H$ sequences reveals about fifty groups of $V_H$ segments with different hypervariable loops," *J. Mol. Biol.*, Oct. 5, 1992, 227(3):776-798.

Traunecker et al., "Bispecific single chain molecules (Janusins) target cytotoxic lymphocytes on HIV infected cells," *EMBO J.*, Dec. 1991, 10(12):3655-3659.

Traylor et al., "Gangliosides of human cerebral astrocytomas," *J. Neurochem.*, Jan. 1980, 34(1):126-131.

Tsai Ti, et al., "Effective sugar nucleotide regeneration for the large-scale enzymatic synthesis of Globo H and SSEA4" *J Am Chem Soc*. Oct. 2, 2013;135(39):14831-9, Epub Sep. 17, 2013.

Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.

Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.

Urlaub et al., "Isolation of Chinese hamster cell mutants deficient in dihydrofolate reductase activity." *Proc. Natl. Acad. Sci. U.S.A.*, Jul. 1980, 77(7):4216-4220.

Valentine Ma, et al., "Phosphorylation of the CD20 phosphoprotein in resting B lymphocytes. Regulation by protein kinase C" *J Biol Chem*. Jul. 5, 1989;264(19):11282-7.

Van Beek et al., "Increased sialic acid density in surface glycoprotein of transformed and malignant cells—a general phenomenon?" *Cancer Res.*, Nov. 1973, 33(11):2913-2922.

Van Meir et al., "Exciting new advances in neuro-oncology: the avenue to a cure for malignant glioma," *CA Cancer J. Clin.*, May-Jun. 2010, 60(3):166-193.

Van Slambrouck et al., "Clustering of monosialyl-Gb5 initiates downstream signalling events leading to invasion of MCF-7 breast cancer cells," *Biochem. J.*, Feb. 1, 2007, 401(3):689-699.

Vaswani et al., "Humanized antibodies as potential therapeutic drugs," *Ann. Allergy, Asthma Immunol.*, Aug. 1998, 81(2):105-116, 119.

Verhoeyen et al., "Reshaping human antibodies: grafting an antilysozyme activity," *Science*, Mar. 25, 1988, 239(4847):1534-1536.

Vermeer AW et al., "The thermal stability of immunoglobulin: unfolding and aggregation of a multi-domain protein" *Biophys J*. Jan. 2000;78(1):394-404.

Wang et al., "Glycan microarray of Globo H and related structures for quantitative analysis of breast cancer," *Proc. Natl. Acad. Sci. U.S.A.*, Aug. 19, 2008, 105(33):11661-11666.

Ward et al., "Binding activities of a repertoire of single immunoglobulin variable domains secreted from *Escherichia coli*," *Nature*, Oct. 12, 1989, 341(6242):544-546.

Waterhouse et al., "Combinatorial infection and in vivo recombination: a strategy for making large phage antibody repertoires," *Nuc. Acids Res.*, May 11, 1993, 21(9):2265-2266.

Wikstrand et al., "Monoclonal antibody therapy of human gliomas: Current status and future approaches," *Cancer Metastasis Rev.*, 1999, 18(4):451-464.

Williams et al., "Cloning and sequencing of human immunoglobulin V lambda gene segments." *Eur. J. Immunol.*, Jul. 1993, 23(7):1456-1461.

Winter et al., "Making antibodies by phage display technology," *Annu. Rev. Immunol.*, 1994, 12:433-455.

Woof et al., "Human antibody-Fc receptor interactions illuminated by crystal structures," *Nat. Rev. Immunol.*, Feb. 2004, 4(2):89-99.

Yansura et al., "Nucleotide sequence selection for increased expression of heterologous genes in *Escherichia coli*," *Methods: A Companion to Methods in Enzymol.*, Aug. 1992, 4(2):151-158.

Ye et al., "Stage-specific embryonic antigen 4 expression in epithelial ovarian carcinoma," *Int. J. Gynecol. Cancer*, Aug. 2010, 20(6):958-964.

Yelton et al., "Affinity maturation of the BR96 anti-carcinoma antibody by codon-based mutagenesis." *J. Immunol.*, Aug. 15, 1995, 155(4):1994-2004.

Yu et al., "Anti-GD2 antibody with GM-CSF, interleukin-2, and isotretinoin for neuroblastoma," *N. Engl. J. Med.*, Sep. 30, 2010, 363(14):1324-1334.

Zapata et al., "Engineering linear F(ab')₂ fragments for efficient production in *Escherichia coli* and enhanced antiproliferative activity," *Protein Eng.*, Oct. 1995, 8(10):1057-1062.

Zarei et al., "Separation and identification of GM1b pathway Neu5Ac- and Neu5Gc gangliosides by on-line nanoHPLC-QToF

(56) References Cited

OTHER PUBLICATIONS

MS and tandem MS: toward glycolipidomics screening of animal cell lines," Glycobiology, Jan. 2010, 20(1):118-126.
Zhang et al., "Selection of tumor antigens as targets for immune attack using immunohistochemistry: I. Focus on gangliosides," Int. J. Cancer, Sep. 26, 1997, 73(1):42-49.
Supplementary European Search Report issued in connection with European patent application No. EP 09798721.8, dated Oct. 24, 2011, 4 pages.
European Search Report issued in connection with European Patent Application No. 15181446.4, dated Dec. 7, 2015, 10 pages.
International Search Report and Written Opinion issued for International application No. PCT/US2009/050754, dated Feb. 24, 2010, 10 pages.
English translation of Office dated Feb. 23, 2016, issued in connection with Japanese patent application No. 2015-0235105, 2 pages.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.
Cheung et al., Meeting Info: 23rd International Symposium on Glycoconjugates, Glyco 23. Split, Croatia. Sep. 15, 2015-Sep. 20, 2015, vol. 32, No. 5, pp. 323.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.
Tsai, Charng-Sheng et al., Cell-Permeable Probe for Identification and Imaging of Sialidases, PNAS, vol. 110, No. 7, 2013, 2466-2471.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem. Biol. 9, 521-526, (2013.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1$^+$ CD4$^+$ CD8$^-$ thymocytes with specific lymphokine secretion," Eur. J. Immunol., Jan. 1993, 23(1):307-310.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," Nature, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013,

(56) References Cited

OTHER PUBLICATIONS vol. 135(45), p. 16895-16903 Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R."In vivo imaging of membraneassociated glycans in developing zebrafish." Science 2008, 320, 664-667.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Blixt, O. et al. Printed covalent glycan array for ligand profiling of diverse glycan binding proteins. Proc. Natl. Acad. Sci. U.S. A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," *Nature*, Jul. 5, 2007, 448(7149):44-49.
Bosmann et al., "Enzyme activity in invasive tumors of human breast and colon," *Proc. Natl. Acad. Sci. USA*, May 1974, 71(5):1833-1837.
Bost, Kenneth et al., Antibodies Against a Peptide Sequence Within the HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell in Situ Using 16S rRNA-Targeted Probes, Biotechniques, 13, 928-931 (1992).
Bricard et al., "Enrichment of human CD4+ Vα24/Vβ11 invariant NKT cells in intrahepatic malignant tumors," *J. Immunol.*, Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Carlsson, Jan et al., Protein Thiolation and Reversible Protein-Protein Conjugation, Biochem J 173: 723-737 (1978).
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Natl. Acad. Sci. USA*, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chart, Ravi et al., Immunoconjuates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Cheng, Peter et al., Oseltamivir-and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Childs et al., Receptor-Binding Specificity of Pandemic Influenza A (H1N1) 2009 Virus Determined by Carbohydrate Microarray. Nat. Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Domain association in immunoglobulin molecules. The packing of variable domains," *J. Mol. Biol.*, Dec. 5, 1985, 186(3):651-663.
Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.
Codelli, J. A. et al., Second-Generation Difluorinated Cyclooctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2.6.7, 1991.
Collins et al., Crystal Structures of Oseltamivir-Resistant Influenza Virus Neuraminidase Mutants, Nature, Jun. 26, 2008, 453(7199):1258-1261.

(56) References Cited

OTHER PUBLICATIONS

Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine $\alpha\beta$ T cells expressing invariant TCR alpha-chains," J. Immunol., Jun. 15, 1997, 158(12):5603-5611.
De Almeida et al., "Thiacycloalkynes for copper-free click chemistry," Angew. Chem. Int. Ed. Engl., Mar. 5, 2012, 51(10):2443-2447.
Debets, M. F. et al., Bioconjugation with Strained Alkenes and Alkynes, Acc. Chem. Res. 2011, 44, 805-815.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant V$\alpha$24-J$\alpha$Q/V$\beta$11 T cell receptor is expressed in all individuals by clonally expanded CD4$^-$8$^-$ T cells," J. Exp. Med., Sep. 1, 1994, 180(3):1171-1176.
Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "$\alpha$-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," J. Exp. Med., Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).

Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Eberl et al., "Selective bystander proliferation of memory CD4$^+$ and CD8$^+$ T cells upon NK T or T cell activation," J. Immunol., Oct. 15, 2000, 165(8):4305-4311.
Eberl et al., "Selective induction of NK cell proliferation and cytotoxicity by activated NKT cells," Eur. J. Immunol., Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-$\beta$-N-acetylglucosaminidase from Streptococcus pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Friscourt, F. et al., A Fluorogenic Probe for the Catalyst-Free Detection of Azide-Tagged Molecules, J. Am. Chem. Soc. 2012, 134, 18809-18815.

(56) References Cited

OTHER PUBLICATIONS

Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun 2005, 73, 4803.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Gordon et al., "Reactivity of biarylazacyclooctynones in copper-free click chemistry," *J. Am. Chem. Soc.*, Jun. 6, 2012, 134(22):9199-9208.
Govorkova et al, Combination chemotherapy for influenza. Viruses. Aug. 2010;2(8):1510-29.
Graham, Duncan et al., Surface-Enhanced Resonance Raman Scattering as a Novel Method of DNA Discrimination, Angew. Chem., 2000, 112(6), 1103-1105.
Grandjean, C. et al., On the Preparation of Carbohydrate-Protein Conjugates Using the Traceless Staudinger Ligation, J Org Chem 2005, 70, 7123-7132.

Greenbaum et al., "Chemical approaches for functionally probing the proteome," *Mol. Cell. Proteomics*, 2002, 1:60-68.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immuol.*, May 1, 1995, 154(9):4322-4332.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hasegawa, Akira, et al., Synthesis of Sialyl Lewis X Ganglioside Analogues Containing Modified L-Fucose Residues, Carbohydr. Res. 1995, 274, 165-181.
Healthy Living, "10 Simple and Natural Ways to Boost Your Immune System," Published Jan. 31, 2014, downloaded fom online http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Hirabayashi, J. et al., Oligosaccharide Microarrays for Glycomics, Trends in Biotechnology 21 (4): 141-143, 2003.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6):198-200.
Hsu et al., "Alkynyl sugar analogs for the labeling and visualization of glycoconjugates in cells," *Proc. Natl. Acad. Sci. USA*, Feb. 20, 2007, 104(8), 2614-2619.
Huang, Lijun et al., Iterative One-Pot Syntheses of Chitotetroses, Carbohydr. Res. 2006, 341, 1669-1679.

(56) References Cited

OTHER PUBLICATIONS

Huang et al., Recombinant immunotherpaeutics: current state and perspectives regarding the feasibility and market, Appl Microbiol Biotechnol, 87: 401-410. 2010.
Immunogenicity, Wikipedia p. 1-3. Downloaded on Aug. 16, 2016 from https://en.wikipedia.org/wiki/Immunogenicity. (2016).
International Search Report and Written Opinion issued for International application No. PCT/US2015/011748, dated Aug. 21, 2015, 17 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jacobs et al., "Metabolic labeling of glycoproteins with chemical tags through unnatural sialic acid biosynthesis," *Methods Enzymol.*, 2000, 327:260-275.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kanie, Osmau et al., Orthogonal glycosylation strategy in synthesis of extended blood group B determinant. Tetrahedron Lett. 37, 4551-4554 (1996).
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Katagiri, Yohko et al., Laminin Binding Protein, 34/67 Laminin Receptor, Carries, Stage-Specific Embryonic Antigen-4 Epitope Defined by Monoclonal Antibody Raft.2, Biochemical and Biophysical Research Communcations, 332, 1004-1011, 2005.
Kawakami et al., "Critical role of V$\alpha$14$^+$ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of v$_\alpha$14 NKT cells by glycosylceramides," *Science*, Nov. 28, 1997, 278(5343):1626-1629.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia Coli*, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "$\alpha$-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.

(56) References Cited

OTHER PUBLICATIONS

Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.

Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.

Kong, L. et al. Expression-system-dependent modulation of HIV-I envelope glycoprotein antigenicity and immunogenicity. J. Mol. Biol. 403, 131-147, (2010).

Kos, "Regulation of adaptive immunity by natural killer cells," *Immunol. Res.*, 1998, 17(3):303-312.

Koshihara et al., 1984, Biochmica et biophysica acta, 792(1), pp. 92-97.

Kotteas et al., Immunotherapy for pancreatic cancer, J cancer Res Clin Oncol, 142(8): 1795-1805, 2016.

Krise, Jeffrey et al., Prodrugs of Phosphates, Phosphonates, and Phosphinates, Adv. Drug Deliv. Rev. 1996, 19(2), 287-310.

Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.

Kubin, R. F. et al., Fluorescence Quantum Yields of Some Rhodamine Dyes, Luminescence 1982, 27, 455-462.

Kubler-Kielb, J. et al., A New Method for Conjugation of Carbohydrates to Proteins Using an Aminooxy-Thiol Heterbifunctional Linker, J Org Chem 2005, 70, 6987-6990.

Kwong, Peter et al., Rational Design of Vaccines to Elicit Broadly Neutralizing Antibodies to HIV-I. Cold Spring Harb.Perspect. Med. 1, 2011, 1-16.

Lantz et al., "An invariant T cell receptor α chain is used by a unique subset of major histocompatibility complex class I-specific CD4$^+$ and CD4$^-$8$^-$ T cells in mice and humans," *J. Exp. Med.*, Sep. 1, 1994, 180(3):1097-1106.

Lau, K. et al. Highly efficient chemoenzymatic synthesis of β1-4-linked galactosides with promiscuous bacterial β1-4-galactosyltransferases. Chem. Commun. 46, 6066-6068, (2010).

Le, Mai et al., Avian flu: Isolation of Drug-Resistant H5N1 Virus, Nature, Oct. 20, 2005, 437(7062):1108.

Lebens et al., Mucosal vaccines based on the use of cholera toxin B as immunogen and antigen carrier, *Dev. Biol. Stand.*, 1994, 82:215-227.

Le Droumaguet, C. et al., Fluorogenic Click Reaction., Chem. Soc. Rev. 2010, 39, 1233-1239.

Lederman et al., A single amino acid substitution in a common African allele of the CD4 molecule ablates binding of the monoclonal antibody, OKT4, Molecular Immunology, 28, 1171-1181 (1991).

Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.

Lee et al., A new Solvent System for Efficient Synthesis of 1,2,3-Triazoles, Tetrahedron Lett., Jul. 17, 2006, 47(29):5105-5109.

Lee et al., An Efficient and Practical Method for the Synthesis of Mono-N-Protected α,ω-diaminoalkanes, Tetrahedron Lett., Apr. 2, 2001, 42(14):2709-2711.

Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004).

Lee et al., Immunogenicity Study of Globo H Analogues with Modification at the Reducing or Nonreducing end of the tumor antigen, J Am Chem Soc, 136: 16844-16853 (2014).

Lemieux, R. U. et al., Halide ion catalyzed glycosidation reactions. Syntheses of a-linked disaccharides. J Am. Chem. Soc. 97(14), 4056-62, (1975).

Lew et al., Discovery and Development of GS 4104 (oseltamivir): an Orally Active Influenza Neuraminidase Inhibitor, Curr Med Chem, Jun. 2000, 7(6):663-672.

Li et al., β-endorphin omission analogs: Dissociation of Immunoreactivity from other biological activities, Proc Natl Avad Sci USA, 77:3211-3214 (1980).

Li, Y. L. et al., Crystallization and Melting Behaviors of PPC-BS/PVA Blends, 19, 1557-1566, 2003.

Li, Henghui et al., MALDI-MS Analysis of Sialylated N-Glycan Linkage Isomers Using Solid-Phase Two Step Derivatization Method, Analytica Chimica Acta 924 (2016) 77-85.

Li et al., "Design of a potent CD1d-binding NKT cell ligand as a vaccine adjuvant," *Proc. Natl. Acad. Sci. USA*, Jul. 20, 2010, 107:13010-13015.

Li, J.; Hu, M.; Yao, S. Q. "Rapid synthesis, screening, and identification of xanthone and xanthene-based fluorophores using click chemistry." Org. Lett. 2009, 11, 3008-3011.

Li, Lingling, et al., "Syntheses and spectral properties of functionalized, water-soluble BODIPY derivatives." J. Org. Chem. 2008, 73, 1963-1970.

Li, L. et al. Efficient chemoenzymatic synthesis of an N-glycan isomer library. Chem. Sci. 6, 5652-5661 (2015).

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Liang et al., "Quantitative microarray analysis of intact glycolipid-CD1d interaction and correlation with cell-based cytokine production," *J. Am. Chem. Soc.*, Sep. 17, 2008, 130(37):12348-12354.

Liang, Chi-Hui et al., Iron Oxide/Gold Core/Shell Nanoparticles for Ultrasensitive Detection of Carbohydrate-Protein Interactions, Anal. Chem. 2009; 81, 7750-7756.

Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.

Lin et al., A common glycan structure on immunoglobulin G for enhancement of effector functions, PNAS, Aug. 25, 2015, vol. 112, No. 34, p. 10611-10616.

Liu et al., "Activity-based protein profiling: the serine hydrolases," *Proc. Natl. Acad. Sci. USA*, Dec. 21, 1999, 96(26):14694-14699.

Liu et al., Enhanced anti-influenza agents conjugated with anti-inflammatory activity. J Med Chem. Oct. 11, 2012;55(19):8493-501.

Liu et al., Intramolecular ion-pair prodrugs of znamivir nad guanidino-oseltamivir. Bioorganic & Medicinal Chemistry. Jun. 2011; 19(16):4796-4802.

Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.

Lopes, J.F. et al., Simulataneous Chromatographic Separation of Enantiomers, Anomers and Structural Isomers of Some Biologically Relevant Monsaccharides. J. Chomatogr. A, (2008) 1188:34-42.

Lou, et al., Stage-specific embryonic antigent-4 as a potential therapeutic target in glioblastoma multiforms and other cancers. Proc Natl Acad Sci USA 2014, 111(7):2482-7.

Loudet, A.; Burgess, K. "BODIPY dyes and their derivatives: syntheses and spectroscopic properties." Chem. Rev. 2007, 107, 4891-4932.

Lu et al., "Design of a mechanism-based probe for neuraminidase to capture influenza viruses," *Angew. Chem. Int. Ed. Engl.*, Oct. 28, 2005, 44(42):6888-6892.

Lu, Guokai et al., Reactivity-Based One-Pot Synthesis of Immunosuppressive Glycolipids From the Caribbean Sponge Plakortis Simplex, J. Chem. 2009, 27, 2217-2222.

MacBeath, G. and Schreiber, S. L., Printing Proteins as Microarrays for High-Throughput Function Determination, Science, 289, 1760-1763, 2000.

Makino et al., Predominant expression of invariant V$_\alpha$14$^+$ TCR α chain in NK1.1$^+$ T cell populations, *Int. Immunol.*, Jul. 1995, 7(7):1157-1161.

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

(56) References Cited

OTHER PUBLICATIONS

Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," Nat. Biotechnol., Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McLellan, J. S. et al. Structure of HIV-I gpl20 V1/V2 domain with broadly neutralizing antibody PG9. Nature 480, 336-343, 2011.
Medelson et al., NKp46 O-glycan Sequences that are involved in the interaction with Hemagglutinin Type 1 of Influenza Virus. J. Virol. Feb. 10, 2010, 84(8):3789-3797.
Merck, MAB4304, Anti-Stage-Specific Embryonic Antigen-4 Antibody, Clone MC-813-70, 4 Pages, 2017.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Moscona, "Global transmission of oseltamivir-resistant influenza," N. Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Ni, Jing et al., Immunoassay Readout Method Using Extrinsic Raman Labels Adsorbed on Immunogold Colloids, Anal. Chem., 1999, 71(21), pp. 4903-4908.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.
Olden, Kenneth et al., Carbohydrate Moieties of Glycoproteins: A Re-Evaluation of Their Function, Biochem et Biophys Acta 650:209-232 (1982).
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).

(56) References Cited

OTHER PUBLICATIONS

Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," Biochemistry, Jan. 16, 2007, 46(2):350-358.
Paulson, J. C., Blixt, 0. & Collins, B. E. Sweet spots in functional glycomics. Nat. Chem. Biol. 2, 238-248, (2006).
Peelle et al., "Characterization and use of green fluorescent proteins from Renilla mulleri and Ptilosarcus guernyi for the human cell display of functional peptides," J. Protein Chem., Aug. 2001, 20(6):507-519.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," Immunity, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965.
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Poloukhtine et al., "Selective labeling of living cells by a photo-triggered click reaction, " J. Am. Chem. Soc., Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).

Raju et al., "Synthesis and evaluation of 3"- and 4"-deoxy and -fluoro analogs of the immunostimulatory glycolipid, KRN7000," Bioorg. Med. Chem. Lett., 2009, 19:4122-4125.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gpl20 depend on the type of expressing cells and affect antibody recognition. J. Biol. Chem. 285, 20860-20869, (2010).
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Romagnani, "Induction of $T_H1$ and $T_H2$ responses: a key role for the 'natural' immune response?" Immunol. Today, Oct. 1992, 13(10):379-381.
Rosenstein, N. E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," Angew. Chem. Int. Ed. Engl., Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rudnick et al., Affinity and Avidity in Antibody-Based Tumor Targeting, Can Biotherp & Radoipharm, 24, 155-162 (2009).
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Salisbury et al., "Activity-based probes for proteomic profiling of histone deacetylase complexes," Proc. Natl. Acad. Sci. USA, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sletten et al., "Bioorthogonal Chemistry: Fishing for Selectivity in a Sea of Functionality," Angew. Che. Int. Ed. Engl., Aug. 27, 2009, 48(38):6974-6998.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," Proc. Natl. Acad. Sci. USA, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.

(56) References Cited

OTHER PUBLICATIONS

Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," J. Biol. Chem., May 10, 1972, 247(9):2742-2746.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," J. Biol. Chem., Aug. 27, 2004, 279(35):37021-37029.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et al., "Proteomic profiling of metalloprotease activities with cocktails of active-site probes," *Nat. Chem. Biol.*, May 2006, 2(5):274-281.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Sok, Devin et al., SnapShot: Broadly Neutralizing Antibodies. Cell 155, 728-728, (2013).

Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Sutton, VR et al., Bcl-2 Prevents Apoptosis Induced by Perforin and Granzyme B, but Not That Mediated by Whole Cytotoxic Lymphocytes, J of Immunology 1997, 158(12), 5783.
Tahir et al., "Loss of IFN-γ production by invariant NK T cells in advanced cancer," *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from *vibrio* sp. JT-FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.

(56) References Cited

OTHER PUBLICATIONS

Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai et al., "Design and synthesis of activity probes for glycosidases," Org. Lett., Oct. 17, 2002, 4(21):3607-3610.
Tsai, Charng-sheng et al., Development of Trifunctional Probes for Glycoproteomic Analysis, Chem. Commun. 2010, 46, 5575-5577.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.

Varki, "Glycan-based interactions involving vertebrate sialic-acid-recognizing proteins," Nature, Apr. 26, 2007, 446(7139):1023-1029.
Vasella et al., "Synthesis of a phosphoric acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," Methods Mol. Biol., 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus N1 neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).

(56) References Cited

OTHER PUBLICATIONS

Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the lgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.

Yamane-Ohnuki, Naoko et al., Production of Therapeutic Antibodies with Controlled Fucosylation, mAbs 2009, 1;3:230-236.
Yamashita, A et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "$CD4^{pos}$, $NK1.1^{pos}$ T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zhang et al., "New cerebrosides from Acanthopanax gracilistylus," CAPLUS 156:225776 (2011).
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
European Application 14817316.4, Communication pursuant to Article 94(3), dated Apr. 16, 2018, 5 pages.
Herter et al "Glycoengineering of therapeutic antibodies enhances monocyte/macrophage-mediated phagocytosis and cytotoxicity" J Immunol. Mar. 1, 2014, vol. 192 No. 5, pp. 2252-2260.
Japanese Office Action dated Aug. 29, 2017, from Related Japanese Patent Application No. 2016-169045, 5 Pages.
Jez et al "Significant Impact of Single N-Glycan Residues on the Biological Activity of Fc-based Antibody-like Fragments" Journal of Biological Chemistry Jul. 13, 2012, vol. 287 No. 29, pp. 24313-24319.
Junttila et al "Superior in vivo efficacy of afucosylated trastuzumab in the treatment of HER2-amplified breast cancer" Cancer Res. 2010, vol. 70 No. 11, pp. 4481-4489.
Komarova et al "Plant-Made Trastuzumab (Herceptin) Inhibits HER2/Neu+ Cell Proliferation and Retards Tumor Growth" PLOS One 2011,vol. 6 No. 3, p. e17541.
McConville, Malcolm J., and M. A. Ferguson. "The structure, biosynthesis and function of glycosylated phosphatidylinositols in the parasitic protozoa and higher eukaryotes." Biochemical Journal 294.Pt 2 (1993): 305.
Ochiai et al "Expeditious Chemoenzymatic Synthesis of Homogeneous N-Glycoproteins Carrying Defined Oligosaccharide Ligands" J Am Chem Soc. 2008, vol. 130 No. 41, pp. 13790-13803.

(56) References Cited

OTHER PUBLICATIONS

Tebbey et al "Importance of manufacturing consistency of the glycosylated monoclonal antibody adalimumab (Humira®) and potential impact on the clinical use of biosimilars" GABI Journal 2016, vol. 5 Issue 2, pp. 70-73.

Wiseman, Gregory A., et al. "Radiation dosimetry results and safety correlations from (90) Y-ibritumomab tiuxetan radioimmunotherapy for relapsed or refractory non-Hodgkin's lymphoma: Combined data from 4 clinical trials" The Journal of Nuclear Medicine 44.3 (2003): 465-474.

Zhang et al "Glycoengineered Pichia produced anti-HER2 is comparable to trastuzumab in preclinical study" mAbs May-Jun. 2011, vol. 3 No. 3, pp. 289-298.

Greene, Theodora et al., Protective Groups in Organic Synthesis, pp. 42-51 and 96-100, 1991.

Schelhaas, Michael et al., Protecting Group Strategies in Organic Synthesis, Angew. Chem. Int. Ed. Engl. 1996, 35, 2056-2083.

Unverzagt, Carlo et al., A Double Regio- and Stereoselective Glycosylation Strategy for the Synthesis of N-Glycans, Chem. Eur. J., 2008, 14, 1304-1311.

\* cited by examiner

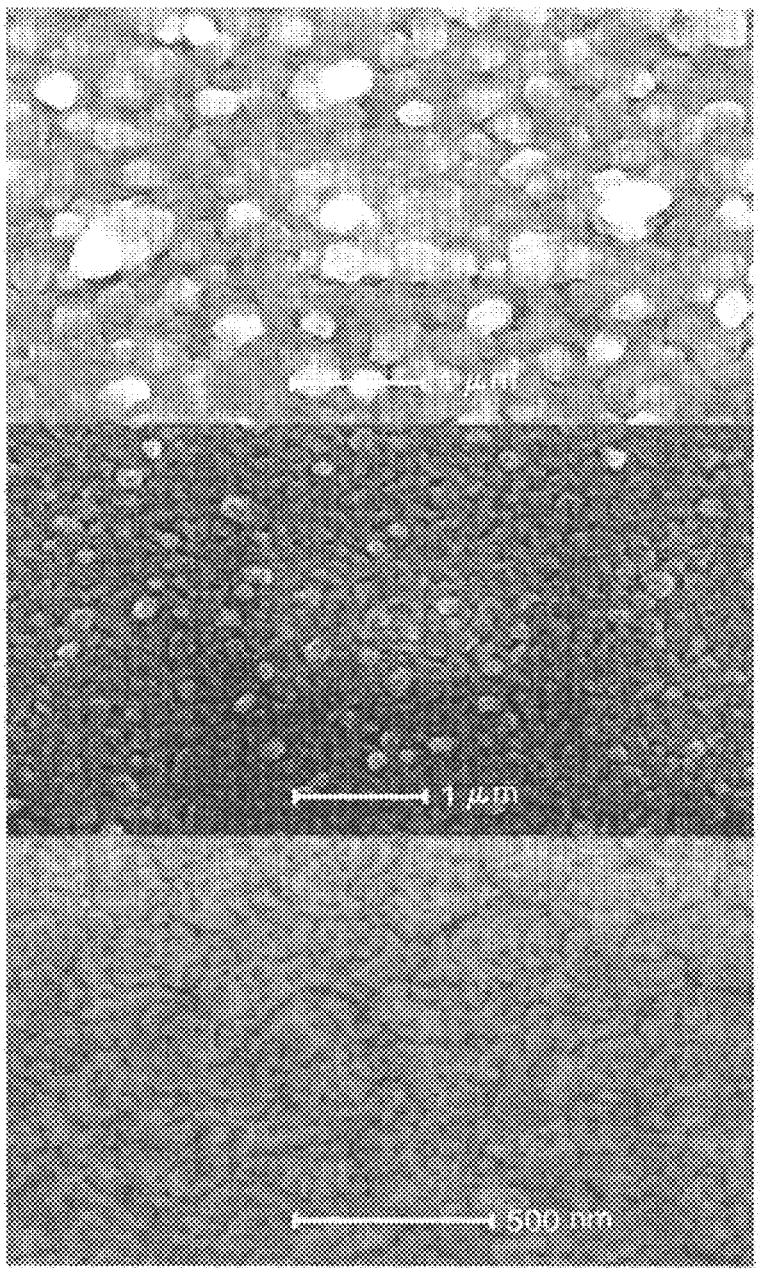

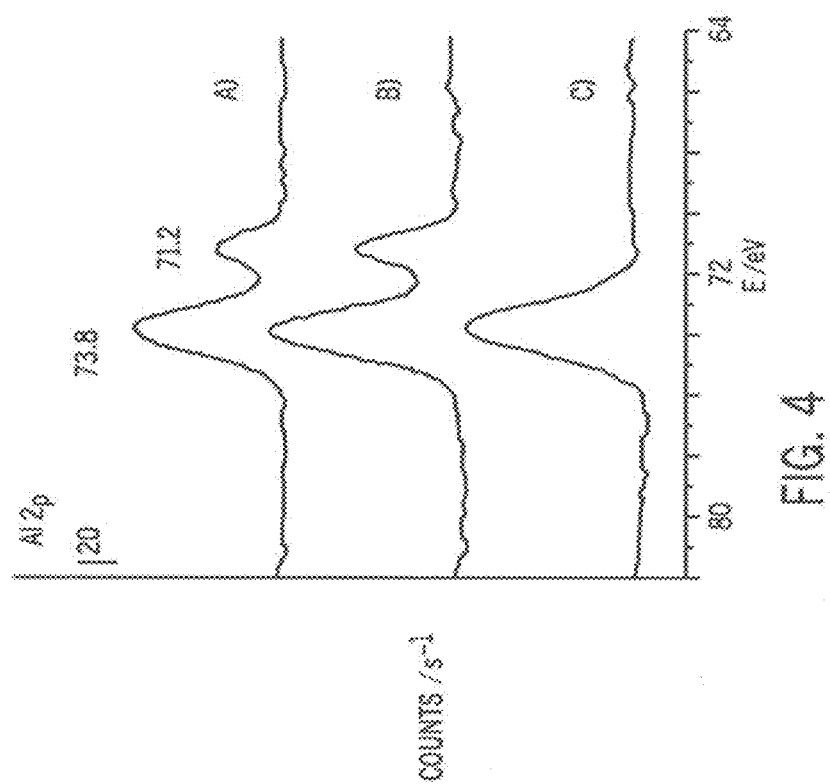

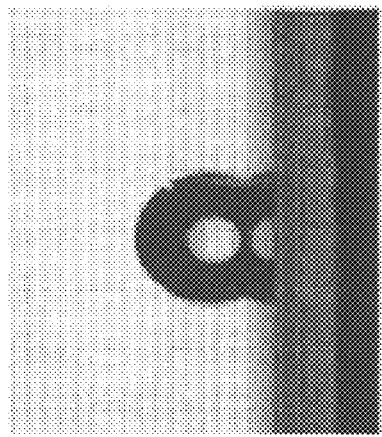
FIG. 7A
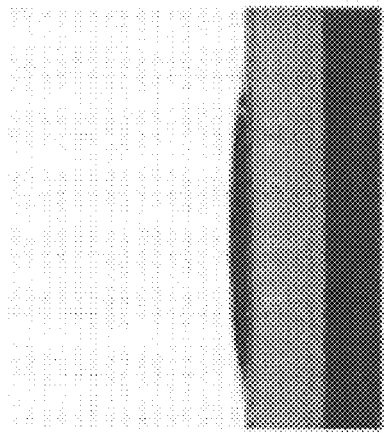
FIG. 7B
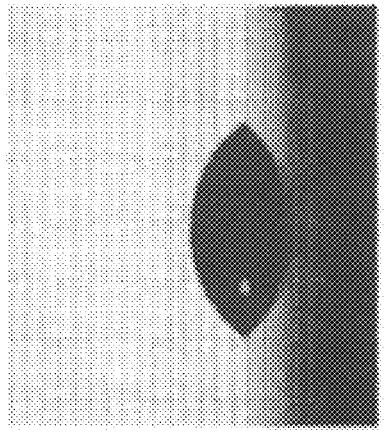
FIG. 7C
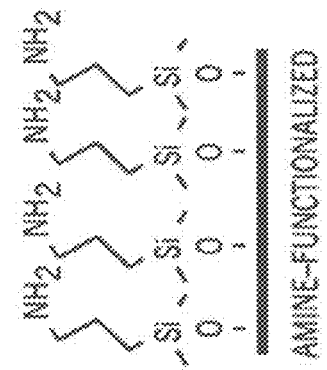

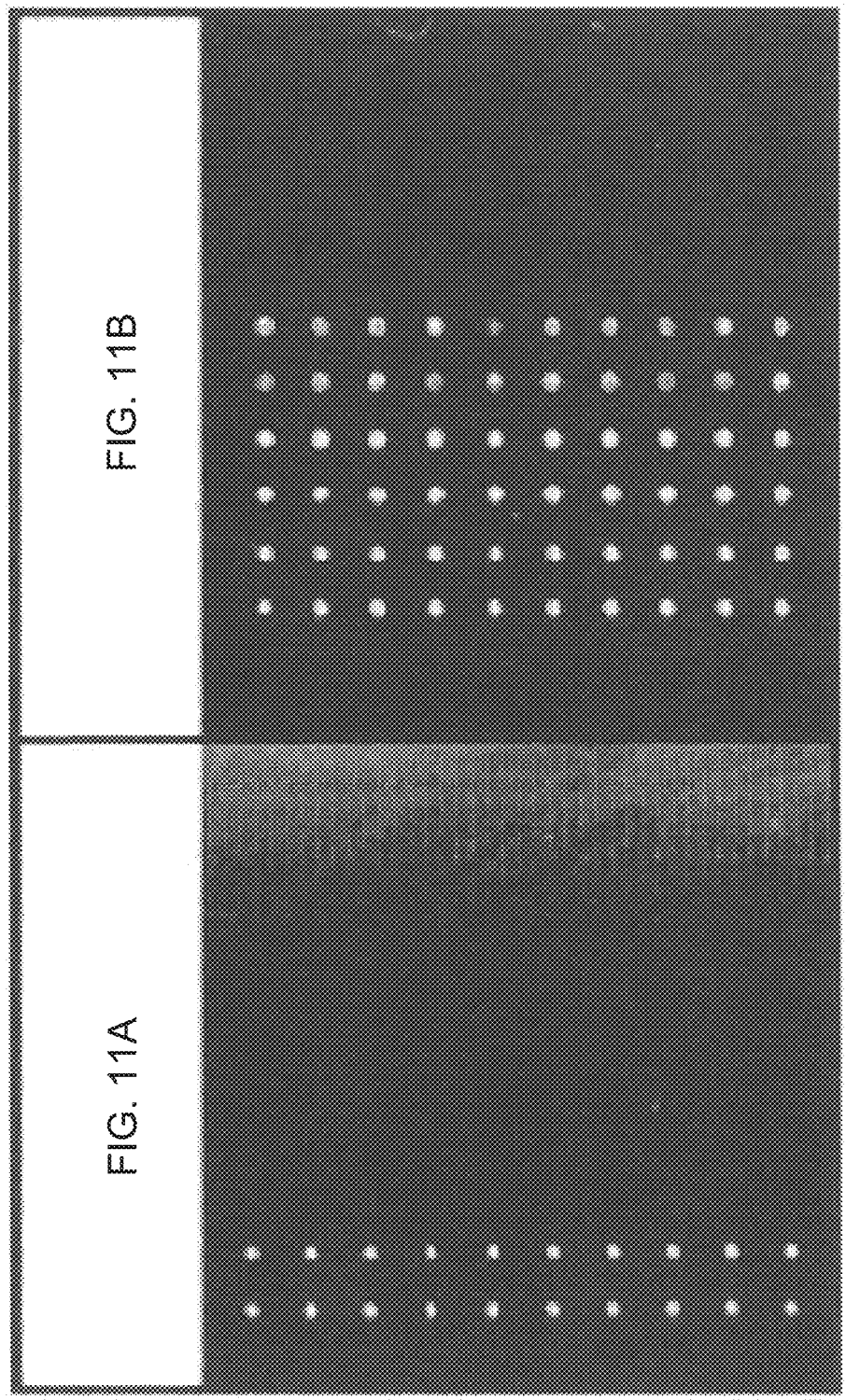

GLYCAN ARRAYS ON PTFE-LIKE ALUMINUM COATED GLASS SLIDES AND RELATED METHODS

CROSS-REFERENCE TO RELATED APPLICATIONS

This application is a divisional application of U.S. patent application Ser. No. 12/503,797 filed Jul. 15, 2009 and issued as U.S. Pat. No. 8,680,020 on Mar. 25, 2014, which claims the benefit of and priority to U.S. Provisional Application Ser. No. 61/080,931, filed Jul. 15, 2008 and U.S. Provisional Application Ser. No. 61/107,624, filed Oct. 22, 2008, the contents of which are incorporated by reference herein in their entirety.

TECHNICAL FIELD OF THE INVENTION

The present invention relates to novel and improved products in the field of array technology. Specifically, the invention relates to carbohydrate arrays immobilized on an aluminum-coated transparent solid substrate or a PTFE-like aluminum-coated transparent solid substrate. More specifically, the invention relates to carbohydrates immobilized on a surface of an aluminum-coated transparent solid substrate suitable for performing mass spectroscopic characterization of the immobilized carbohydrates. More specifically, the invention relates to analysis of binding reactions between the carbohydrates and molecules suspected of specifically binding the carbohydrates.

BACKGROUND OF THE INVENTION

Glycan arrays on novel aluminum coated glass slides, including poly-fluorophosphonated aluminum coated glass slides, allow characterization by mass spectrometry without matrix, fluorescence assessment of sugar-protein binding, and identification and study of enzymes with different efficiency and specificity.

Based on the SWISS-PROT protein database, more than 50% of human proteins are predicted to be glycosylated. Carbohydrates often exist on cell surfaces as glycoprotein or glycolipid conjugates and play important structural and functional roles in numerous biological recognition processes, for example, protein folding, secretion and stabilization, viral and bacterial infection, cancer metastasis, inflammatory response, innate and adaptive immunity, and many other receptor-mediated signaling processes. Moreover, there exist many examples in which glycosylation is required for biological activities. Furthermore, many organisms such as sessile plants have evolved specific glycosylation mechanisms to detoxify harmful exogenous xenobiotics.

Despite the increasing awareness of the biological significance of carbohydrates, the study of carbohydrate-protein interactions still encounters much difficulty, largely because of the structure complexity and synthetic difficulty of carbohydrates and the low affinity of their interactions with glycan-binding proteins (GBPs). Typically the monomeric dissociation constant (KD) in a carbohydrate-protein interaction is in the millimolar range; thus, carbohydrate-mediated biological responses are often through multivalent interaction on the cell surface in order to achieve high affinity and specificity.

A major challenge in cell biology is to define the interaction of oligosaccharides and proteins involved in many biological processes. However, pure oligosaccharides are difficult to obtain and there is a need for development of highly sensitive and high-throughput methods for identification and binding study of carbohydrates recognized by various receptors.

Carbohydrate microarrays are a powerful tool for the study of glycobiology and the high-throughput bioassay of epidemic diseases. A fundamental problem of this technology is how to characterize and quantify the oligosaccharides that are covalently bound to the surface. Effective immobilization of sugars on the surface is essential for surviving consecutive substrate washing when evaluating sugar-protein binding. Mass spectrometry (MS) has been reported to be a useful analytical method for the high-throughput characterization of immobilized sugars on porous glass slides.

Although a variety of substrates are commercially available for glycan arrays, they are not suitable for direct mass spectrometric analysis. These substrates include glass and polyethylene terephthalate (PET) coated with amine, carboxylate, N-hydroxysuccinimide (NHS), avidin, epoxy, aldehyde, chelating nickel groups, and so on. In fact, NHS-functionalized glass slides are commonly used for the preparation of glycan arrays. A typical example is that of sugar antigens immobilized on the surface of the glass slide, after which a sugar-binding monoclonal antibody and a fluorescence-tagged secondary antibody were incubated for studies of protein-carbohydrate interaction. Although effective, these glass slides are not ideal for use to characterize the bound sugars by mass spectrometry.

Substrates selected for matrix-assisted laser desorption-ionization time-of-flight (MALDI-TOF) MS should be conductive or semiconductive so that a uniform electric field can be produced under high vacuum. Standard stainless-steel plates are usually the choice for loading the analytes.

In MALDI MS, the energy of the pulse laser beam is absorbed by the matrix (miscible organic chemicals) to prevent sample fragmentation. MALDI-TOF MS is an excellent tool for analyzing high-molecular-weight biomolecules. However, the chemicals in the organic matrix interfere with low-molecular-weight oligosaccharides (typically less than 2000 Da); thus, porous silicon was chosen as the substrate for analyzing biomolecules by MS without the addition of matrix chemicals. In desorption-ionization on silicon (DIOS) MS, biomolecules of relatively low molecular weight were identified on the basis of the m/z ratio of the pseudoparent peak from MS.

SUMMARY OF THE INVENTION

According to a feature of the present disclosure, an array of carbohydrates immobilized on an aluminum-coated transparent solid substrate or a PTFE-like aluminum-coated transparent solid substrate is disclosed. The array comprises a plurality of carbohydrates immobilized at discrete locations on a surface of an aluminum-coated transparent solid substrate, wherein the array is suitable for (a) performing mass spectroscopic characterization of the immobilized carbohydrates, and (b) performing analysis of binding reactions between the carbohydrates and molecules suspected of specifically binding the carbohydrates.

According to features of the present disclosure, the substrate may be conductive or semiconductive of an electrical field.

According to a feature of the present disclosure, the transparent solid substrate may be glass.

According to a feature of the present disclosure, the carbohydrate may be a glycan.

According to a feature of the present disclosure, the carbohydrates may be immobilized by a non-covalent bond.

According to a feature of the present disclosure, the carbohydrates may be polyfluorinated with a —$C_nF_{2n+1}$ ($n>=4$) tail.

According to a feature of the present disclosure, the polyfluorinated carbohydrates may be spotted on the surface of the PTFE-like aluminum-coated transparent solid substrate.

According to a feature of the present disclosure, the carbohydrates may be immobilized by a covalent bond.

According to a feature of the present disclosure, the carbohydrates may be modified with a phosphonic acid functional group.

According to a feature of the present disclosure, the phosphorylated carbohydrates may be immobilized on the surface of the substrate by a chelating interaction between the phosphonic acid group and the aluminum oxide on the surface of the aluminum-coated transparent solid substrate.

According to a feature of the present disclosure, the carbohydrates may be modified with a photocleavable linker and a silane functional group.

According to a feature of the present disclosure, the photocleavable linker has the general formula:

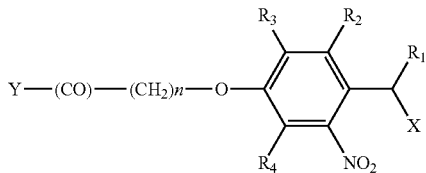

in which $R^1$ is hydrogen, $C_1$-$C_8$ alkyl; $R^2$ and $R^4$ are each independently hydrogen, C1-C8 alkoxy; $R^3$ is $C^1C^8$ alkoxy; X is O(CO)N—$(CH_2)_n$—$R^5$, in which $n>=3$, $R^5$ is carbohydrates, Y is the solid support, like ACG slide.

According to a feature of the present disclosure, the mass spectroscopic characterization of the immobilized carbohydrates comprises a time-of-flight mass spectrometry (MS-TOF).

According to a feature of the present disclosure, the mass spectroscopic characterization of the immobilized carbohydrates comprises a matrix-assisted laser desorption-ionization time-of-flight (MALDI-TOF) mass spectrometry.

According to a feature of the present disclosure, the carbohydrates are polysaccharides, or oligosaccharides, or carbohydrate portions of a glycoconjugate, or cellobiose, or cellotriose, or cellotetraose, or GloboH, or Gb5.

According to a feature of the present disclosure, the mass spectroscopic characterization of the immobilized carbohydrates comprises characterization of the carbohydrate products of a cellulase enzyme reaction.

According to a feature of the present disclosure, the cellulase enzyme reaction is performed on immobilized carbohydrates on the array surface, wherein the cellulase enzyme is suspected of being capable of degrading the immobilized polysaccharides, or oligosaccharides, or carbohydrate portions of a glycoconjugate, or cellobiose, or cellotriose, or cellotetraose, or GloboH, or Gb5.

According to a feature of the present disclosure, the MS-TOF characterization can be performed without adding matrix.

According to a feature of the present disclosure, a carbohydrate binding assay can be performed on the array about 15 minutes following an MS-TOF characterization.

According to a feature of the present disclosure, the molecules suspected of specifically binding the carbohydrates are proteins.

According to a feature of the present disclosure, the proteins are cellulases.

According to a feature of the present disclosure, the cellulases are selected from the group consisting of 1,4-ß-glucosidases, exoglucanases (1,4-ß-D glucan cellobiohydrolases) and endoglucanases (1,4-ß-D glucan glucanohydrolases).

According to a feature of the present disclosure, the proteins analyzed for binding to the carbohydrates immobilized on the array are labeled with a detectable label.

According to a feature of the present disclosure, the protein labels comprise fluorescent dyes.

According to a feature of the present disclosure, the fluorescent dyes comprise amine-reactive dyes.

According to a feature of the present disclosure, disclosed is a computer readable medium comprising data representing the characterization of immobilized carbohydrates on the surface of the array, or data representing the analysis of the carbohydrate binding reactions on the array surface, or both.

According to a feature of the present disclosure, a method for characterization of carbohydrates immobilized on a PTFE-like aluminum-coated transparent solid substrate is disclosed comprising: (a) providing an array comprising a plurality of carbohydrates immobilized at discrete locations on a surface of a PTFE-like aluminum-coated transparent solid substrate; and (b) performing mass spectroscopic analysis to characterize the carbohydrates immobilized at each discrete location.

According to a feature of the present disclosure, the mass spectroscopic characterization of the immobilized carbohydrates comprises a time-of-flight mass spectrometry (MS-TOF).

According to a feature of the present disclosure, the method further comprises: (c) performing a binding analysis of suspected carbohydrate binding moieties.

According to a feature of the present disclosure, the suspected carbohydrate binding moieties are cellulase proteins.

According to a feature of the present disclosure, the method further comprises: (d) incubating the cellulase proteins with the bound carbohydrates immobilized on the array surface under conditions suitable for the cellulases to hydrolyze the carbohydrates.

According to a feature of the present disclosure, the method further comprises: (e) characterizing the products of the cellulase proteins remaining immobilized on the array surface following hydrolysis by the cellulases.

According to a feature of the present disclosure, the cellulases are selected from the group consisting of 1,4-ß-glucosidases, exoglucanases (1,4-ß-D glucan cellobiohydrolases) and endoglucanases (1,4-ß-D glucan glucanohydrolases).

According to a feature of the present disclosure, a method for analysis of binding reactions between the carbohydrates and molecules suspected of specifically binding the carbohydrates is disclosed comprising: (a) providing an array comprising a plurality of carbohydrates immobilized at discrete locations on a surface of an aluminum-coated transparent solid substrate or a PTFE-like aluminum-coated transparent solid substrate; (b) contacting the array with one or more molecules suspected of binding to one or more of the plurality of carbohydrates immobilized on the array surface; and (c) identifying the presence or absence of binding reactions at one or more discrete locations on the array surface.

According to a feature of the present disclosure, the molecules suspected of specifically binding the carbohydrates are proteins labeled with a detectable label.

According to a feature of the present disclosure, the protein labels comprise fluorescent dyes.

According to a feature of the present disclosure, the fluorescent dyes comprise amine-reactive cyanine dyes.

According to a feature of the present disclosure, the binding of a molecule to a carbohydrate on the array is representative of a biological process.

According to a feature of the present disclosure, the biological process is selected from the group consisting of protein folding, protein secretion, protein stabilization, viral infection, bacterial infection, cancer metastasis, inflammatory response, innate immunity, adaptive immunity, a receptor-mediated signaling process, and biofuel production.

According to a feature of the present disclosure, the carbohydrates are polysaccharides, or oligosaccharides, or carbohydrate portions of a glycoconjugate, or cellobiose, or cellotriose, or cellotetraose, or GloboH, or Gb5.

According to a feature of the present disclosure, a mass spectroscopic characterization of the carbohydrates immobilized on the array is performed prior to the binding analysis.

According to a feature of the present disclosure, a mass spectroscopic characterization of the carbohydrates immobilized on the array is performed prior to and following the binding analysis, wherein the one or more molecules suspected of binding to one or more of the plurality of carbohydrates immobilized on the array surface comprises a cellulose protein enzyme capable of hydrolyzing one or more carbohydrates on the array, and wherein the binding reaction is performed under conditions suitable for the cellulose to hydrolyze the carbohydrate.

According to a feature of the present disclosure, the cellulases are selected from the group consisting of 1,4-ß-glucosidases, exoglucanases (1,4-ß-D glucan cellobiohydrolases) and endoglucanases (1,4-ß-D glucan glucanohydrolases).

According to a feature of the present disclosure, a method for fabricating an array of carbohydrates immobilized on an aluminum coated transparent solid substrate or a PTFE-like aluminum-coated transparent solid substrate is disclosed comprising: (a) immobilizing a plurality of carbohydrates at discrete locations on a surface of an aluminum coated transparent solid substrate or a PTFE-like aluminum-coated transparent solid substrate, wherein the substrate is conductive or semiconductive of an electrical field, wherein the array is suitable for performing mass spectroscopic characterization of the immobilized carbohydrates, and wherein the array is suitable for performing analysis of binding reactions between the carbohydrates and molecules suspected of specifically binding the carbohydrates.

According to a feature of the present disclosure, the carbohydrates are immobilized by a non-covalent bond.

According to a feature of the present disclosure, the carbohydrates are polyfluorinated.

According to a feature of the present disclosure, the carbohydrates are immobilized by a covalent bond.

According to a feature of the present disclosure, the carbohydrates are modified with a phosphonic acid functional group.

According to a feature of the present disclosure, the method further comprises (b) performing a characterization of carbohydrates immobilized on the array surface by mass spectrometry, wherein observation of one or more of a high signal/noise (S/N) ratio, low laser fluence rate, or a low fragmentation of signal, in an absence of matrix material is indicative of the array being suitable for performing mass spectroscopic characterization of the immobilized carbohydrates.

According to a feature of the present disclosure, the method further comprises (c) performing a carbohydrate binding assay on the array by contacting the array with a carbohydrate-binding protein, wherein detection of specific binding at one or more discrete locations on the array is indicative of the array being suitable for performing analysis of binding reactions between the carbohydrates and molecules suspected of specifically binding the carbohydrates According to a feature of the present disclosure, the carbohydrate is selected from a sugar, or a glycoprotein, or a glycolipid, or mannose, each comprising internal or nonreducing terminal alpha-mannosyl groups and the binding molecule is Concanavalin A.

According to a feature of the present disclosure, an array for use in disease diagnosis and drug discovery is disclosed, wherein the array is fabricated by (a) immobilizing a plurality of carbohydrates at discrete locations on a surface of an aluminum coated transparent solid substrate or a PTFE-like aluminum-coated transparent solid substrate, wherein the substrate is conductive or semiconductive of an electrical field, wherein the array is suitable for performing mass spectroscopic characterization of the immobilized carbohydrates, and wherein the array is suitable for performing analysis of binding reactions between the carbohydrates and molecules suspected of specifically binding the carbohydrates.

The present invention and other objects, features, and advantages of the present invention will become further apparent in the following Detailed Description of the Invention and the accompanying Figures and embodiments.

BRIEF DESCRIPTION OF THE FIGURES

The above-mentioned features and objects of the present disclosure will become more apparent with reference to the following description taken in conjunction with the accompanying drawings wherein like reference numerals denote like elements and in which:

FIG. 3A-FIG. 3C are microscopy photographs of implementations of aluminum coated glass slides. FIG. 3A shows aluminum deposited by cathode arc evaporation.

FIG. 3B shows an aluminum coating deposited by magnetron sputtering, and FIG. 3C shows aluminum AAO/ACG slide obtained by thermal coating followed by electrochemical surface anodization.

FIG. 4 are graphs of experimental data illustrating the surface composition of ACG slides made by various methods.

FIG. 5A shows a series of Cy3-streptavidin solutions of 1 mg/mL diluted 1000×, 2000×, 5000×, 10000×, and 20000× were spotted on each of these slides, air-dried, and analyzed with an array WoRx fluorescence spectrometer. FIG. 5B shows implementations of experimental data wherein the actual calculated fluorescence intensity for each substrate is shown.

FIG. 7A-FIG. 7C are photographs of the water contact angle on ACG slides demonstrating the efficacy of activation. FIG. 7A shows a solvent-cleaned ACG slide; FIG. 7B shows an ACG slide treated with plasma; and FIG. 7C shows an ACG slide activated with 3-amino-propyldimethylethoxysilane.

FIG. 9A shows the Ultraflex TOF mass spectra of mannose with PCL grafted on (A) a 99.999% pure aluminum plate (1 mm thick) and (B) an ACG slide formed by cathode arc evaporation. (C) represents the background signal for cathode arc evaporation of the ACG slide. FIG. 9B shows the Ultraflex TOF mass spectra of FIG. 9A at the m/z region of interest, FIG. 9C shows TOF mass spectrum of mannose with PCL grafted on an ACG slide formed by cathode arc evaporation at the m/z region of interest.

FIG. 10A shows protein-binding assays of ACG slides formed by cathode arc evaporation upon treatment with a) oxygen plasma (Al-1), b) argon plasma (Al-2), and c) a mixture of oxygen and argon plasma (Al-3) prior to APDMES grafting. In d), protein-binding assay of the commercially available $NH_2$-glass slide from Corning GBlass (#40004) are shown. FIG. 10B shows the signal intensities from MALDI mass spectra for the mass identification of sugar. FIG. 10C shows fluorescence intensities of a)-d) with standard errors calculated with an array WoRx fluorescence spectrometer.

FIG. 11A-FIG. 11B are photographs of implementations of a fluorescence-tagged protein-binding assay of mannose immobilized on a glass slide (FIG. 11A) and an ACG slide (FIG. 11B).

In FIG. 12A, average peak intensities of mannose mass spectrometric adducts obtained at m/z 265.1 $[M]^+$, 266.1 $[M+1]^+$, and 272.1 $[M+Li]^+$ are shown. In FIG. 12B, corresponding fluorescence intensities of the same mannose-ACG slide sample obtained from the fluorescence-tagged protein-binding assay is shown.

FIG. 13A shows Lactose-ACG slide with PCL. FIG. 13B shows Ultraflex TOF mass spectra obtained from the Lactose-ACG slide with PCL. FIG. 13C shows Globo H-ACG slide with no PCL. FIG. 13D shows fluorescence-tagged protein-binding assay of Globo H immobilized on NETS-glass slide, $NH_2$-modified glass slide (Corning #40004), and NETS-ACG slide. Finally, FIG. 13E shows corresponding fluorescence intensities calculated from FIG. 13D with a GenePix 4000 fluorescence scanner.

FIG. 17A illustrates MALDI mass spectrometric analysis data of polyfluorinated Globo H 7 (MW. 1604.40), Gb5 5 (MW. 1458.39) and lactose 6 (MW. 932.21) immobilized on PTFE-like ACG slide. FIG. 17B is a protein-binding assay of GloboH/VK9/anti-VK9-Cy3. FIG. 17C is a protein-binding assay of Gb5/anti-SSEA3-A488.

FIG. 21A shows the various derivates that are possible, together with their molecular weights. FIG. 21B shows implementations of experimental MS-TOF data of enzymatic hydrolysis of poly-fluorinated cellotriose of the control run without enzymes (a), and with the cellulase proteins from *A. niger* (b), *T. reesei* (c), and *A. viride* (d).

In FIG. 26A, (a) represents an MS-TOF result of the background of silane based PTFE-like ACG; (b) represents an MS-TOF result of poly-fluorinated mannose adsorbed on the above ACG slide. FIG. 26B represents implementations of a microarray of silane based PTFE-like ACG slide.

In FIG. 27A, (a) represents an MS-TOF result of the background of phosphonic acid based PTFE-like ACG and (b) represents an MS-TOF result of poly-fluorinated mannose adsorbed on the above ACG slide. FIG. 27B shows a microarray of a phosphonic acid based PTFE-like ACG slide.

DETAILED DESCRIPTION OF THE INVENTION

Figure 1:
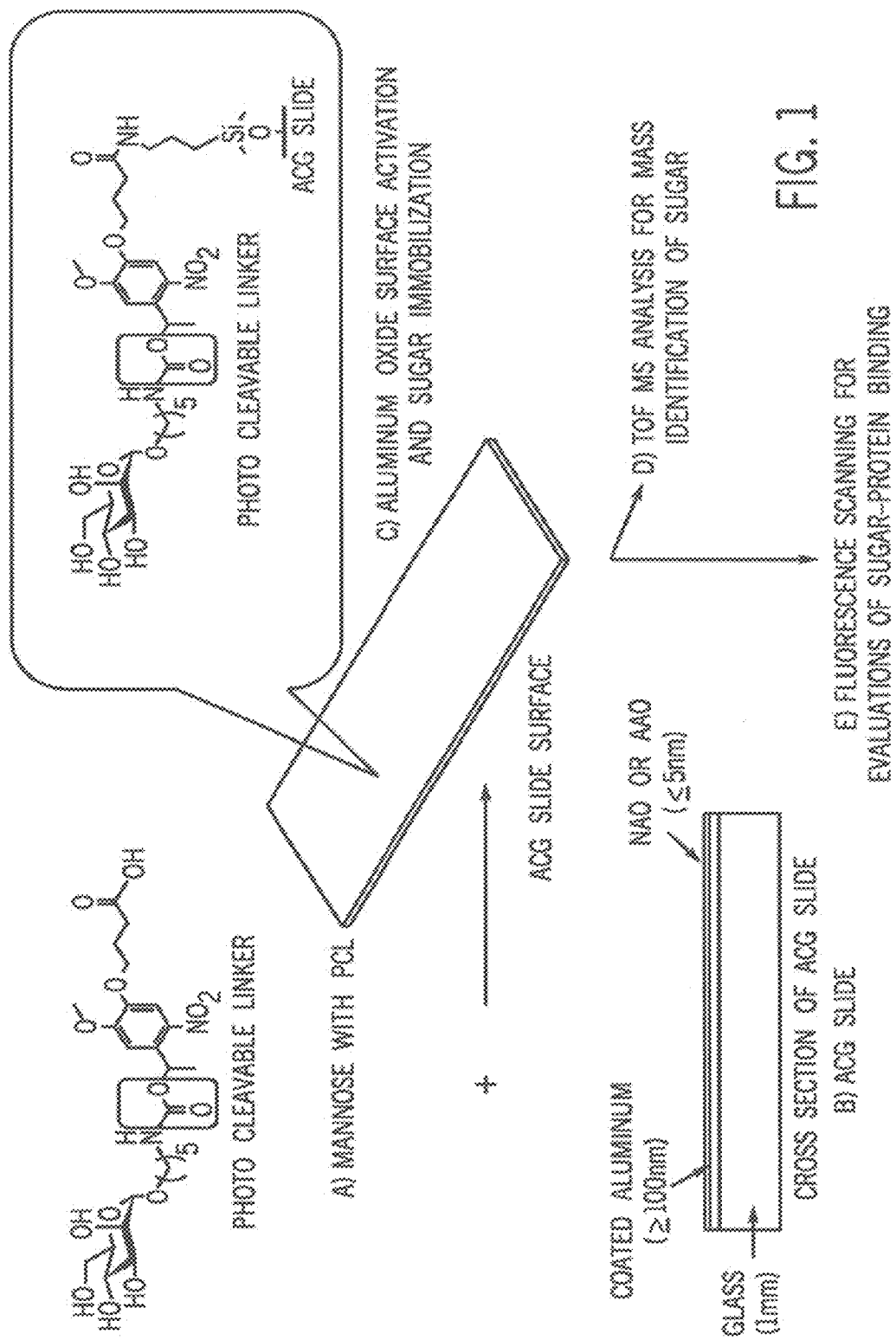
FIG. 1 is a block diagram of implementations and experimental aluminum coated glass (ACG) slide and related experimental techniques.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

This disclosure incorporates by reference U.S. Patent Publication No. 2007/0213278, filed Dec. 22, 2006.

As used herein, the term Teflon or PTFE refers to polytetrafluoroethylene.

Effective adhesion between sugar molecules and the substrate surfaces have been achieved through covalent bonding. Physical adsorption of sugar derivatives on fluorous surfaces may also be feasible for sufficient adhesion. Porous silicon plates also acted as a matrix in DIOS MS, and mass spectra were obtained with a high signal-to-noise (S/N) ratio without fragmentation. The preparation of porous silicon plates requires the usage of corrosive acid, which is not environmentally friendly, and the quality of the plates is difficult to control. On the other hand, porous aluminum oxide exists naturally on the surface of aluminum; the electrochemical anodization of aluminum-coated glass (ACG) slides can be carried out in mildly acidic aqueous solution. Silylation reactions on silicon surfaces can also be used on aluminum surfaces under proper conditions. The freshly cut surface of plate aluminum has a shiny metallic texture. When exposed to air, the surface gradually oxidizes and turns opaque as a layer of aluminum oxide (called native oxide) is formed. Native aluminum oxide (NAO) grown on aluminum surfaces has no orientation compared to that of anodized aluminum oxide (AAO). The thickness of NAO on aluminum surfaces is just a few nanometers. In contrast, the thickness of AAO could grow quickly (within 15-20 min) to the micrometer range with the growing direction aligned to an applied electric field. In a few trial experiments, pure aluminum plates were fabricated (with a thickness of 1 mm) and the AAO layer was grown to 2 mm on the surface of the plate. This surface with a thick layer of AAO became nonconductive (like ceramics) and was not suitable for our study. However, in all cases, the amorphous oxide layers on the aluminum surfaces could be modified chemically, and the substrate remained electrically conductive only when the thickness of the oxide layer on the surface was in the nanometer range.

According to implementations illustrated in FIG. 1, several new substrates with a thin layer of aluminum oxide on the surface of ACG slides were fabricated in an attempt to characterize the molecular weight of the surface-grafted oligosaccharide and simultaneously to look for its sugar-protein binding capability. Designed mannose and lactose derivatives with a built-in photocleavable linker (PCL) were synthesized and covalently bound to the activated ACG slides, as illustrated according to implementations shown in FIG. 2. Without addition of a miscible organic matrix, the sugar-immobilized ACG slides were subjected to molecular-weight identification and protein-binding evaluation.

Cellulases are of current interest because of their application to biofuel production. Cellobiose or cellotriose with fluorogenic or chromogenic groups are commonly used as substrates for the investigation of cellulase activity and specificity. However, during enzymatic hydrolysis, the fluorogenic or chromogenic leaving group generated in the reaction showed signal only at high pH, but, cellulases exhibit their optimum activity at low pH (4-6). Poly-fluorinated cellobiose was immobilized non-covalently on the PTFE-like ACG slides, and conducted the enzymatic hydrolysis at pH 4-6 in situ. The hydrolyzed products remaining on the slide surface were then identified by MS-TOF.

Moreover, the recently developed aluminum coated glass (ACG) slides were oxidized and reacted with a functionalized alkyl monoethoxysilane to form a covalent handle, followed by coupling with a glycan containing the photocleavable linker. This glycan array with a photo-cleavable linker on the ACG slide surfaces can be characterized by time-of-flight mass spectrometry (MS-TOF) without matrix, and used for binding evaluation of fluorescence-tagged proteins. The fluorescence intensity of sugar-protein complex on ACG-slide is higher than on glass slides. A new method is therefore disclosed for fabricating stable poly-fluorinated (also called the PTFE-like) ACG slides, and the use of these slides for non-covalent arraying glycans as substrates for the study of cellulase activities by using mass spectrometry as a detector. Moreover, by using the property of phosphonic acid to chelate with the aluminum oxide surface easily, the carbohydrate with a phosphonic acid linker was used to create covalent bonding glycan array.

According to implementations, a new generation of carbohydrate array on PTFE-like ACG slides have has been developed for immobilizing sugars. Mannose and lactose with a built-in photocleavable linker immobilized on the ACG slide surfaces were subjected to MALDI MS analysis to characterize the molecular weight of the immobilized sugars. A proportional correlation was observed between the quantity of mannose (m/z) and the fluorescence intensity of its protein binding. In protein-binding assays of mannose-ACG and Globo H-ACG slides, higher fluorescence intensity and sensitivity was observed than with glass slides, perhaps due to the material properties, surface morphologies, and binding-site architectures between proteins and the immobilized sugars on the slide surfaces.

With mass spectrometry, this glycan array can be used as an effective analytical tool to identify and differentiate various types of cellulases and their efficiency. The unique properties of aluminum oxide coated glass slides make it possible to conveniently and non-covalently or covalently array glycans via phosphonate chemistry and the glycan array can be characterized with MS spectrometry without the use of matrix.

According to implementations, FIG. 1 illustrates a novel experimental ACG slide and related methods for experimentation thereon. In a), a sugar derivative such as mannose with a built-in photocleavable linker is created, according to implementations. In b) ACG slide (75.5×25.4×1 mm$^3$) with layers of aluminum oxide (<5 nm) on the surface and pure aluminum (>100 nm) coated on the glass slide (1 mm) is shown. In c) the ACG slide was optionally activated, and the sugar derivatives were immobilized (microarrayed and manually spotted) on the surface. The slide was subjected to molecular-weight identification of the sugar by mass spectrometry in d) or further evaluated for its sugar-protein binding by a fluorescence scanner in e).

Figure 2:
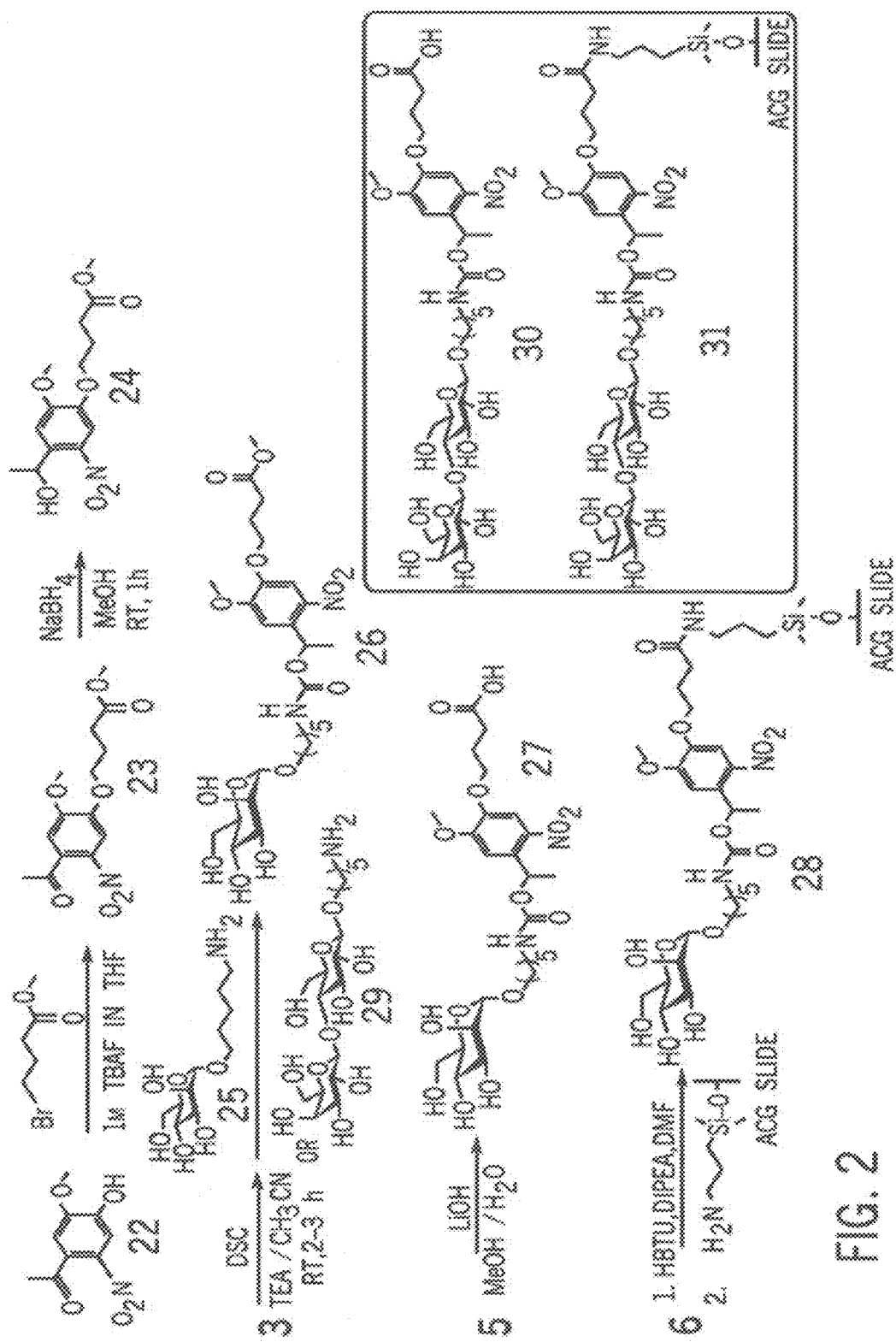
FIG. 2 is a scheme showing an implementation of the synthesis of mannose-ACG and lactose-ACG with a photocleavable linker.

According to implementations and as illustrated in FIG. 2, a scheme is shown the synthesis of mannose-ACG and lactose-ACG with a photocleavable linker; DIPEA=N,N-diisopropylethylamine, DSC=N,N'-disuccinimidyl carbonate, HBTU=2-(1-benzotriazol-1-yl)-1,1,3,3-tetramethyluronium hexafluorophosphate (TBAF=tetra-n-butylammonium fluoride, TEA=triethylamine).

Figure 15:
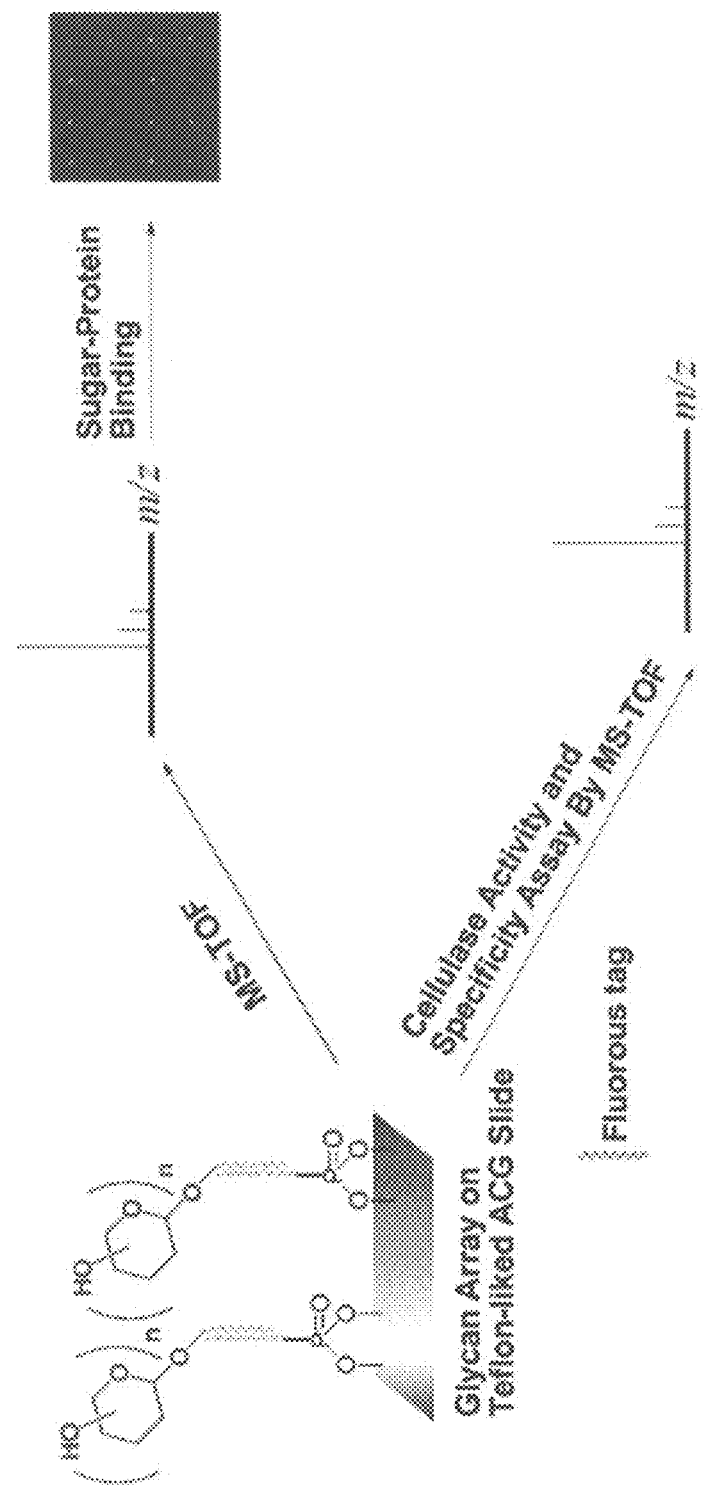
FIG. 15 is a block diagram of an implementation of the creation of non-covalent bond glycan array on the PTFE-like ACG slide.

According to implementations and as illustrated in FIG. 15, a block diagram of an implementation of the creation of non-covalent bond glycan array on the PTFE-like ACG slide is shown. According to the implementation, sugars are reversibly bonded via a poly-fluorinated tail to an ACG slide. Various mass spectroscopy experiments are then performed. For example, MS-TOF is performed in a sugar-binding assay, or cellulase activity and specificity assay by MS-TOF may be performed.

Artisans will readily appreciate both the utility of the apparatuses disclosed herein, as well as the various experimental methods based on the Examples and other disclosure provided here. Such devices and methods are expressly contemplated in this disclosure.

EXAMPLES

Example 1: Surface Properties of ACG Slides

A layer of pure aluminum (99.999%) at least 100 nm thick was coated onto the micro glass slides by using various coating techniques, such as magnetron sputtering, cathode arc evaporation, and thermal coating. These slides were either used without further manipulation or electrically anodized before usage. According to implementations, FIG. 3 shows their surface morphology, composition, and roughness as determined by scanning electron microscopy (SEM), atomic force microscopy (AFM), and X-ray photoelectron spectroscopy (XPS) of an ACG slide. FIG. 3A shows aluminum deposited by cathode arc evaporation, FIG. 3B shows an aluminum coating deposited by magnetron sputtering, and FIG. 3C shows aluminum AAO/ACG slide obtained by thermal coating followed by electrochemical surface anodization.

As can be seen, the ACG slide produced by cathode arc evaporation has a coating of large granules and a high surface roughness. Slides with high surface roughness affect the surface-wetting property. The magnetron-sputtered ACG slide gave an acceptable surface roughness; however, it required a long coating time to achieve the desired coating thickness and was used only at the early stages of this study. Thermal coated ACG slides achieved the desired coating thickness in a relatively short time. It gave the smoothest surface with a surface roughness of 10 nm. With subsequent surface-anodization treatment, the ACG slide provided a stable surface for grafting. Only the anodized slide surfaces were covered with 100% aluminum oxide, as shown in FIG. 4.

According to implementations of experimental data shown in FIG. 4, XPS spectra of the surface composition of a) an NAO/ACG slide obtained by cathode arc evaporation, b) an NAO/ACG slide obtained by magnetron sputtering, and c) an AAO/ACG slide obtained by thermal coating followed by surface anodization are shown. The binding energy for C(1 s) at 284.5 eV and O(1 s) at 531 eV were used to calibrate the binding energy of these spectra. The electrical resistance of the ACG slide (end-to-end distance) was measured between 1.6 and 4Ω. These slides became electrically nonconductive when the oxide layer grew thick. The depth of penetration for XPS was 20-50 Å, and the thickness of the oxide layer (either NAO or AAO) in this study was estimated from the cross-section to be no more than 5 nm.

The thickness of coated aluminum on the glass slide needs to be >100 nm so that the substrate remains non-transparent within the visible region. When a transparent substrate was used, part of the fluorescent light passed through the substance, and the scanner detected only a portion of the Cy3 fluorescence. The instrument detected more fluorescent light when a nontransparent ACG slide was used as the background substrate.

Figure 5A:
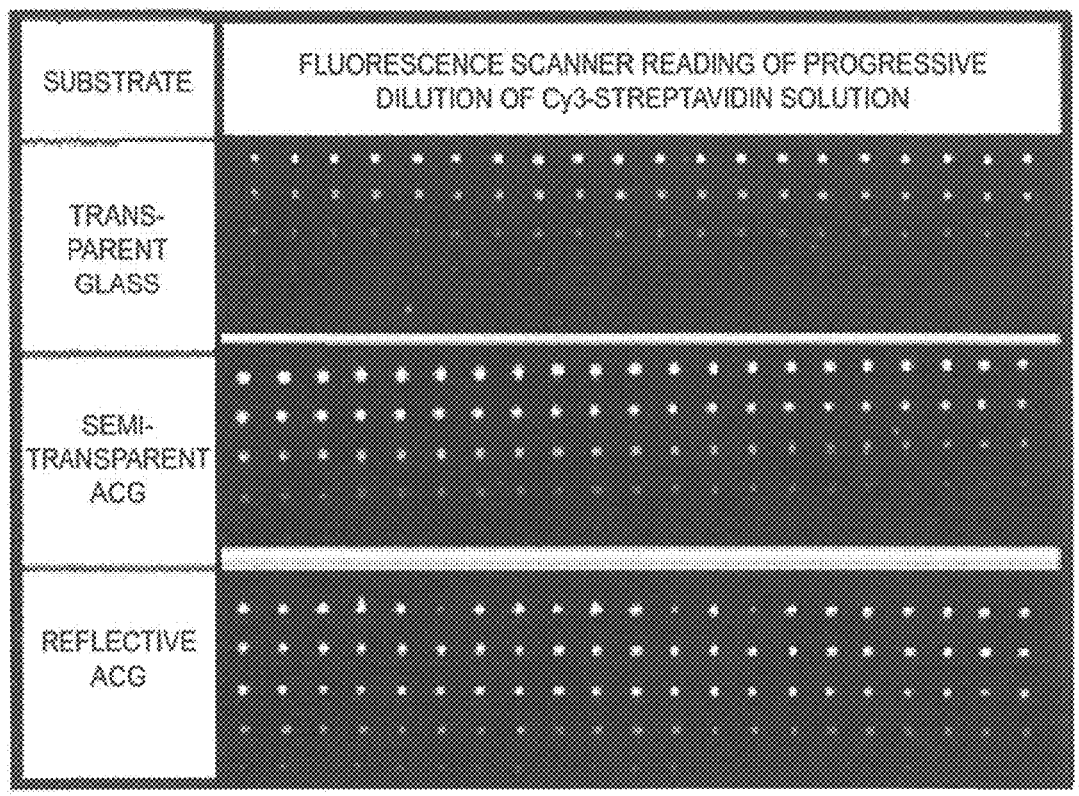
FIG. 5A-FIG. 5B are visual representations of implementations of the optical properties of the micro glass slide, the semitransparent ACG slide, and the totally reflective (non-transparent) ACG slide.
Figure 5B:
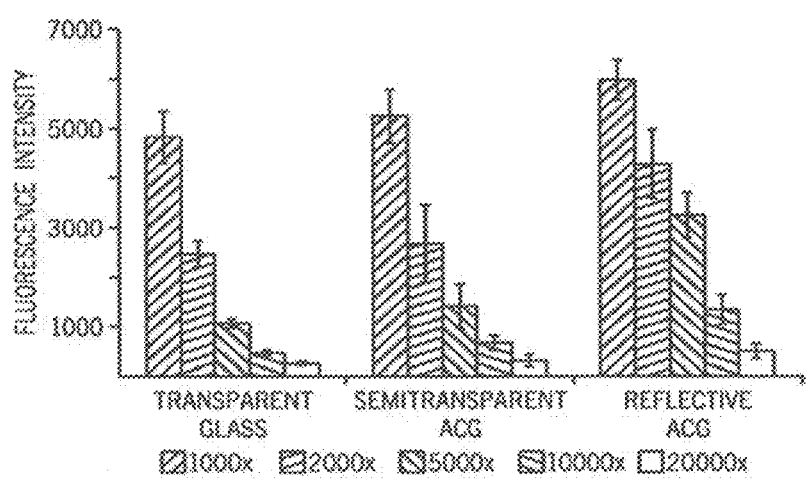

FIG. 5 shows data the optical properties of ACG slides compared to those of the micro glass slide. The thickness of the coated aluminum on the semitransparent ACG slides was just a few nanometers, and that of the reflective ACG slides was approximately 300 nm. FIG. 5 shows the optical properties of the micro glass slide, the semitransparent ACG slide, and the totally reflective (nontransparent) ACG slide. In FIG. 5A, a series of Cy3-streptavidin solutions of 1 mg/mL diluted 1000×, 2000×, 5000×, 10000×, and 20000× was spotted on each of these slides, air-dried, and analyzed with an array WoRx fluorescence spectrometer. A light source of wavelength 540 nm was provided by the instrument. Fluorescence of wavelength 595 nm was emitted from the slide surface and detected by the detector. The scanner detected the fluorescence only up to 5000× dilution for the transparent micro glass slide, but up to 10000× and 20000× times dilution, respectively, for the semitransparent ACG slide and the totally reflective ACG slide, in which the thickness of the coated aluminum varied from a few nanometers in the former to greater than 100 nm in the latter. FIG. 5B shows implementations of experimental data wherein the actual calculated fluorescence intensity for each substrate is shown.

Example 2: Surface Activation

Figure 6:
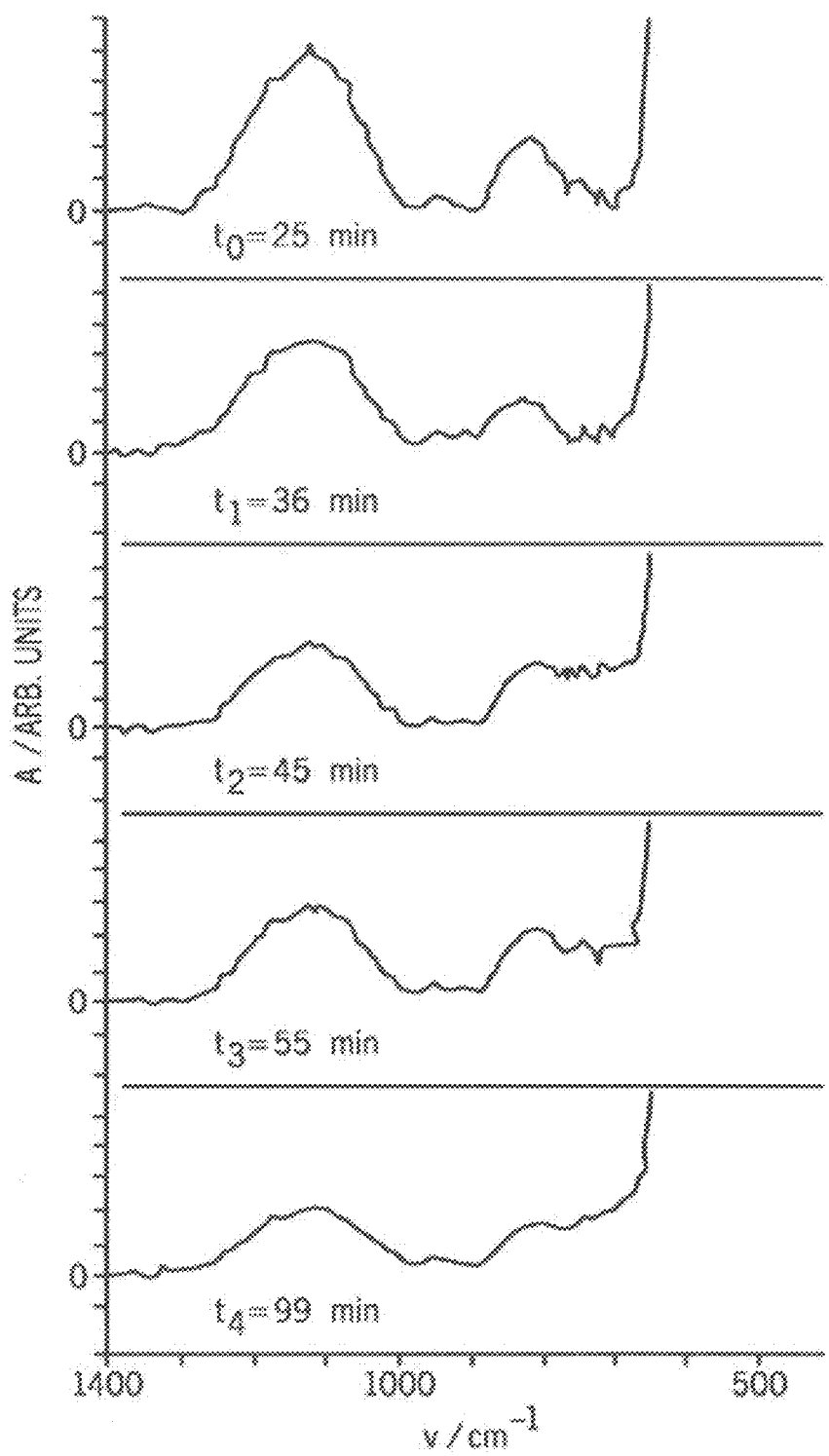
FIG. 6 are graphs of implementations of experimental data showing ATR/FTIR spectra of Al—OH on an ACG slide.

In the screening experiments, plasma of oxygen, argon, and mixed gases of oxygen and argon were tested for slide-surface activation. The residues (CO, $CO_2$, and $H_2O$) were removed under vacuum. It is the removal of this surface contamination that contributed to the success of grafting the desired organic compounds chemically. The surface was gauged with an attenuated total reflectance Fourier transform infrared (ATR/FTIR) spectrometer. The ATR/FTIR spectra showed Al—OH peaks at around 800-1100 cm$^{-1}$, as illustrated in FIG. 6, indicating that the surface had converted into Al—OH after the surface-cleaning process. According to implementations, the plasma treatment uses just enough plasma energy to clean and "tickle" the surface of the ACG slide to remove the organic contamination, but still hold the alumina layer without etching the underlying surface. The activation process was successfully completed by using a mere 6.8 W (at 680 V) of energy for 10 min under a gas-flow pressure of 270-300 mTorr. Argon plasma turned out to be the most effective for grafting sugar derivatives, as observed in later experiments. As shown in FIG. 6, the Al—OH peak intensity in the 800-1100 cm$^{-1}$ region decreased significantly from 25 to 99 min after plasma treatment.

The hydrophilic surface after plasma treatment gradually became hydrophobic, possibly because the oxide layer on the surface reforms. Disappearance of Al—OH from the substrate surface was traced by ATR/FTIR spectroscopy. The Al—OH peak intensity in the 800-1100 cm$^{-1}$ region decreased significantly over a matter of hours, as shown in FIG. 6. According to implementations, the ACG slides are activated with 3-aminopropyl dim ethyl ethoxy silane (AP-DMES) immediately after plasma treatment. This activated ACG surface was used to immobilize the sugar derivative of mannose and lactose with a PCL in the next step of the reaction.

As shown in FIG. 7, the water contact angle on the surface changed during surface activation. According to FIG. 7, the typical changes in water contact angle for ACG slides are shown. FIG. 7A shows a solvent-cleaned ACG slide; FIG. 7B shows an ACG slide treated with plasma; and FIG. 7C shows an ACG slide activated with 3-amino-propyldimethylethoxysilane. These samples were made and measured as an example with the nontransparent magnetron-sputtered ACG slide. Therefore, measurement of the contact angle can be used as a quick check of the completion of the activation process. Substrates with a high surface roughness tend to give smaller contact angles.

Example 3: Mannose with PCL Immobilized on the Activated Surface of the ACG Slide As shown in FIG. 2, compound 27, which has a carboxy functional group, was synthesized. A solution of HBTU and compound 27 was manually spotted and microarrayed on the activated surface of the ACG slide. Amide formation on the surface of the ACG slide took place overnight at room temperature. All salt residues, as well as unbound mannose derivative, were washed away thoroughly with methanol and deionized water. After all these preparations, the substance was ready for mass identification and protein-binding evaluation.

Example 4: Mass Spectrometric Analysis of the Sugar Derivative Grafted on the ACG Slides The matrix-free porous silicon surfaces (DIOS) produced molecular-ion peaks with negligible sample fragmentation. The ACG slide dimensions (75.5×25.4×1 mm$^3$) fit well in the ultraflex mass spectrometry instrument; slides at each step of the treatment were analyzed, as shown in FIGS. 8 and 9.

Figure 8:
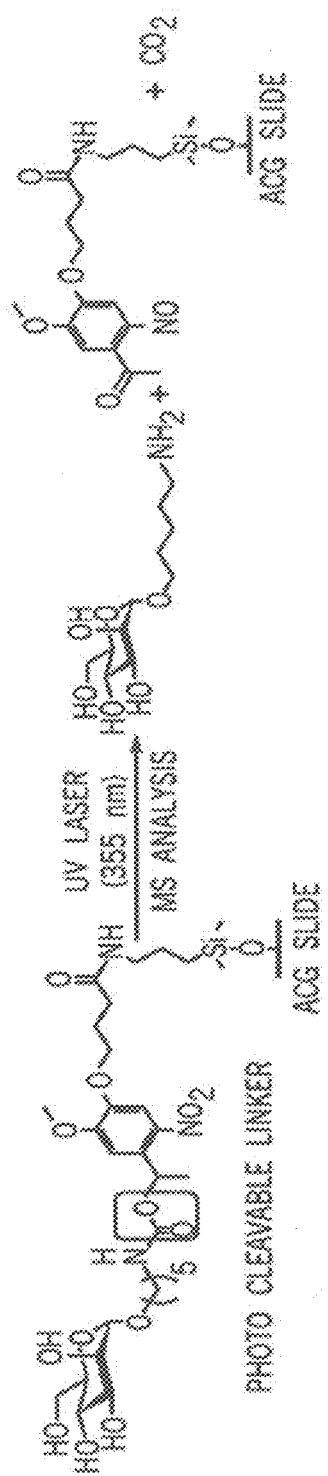
FIG. 8 is an implementation of a scheme for selective bond cleavage and detection of a sugar (mannose) derivative by ultraflex TOF mass spectrometry.

FIG. 8 is an implementation of a scheme for selective bond cleavage and detection of a sugar (mannose) derivative by ultraflex mass spectrometry.

Figure 9A:
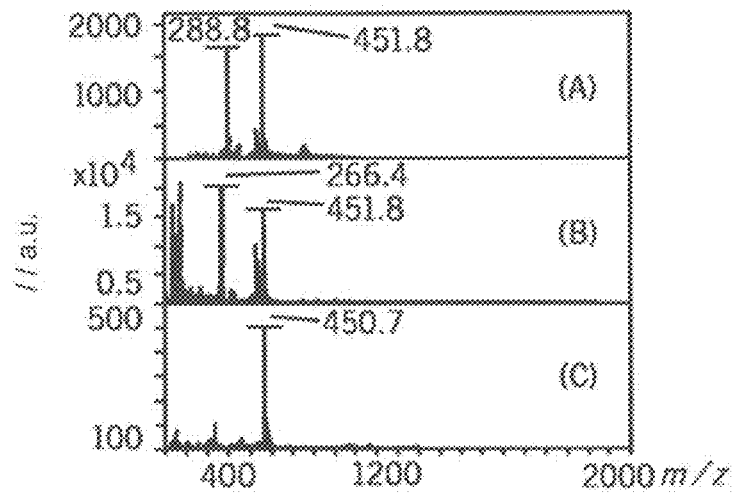
FIG. 9A-FIG. 9C show implementations of mass spectroscopy data on a pure aluminum plate and an ACG slide.
Figure 9B:
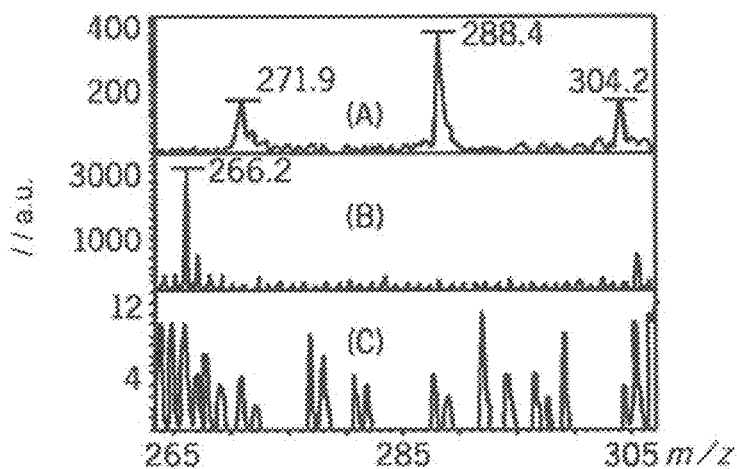

FIGS. 9A and 9B show the MS data for the early experiments on a pure aluminum plate and ACG slide, whereby the mannose peak intensities were relatively low. FIG. 9A shows the Ultraflex TOF mass spectra of mannose with PCL grafted on (A) a 99.999% pure aluminum plate (1 mm thick) and (B) an ACG slide formed by cathode arc evaporation. (C) represents the background signal for cathode arc evaporation of the ACG slide. FIG. 9B shows the Ultraflex TOF mass spectra of FIG. 9A at the m/z region of interest.

Figure 9C:
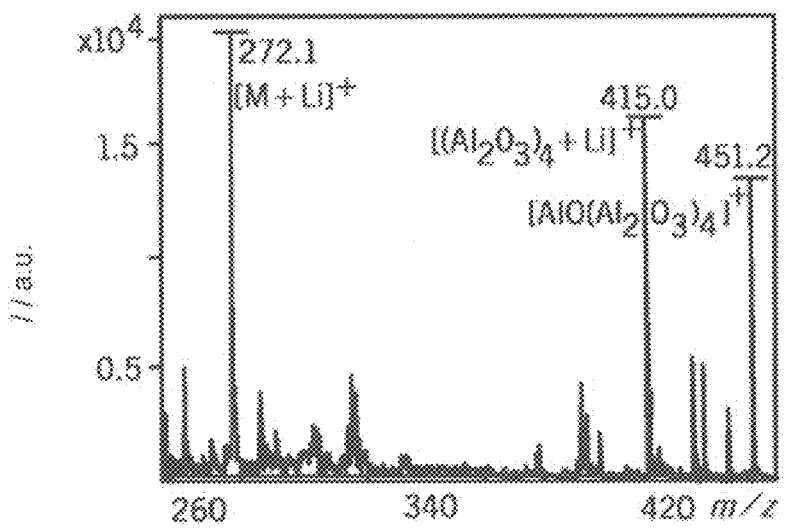

FIG. 9C shows TOF mass spectrum of mannose with PCL grafted on an ACG slide formed by cathode arc evaporation at the m/z region of interest. More specifically, FIG. 9C shows the MS data of the ACG slide produced by cathode arc evaporation, for which the surface-activation conditions were optimized and the peak intensity of the mannose derivative was high. Although the substrates gave large background peaks at m/z 415 and 451 (FIGS. 9A and 9C), the molecular weight of the mannose derivative (265) was detected quite easily by its adducts with proton (m/z 266), lithium (m/z 272), sodium (m/z 288), and sometimes potassium (m/z 304) ions.

It is theorized that under high vacuum, UV excimer laser energy vaporizes aluminum oxide clusters to the gas phase; ultraviolet photon ionization produces sparse mass spectra with relatively light aluminum oxide clusters. The majority of the oxide clusters in the gas phase under vacuum consisted of $AlO(Al_2O_3)_n$, even though the aluminum oxide clusters could exist in many different forms. In FIGS. 9A and 9C, the large background peaks that occurred at m/z 451 and 415 are speculated to belong to the oxide clusters $[(Al_2O_3)_4+Li]^+$ and $[AlO(Al_2O_3)_4]^+$.

Figure 10A:
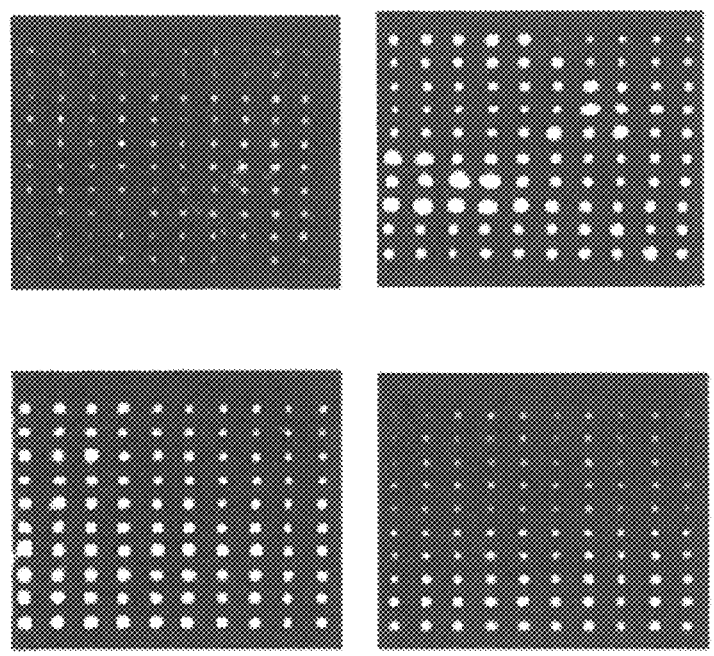
FIG. 10A-FIG. 10C show implementations of protein-binding assays of ACG slides formed by cathode arc evaporation upon treatment with a) oxygen plasma (Al-1), b) argon plasma (Al-2), and c) a mixture of oxygen and argon plasma (Al-3) prior to APDMES grafting.
Figure 10B:
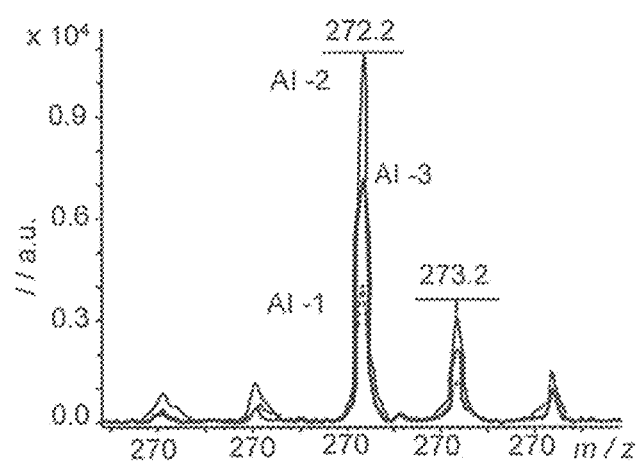
Figure 10C:
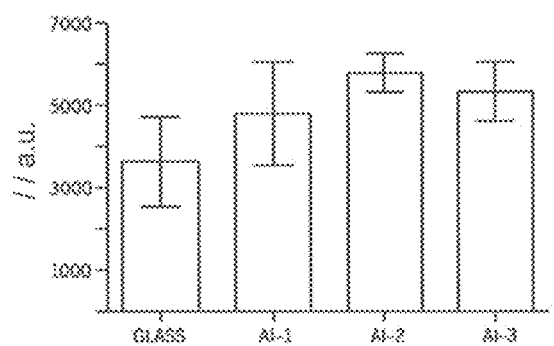

Example 5: Semiquantitative Comparison of the Content of Mannose with its Protein-Binding Capability The optimization of the plasma gas treatment on the same type of ACG slide was evaluated by the fluorescence intensity of the immobilized sugar-protein binding. FIG. 10 was obtained by selecting the type of gas used for plasma cleaning. ACG slides produced by cathode arc evaporation were exposed to oxygen, argon, or a mixture of oxygen and Argon plasma gases prior to aminosilane grafting. A 10×10 block (100 spots) of the mannose derivative (sugar complex solution, 160 mm) was microarrayed onto the substrate surfaces. The sugar complex solution was also manually spotted on each of these slides (1 mL per spot) specifically for mass identification. Therefore, these slides were analyzed first by mass spectrometry and then subjected to biotinylated ConA binding followed by Cy3-tagged streptavidin detection. FIG. 10A a)-d) shows the protein-binding assays of the arrayed slides; FIG. 10C shows the fluorescence intensities of substrates versus those of the commercially available glass slide. The intensity difference shown in FIG. 5 demonstrates the absolute effect of the physical properties of the substrate. The intensity difference in FIG. 10C resulted from the effects of both the physical properties of the specific substrates and the binding-site architectures between the immobilized sugar and its binding proteins. Both sets of data indicate that argon plasma treatment of the ACG slide surface produced the best substrate for mannose grafting, hence the mannose-protein binding.

FIG. 10A shows protein-binding assays of ACG slides formed by cathode arc evaporation upon treatment with a) oxygen plasma (Al-1), b) argon plasma (Al-2), and c) a mixture of oxygen and argon plasma (Al-3) prior to APDMES grafting. In d), protein-binding assay of the commercially available NH$_2$-glass slide from Corning Glass (#40004) are shown. FIG. 10B shows the signal intensities from MALDI mass spectra for the mass identification of sugar. The maximum-intensity spectra (70% fluence) observed from each substance was used to create the spectra of FIG. 10B. FIG. 10C shows fluorescence intensities of a)-d) with standard errors calculated with an array WoRx fluorescence spectrometer. The array was made in four blocks per slide with 10×10 (100) spots per block of the same aqueous solution of sugar complex. Only the best block from each slide was chosen (as shown in b)-d)); large spots among the best blocks were eliminated for fluorescence-intensity calculations.

Figure 12A:
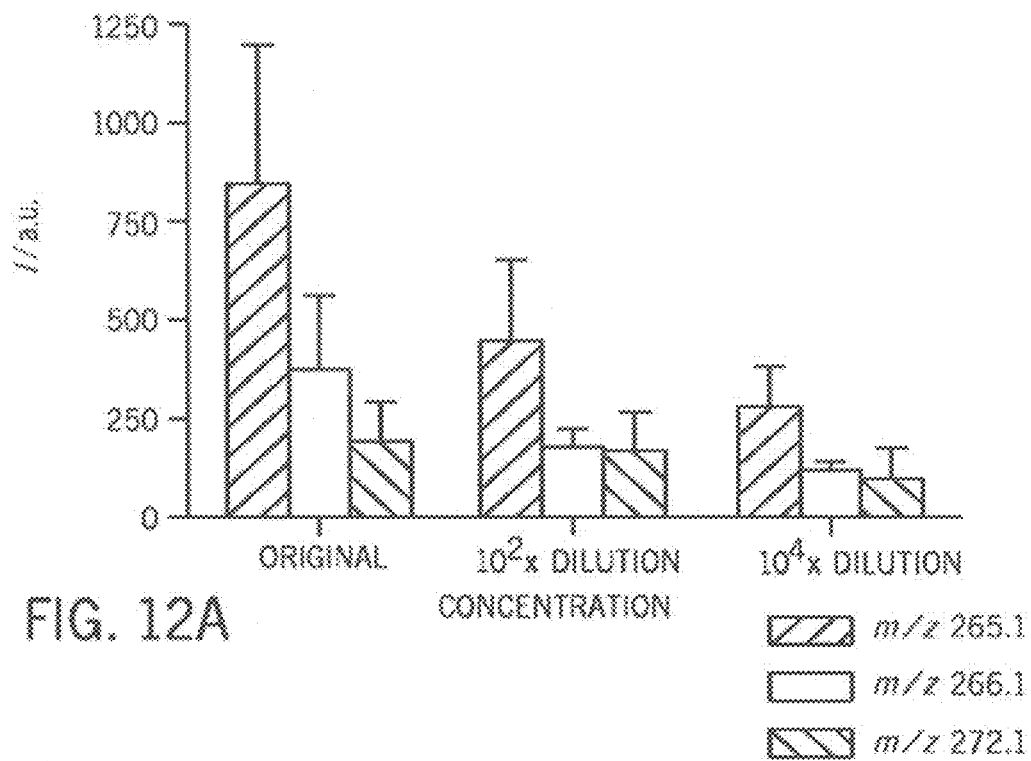
FIG. 12A-FIG. 12B are graphs of implementations of experimental data showing comparison of the peak intensities of the ultraflex TOF mass spectra of mannose with a photo cleavable linker (PCL) grafted on ACG slides with the fluorescence intensities of mannose-protein-bound ACG slide formed by thermal coating followed by electrochemical anodization on the slide surface.
Figure 12B:
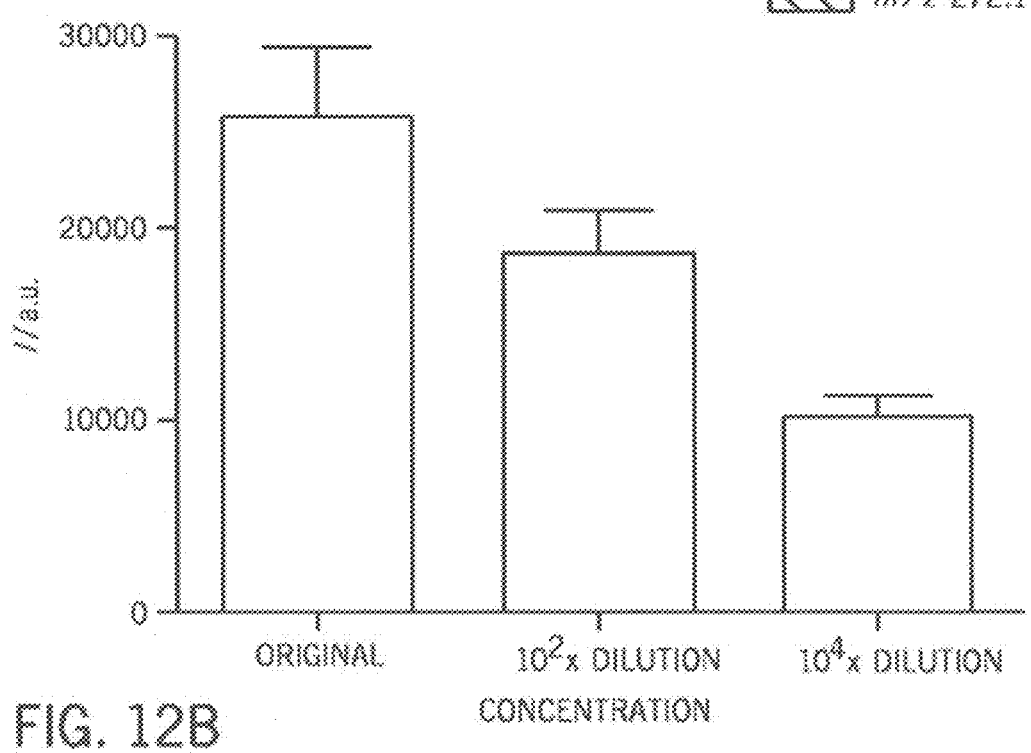

A semiquantitative comparison of the content of the immobilized mannose and the mannose-protein binding capability are given in FIGS. 11 and 12. Two different types of slide substrates were used for immobilizing mannose with the built-in PCL, that is, the $NH_2$ functionalized glass slide and the APDMES-activated $NH_2$-ACG slides that were thermally coated with aluminum followed by surface-anodization treatment. The mannose-ACG slide was first subjected to MS analysis for molecular-weight identification and then to protein-binding evaluation along with the mannose-glass slide. FIG. 11 shows the protein-binding data resulting from the two different types of slide substrates. It clearly indicates that the mannose-ACG slide (FIG. 11b)) showed higher fluorescence of Cy3 with a better sensitivity than the glass slide (FIG. 11a)). The fluorescence intensity from the ACG slide was calculated and is given in FIG. 12B.

The differences in fluorescence intensity in FIG. 11 were caused by the difference in physical properties of the slide substrates and the difference in the degree of mannose-ConA and Cy3-streptavidin binding. This difference in turn, implies a variation in the grafting density of mannose on the substrate surface. A recent report indicated that the interaction between ConA and mannose becomes weak when the density of mannose on the substrate surface is about 100 Å apart, thus reflecting the degree of polyvalent interaction.

MS analysis of the same mannose-ACG slide (FIG. 11b)) revealed the parent peak (m/z 265) as well as the proton (m/z 266) and lithium (m/z 272) adducts. In analyzing this slide, each manually spotted (in the series of dilutions) sample was measured six times with 500 shots per measurement. The average peak intensity with standard deviation is given in FIG. 12A, which demonstrates that MS could still identify the sugar, even when the concentration of the solution for grafting was diluted to 15.6 nm. The signal intensities measured by MS (FIG. 12A) are further compared to the fluorescence intensities shown in FIG. 12B. The descending trends of these two different measurements are similar. Apparently, the quantity of immobilized sugar reflects its protein-binding capability.

FIG. 11 are photographs of implementations of a fluorescence-tagged protein-binding assay of mannose immobilized on a glass slide and an ACG slide. The $NH_2$-functionalized glass slide was purchased from Corning Glass (#40004). The ACG slide was thermally coated with pure aluminum and then electrochemically anodized. The array was made in a block of 10×6 (60) spots. The solution of sugar-HBTU complex (156 mM) was prepared to 100× and 10000× dilution. Each solution was spotted in two columns (20 spots) in the block for grafting. Substrate a) shows fluorescence only in the first two columns (the solution of sugar complex), but substrate b) shows signals up to the sixth column (10000× dilution of the starting solution of sugar complex).

FIG. 12 are graphs of implementations of experimental data showing comparison of the peak intensities of the ultraflex TOF mass spectra of mannose with PCL grafted on ACG slides with the fluorescence intensities of mannose-protein-bound ACG slide formed by thermal coating followed by electrochemical anodization on the slide surface. The concentration of the mannose solution varied from 156 mM to 102 (1.56 mM) and 104× dilution (15.6 nM). In FIG. 12A, average peak intensities of mannose mass spectrometric adducts obtained at m/z 265.1 $[M]^+$, 266.1 $[M+1]+$, and 272.1 $[M+Li]^+$. In FIG. 12B, corresponding fluorescence intensities of the same mannose-ACG slide sample obtained from the fluorescence-tagged protein-binding assay is shown.

Example 6: Utility of ACG Slides on Carbohydrate Microarrays

Figure 13A:
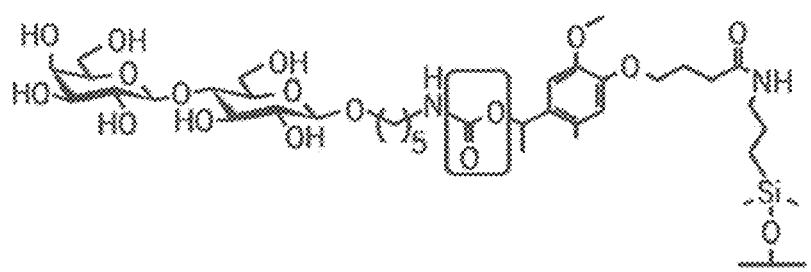
FIG. 13A-FIG. 13E shows data related to implementations of utilization of $NH_2$-ACG surfaces modified through conversion into NHS-ACG by treatment with disuccinimidyl suberate (DSS) in DNIF and diisopropylethylamine.

By using the synthetic route shown in FIG. 2, lactose with PCL was also immobilized on an ACG slide, as shown in FIG. 13A. As seen in the MS analysis of this sample (FIG. 13B), the interference occurred resulting from the sparse aluminum oxide peaks at 415 and 451. However, the molecular weight of the lactose derivative (m/z 427) could still be clearly identified by its adducts with proton (m/z 428), sodium (m/z 450), and potassium (m/z 466) ions.

For further utilization of this newly fabricated substrate, the $NH_2$-ACG surface was modified through conversion into NHS-ACG by treatment with disuccinimidyl suberate (DSS) in DMF and diisopropylethylamine. With glass slides as reference, a Globo H derivative with an amine functional group was arrayed on the NHS-ACG slide (FIG. 13C) and subjected to VK9 (a mouse IgG anti-Globo H monoclonal antibody) protein-binding evaluation. The results in FIGS. 13D and 13E indicate that the ACG slide shows the highest fluorescence intensity among all three samples.

Figure 13B:
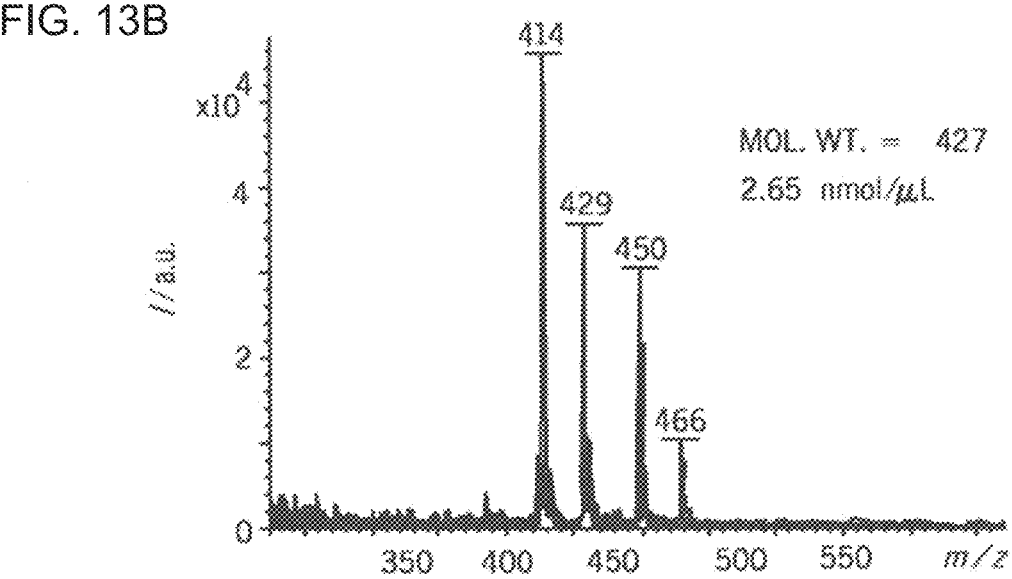
Figure 13C:
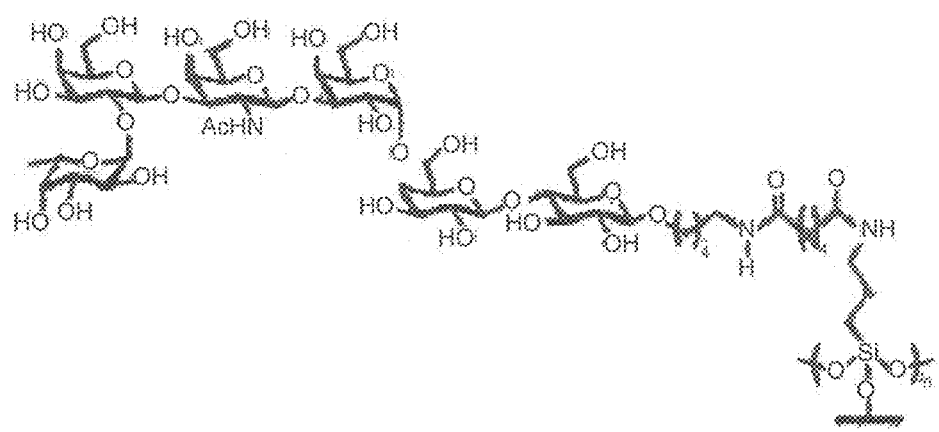
Figure 13D:
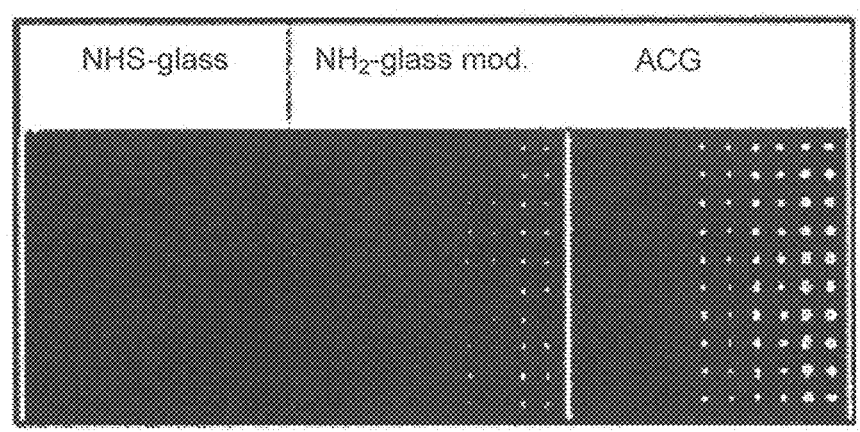
Figure 13E:
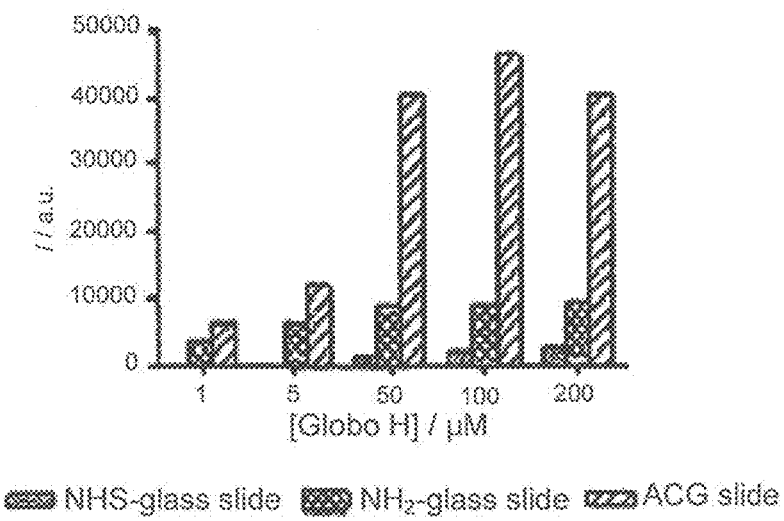

FIG. 13A shows Lactose-ACG slide with PCL. FIG. 13B shows Ultraflex TOF mass spectra obtained from the lactose-ACG slide with PCL. FIG. 13C shows Globo H-ACG slide with no PCL. FIG. 13D shows fluorescence-tagged protein-binding assay of Globo H immobilized on NETS-glass slide, $NH_2$-modified glass slide (Corning #40004), and NHS-ACG slide. Finally, FIG. 13E shows corresponding fluorescence intensities calculated from FIG. 13D with a GenePix 4000 fluorescence scanner.

Example 7: Factors Affecting Fluorescence Intensity-Substrate Property and Surface Morphology The optical properties of substrates apparently affect the fluorescence intensity. Fluorescence (Cy3) is the sole light source in a protein-binding assay. Glass as well as porous silicon both pass and reflect light to different extents. On the contrary, aluminum-coated glass can be fabricated such that it becomes completely nontransparent and minimizes the "waste" of light provided by the light source.

The surface morphology of the substrate could affect the grafting density in immobilizing sugars. The NAO surface showed only 75% oxide content. On the contrary, the AAO surface contains 100% aluminum oxide, thus providing a stable surface and leading to a steady immobilizing density of the final slide for assay.

Substrate stability may also be affected by the way in which the surface is chemically treated. An example is the surface with cross-linked amines versus that with a monolayer of amine functional groups, both of which were made by activating the ACG slide with either 3-aminopropyltriethoxysilane (APTES) or 3-aminopropyldimethylethoxysilane (APDMES). Various chemical treatments of the ACG slide surface are under investigation.

Example 8: Factors Affecting Fluorescence Intensity-Binding-Site Architectures/Interactions of Proteins with Sugars Immobilized on the Substrate Surface Under our experimental conditions, both concanavalin A and streptavidin exist as tetramers of their quaternary structures. The ratio of the dimensions of mannose to ConA is about 1:400 (corresponding to their molecular weight of 265 vs. 104 kDa). Owing to the geometric constraint, only two binding sites per tetramer of biotinylated ConA are available for mannose binding on the surface. On the high-density mannose array surface, each ConA tetramer would bind two molecules of mannose, and the two mannose molecules would probably be grafted on the surface not too far away from each other. As the chain length of the mannose derivative increases, the grafted mannose becomes further away from the substrate, and a high degree of randomness of the interaction could occur when both the grafting density and the amount of immobilized sugar-protein binding increase. Furthermore, the flexible docking of the streptavidin-Cy3 complex to biotinylated ConA was allowed. A similar geometric restriction can also be illustrated for Globo H, IgG monoclonal antibody VK9 (from mouse), and its goat anti-mouse IgG protein. The binding-site architecture between sugar and proteins could affect the density of the fluorescence-tagged protein and, thus, the fluorescence intensity in the sugar-protein-binding assay.

One purpose of studying the surface immobilization of sugars is to mimic the ligand interactions that occur on the cell surface of biological entities, for example, the existence and overexpression of the sugar antigen Globo H on the surfaces of normal and malignant cells. The sugar antigens, when overly populated on the cell surfaces, could result in massive polyvalent carbohydrate-protein interactions and greatly impact the provided biological function of the living entities. This study provides a more precise quantitative measurement and comparison of such a biological system.

Example 9: Preparation of PTFE-Like ACG Slides

To prepare the PTFE-like ACG slides, triethoxysilane 1 and phosphonic acid derivatives 3 were synthesized and used for reaction with the oxidized aluminum surface. Fabrication of silane based slide involves a two-step chemical reaction. The first step was to functionalize the aluminum oxide surface to amino groups by using compound 1 (FIG. 14) as a grafting reagent. This step was conducted under a moisture-free environment to avoid side reactions. In the second step, amide bond formation took place between NHS activated polyfluoro hydrocarbon compound 2 (FIG. 14) and the amino group on the surface of the slide. On the contrary, the phosphonic acid based PTFE-like ACG slide was made in a one-step chemical reaction. An aqueous solution of 3 was reacted by sonication with the cleaned aluminum oxide surface to form a monolayer of perfluorophosphonate covalently bonded onto the surface. The covalent bond formation of phosphonic acid can be confirmed by FTIR and contact angle, as shown in FIG. 28B. These two types of slides were checked with MS-TOF spectrometry for background test, and both showed a clean baseline of the slide background. The unwanted sparse aluminum oxide peaks observed in our previous ACG slides were not seen with this method (see FIGS. 26 and 27).

As illustrated in FIG. 28A, FTIR spectrum of Pure Compound 3 (HDFDPA, 3,3,4,4,5,5,6,6,7,7,8,8,9,9,10,10, 10-heptadecafluorodecylphosphonic acid) and an FTIR spectrum of ACG surface grafted compound 3. FIG. 28B illustrates the water Contact Angle ($\cong 120°$) image of the phosphonated ACG slide surface.

Figure 14:
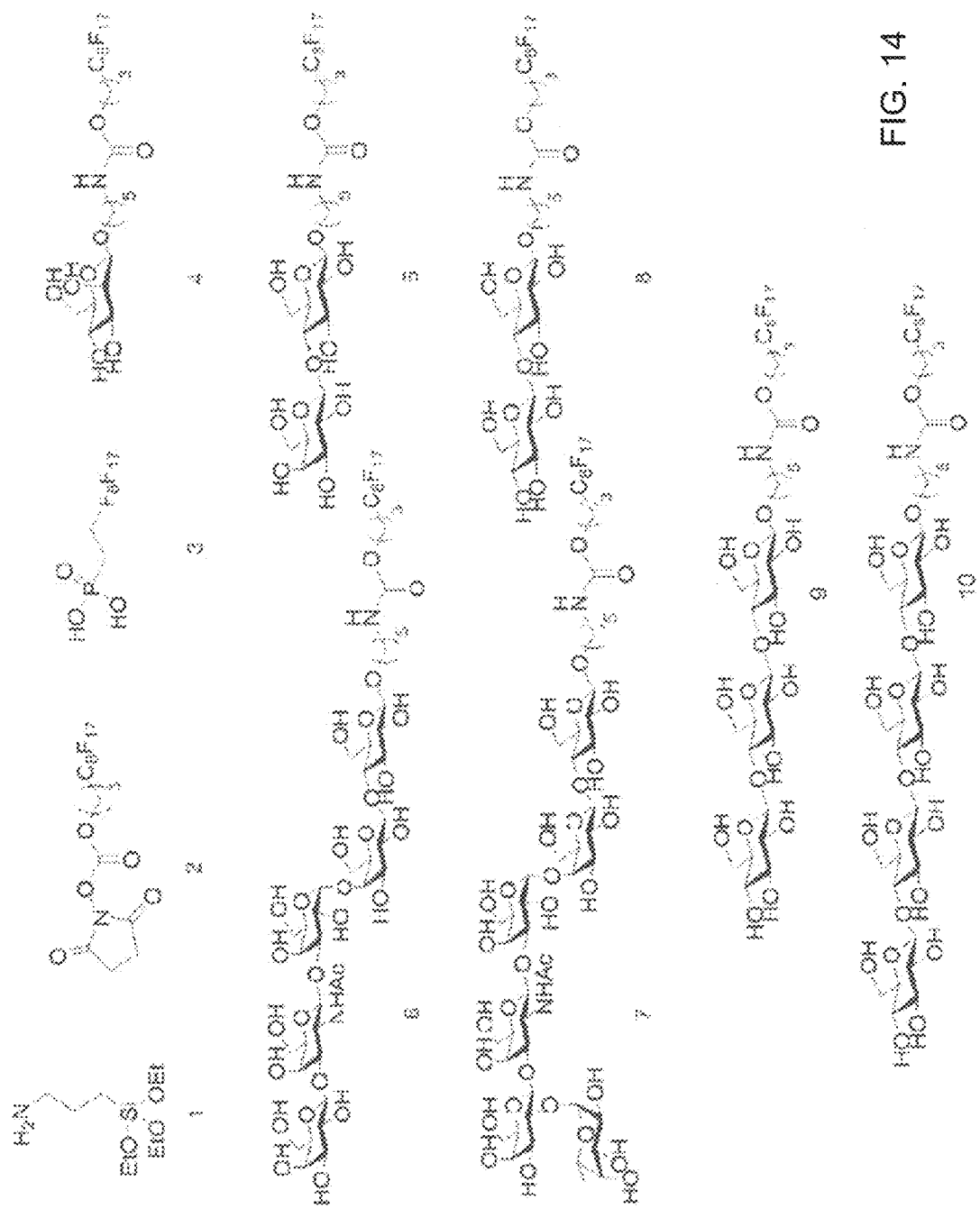
FIG. 14 are chemical formulae of structures of compounds used in ACG-mass spectroscopy experiments.

As shown in FIG. 14, the compounds are as follows: aminopropyltriethoxysilane (APTES, 1); N-Succinimidyl 4,4,5,5,6,6,7,7,8,8,9,9,10,10,-11,11,11-heptadecafluoroundecyl carbonate 2; (3,3,4,4,5,5,6,6,7,7,8,8,9,9,10,10,10-heptadecafluorodecyl) phosphonic Acid (HDFDPA, 3), 4 to 10 are poly-fluorinated derivatives of mannose (4), lactose (5), Gb5 (6), Globo H (7), cellobiose (8), cellolotriose (9) and cellotetraose (10).

Figure 16:
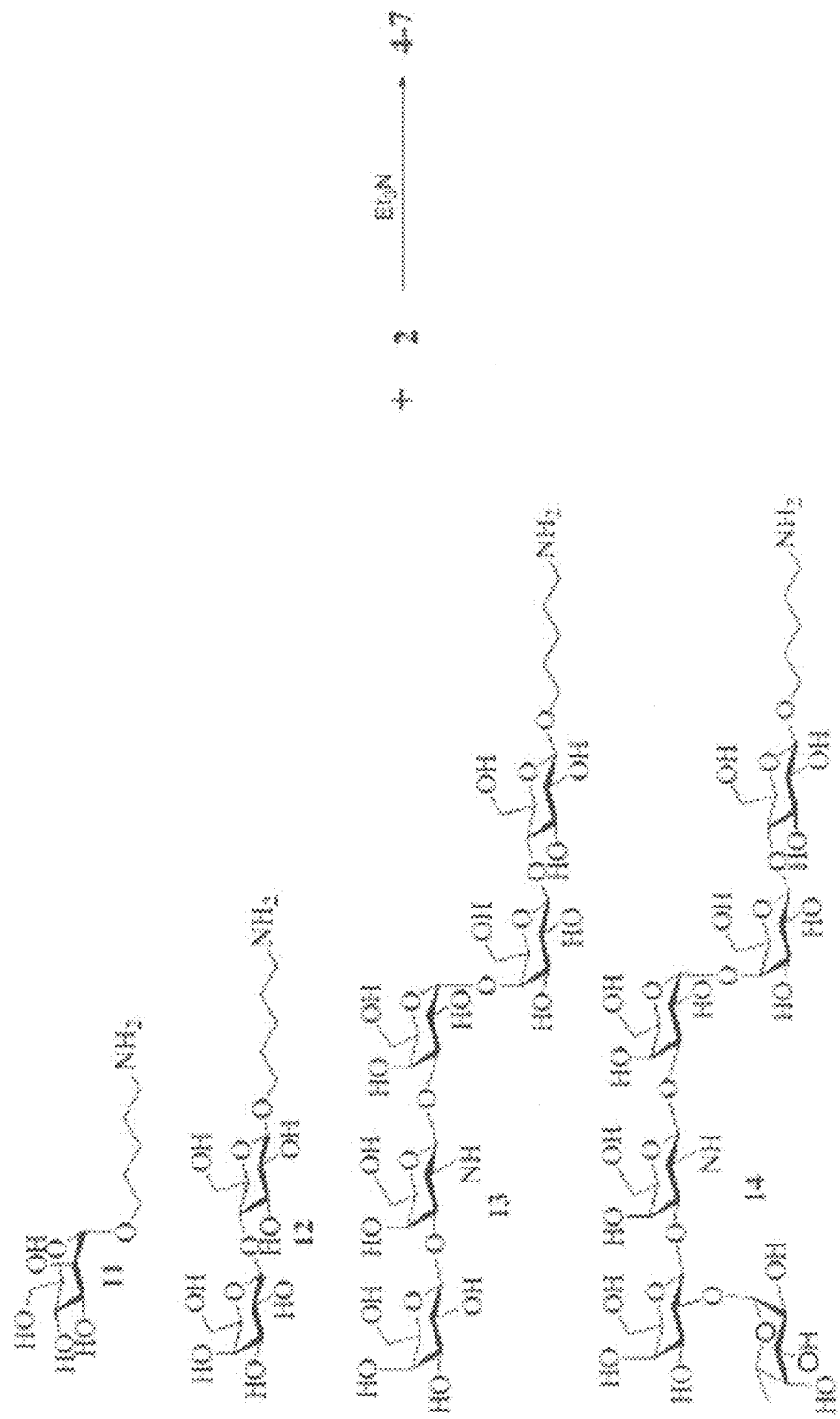
FIG. 16 is a scheme illustrating the synthesis of implementations of poly-fluorinated carbohydrates 4-7.

Example 10: Creation of Non-Covalent Bond Glycan Array on the PTFE-Like ACG Slides With this encouraging result, the phosphoric acid based slide was used to create the glycan array for the experimental procedures outlined in FIG. 15. Mannose with an amino linker 11 was reacted with compound 2 to synthesize the poly-fluorinated ($—C_8F_{17}$) tail 4 and used as the model compound, as illustrated by the scheme shown in FIG. 16. A solution of this sugar derivative was spotted robotically onto the PTFE-like ACG slide surface. After incubation, the slides were rinsed repeatedly with distilled water and subjected to MS-TOF analysis. A very clean mass spectrum was obtained. The mass spectrum of this monolayer reveals peaks at 806 and 822 for the sodium and potassium adducts, respectively. Following the MS analysis, the same slide was used for protein binding analysis by using Alexa 488-labeled Concanavalin A as a protein source. To further extend the scope of this type of glycan array, use of the compounds 12-14 that were synthesized by our laboratory previously as the starting materials. Poly-fluorinated Gb5 5, lactose 6 and Globo H 7 were synthesized, as illustrated in FIG. 16 and immobilized them onto the PTFE-like ACG slide surface for both mass analysis and protein binding assays according to the methods disclosed herein.

Figure 17A:
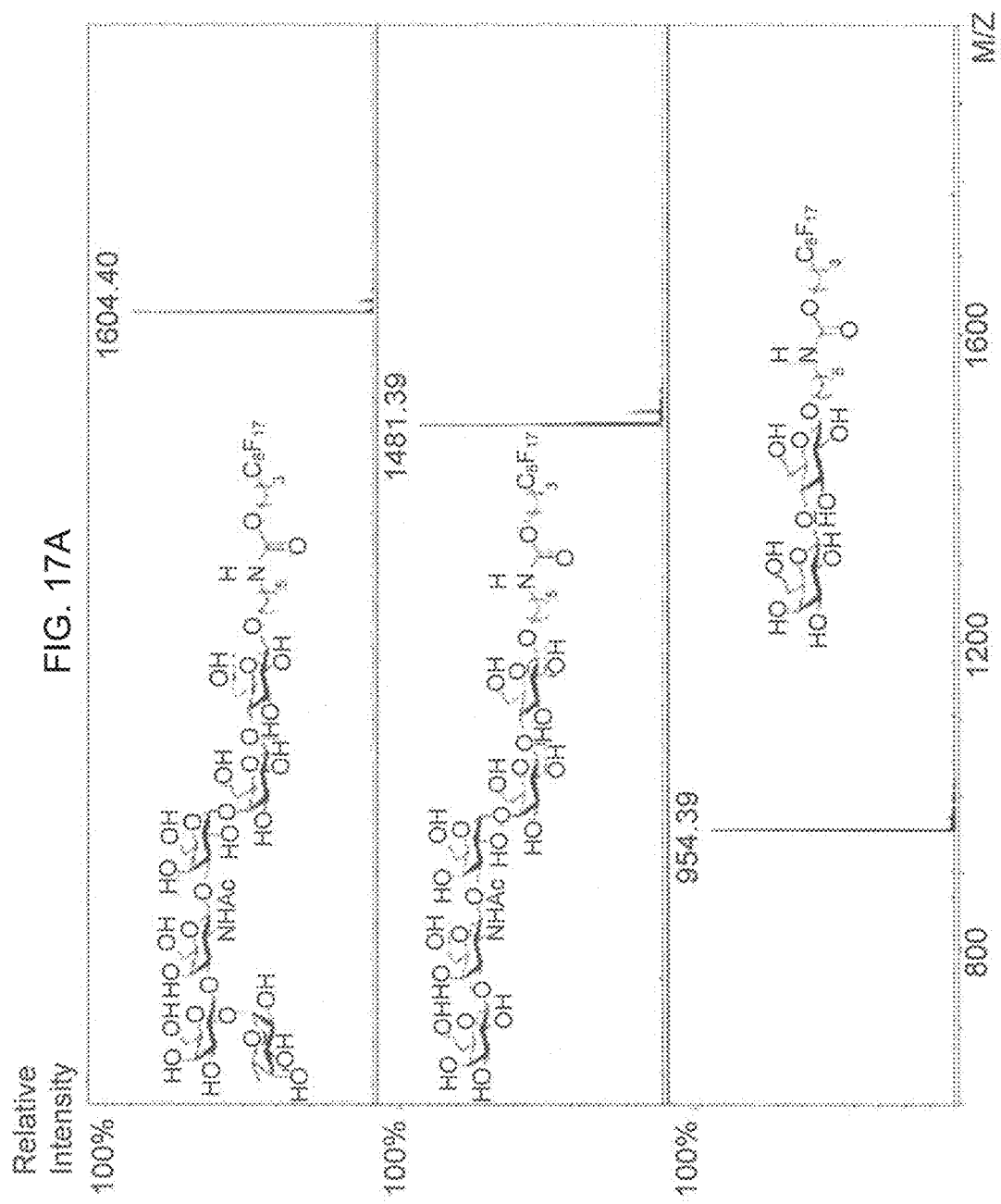
FIG. 17A-FIG. 17C are representations of implementations of experimental data using the PTFE-like ACG slides having poly-fluorinated carbohydrates bound to them.

As shown in experimental implementations illustrated by the data shown in FIG. 17A, without adding additional matrix, no fragmented signal was found, even with the use of such labile sugar as Globo-H. FIG. 17A illustrates MALDI mass spectrometric analysis data of polyfluorinated Globo H 7 (MW. 1604.40), Gb5 5 (MW. 1458.39) and lactose 6 (MW. 932.21) immobilized on PTFE-like ACG slide as their sodium adducts $[M+Na]^+$ at 1627.44, 1481.39, and 954.39, respectively. The fluence rate is 12% without matrix addition.

Figure 17C:
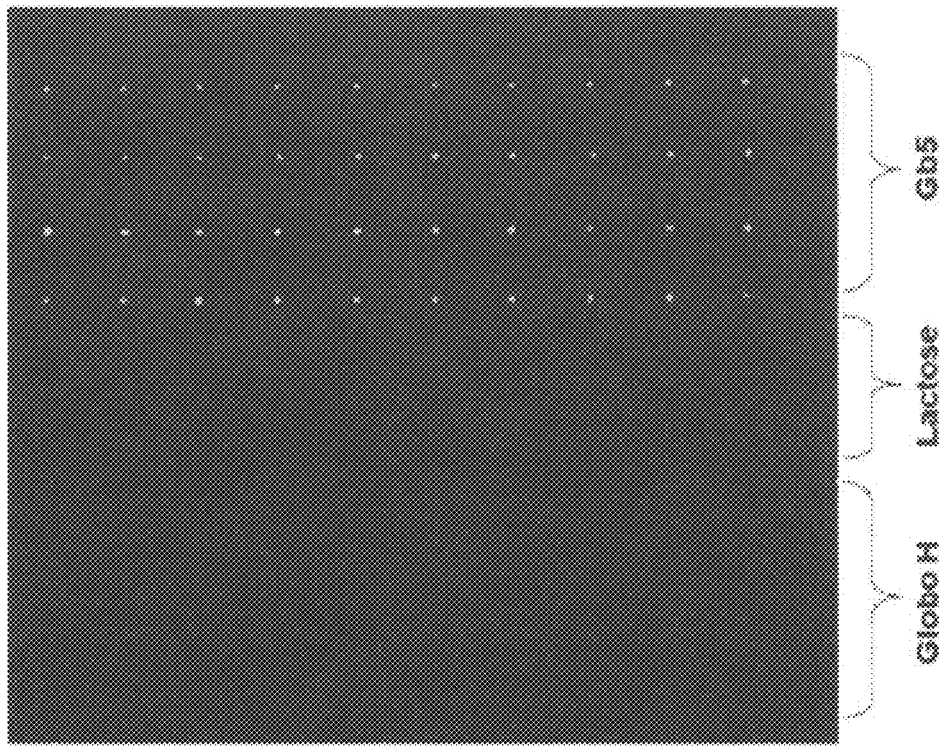
Figure 17B:
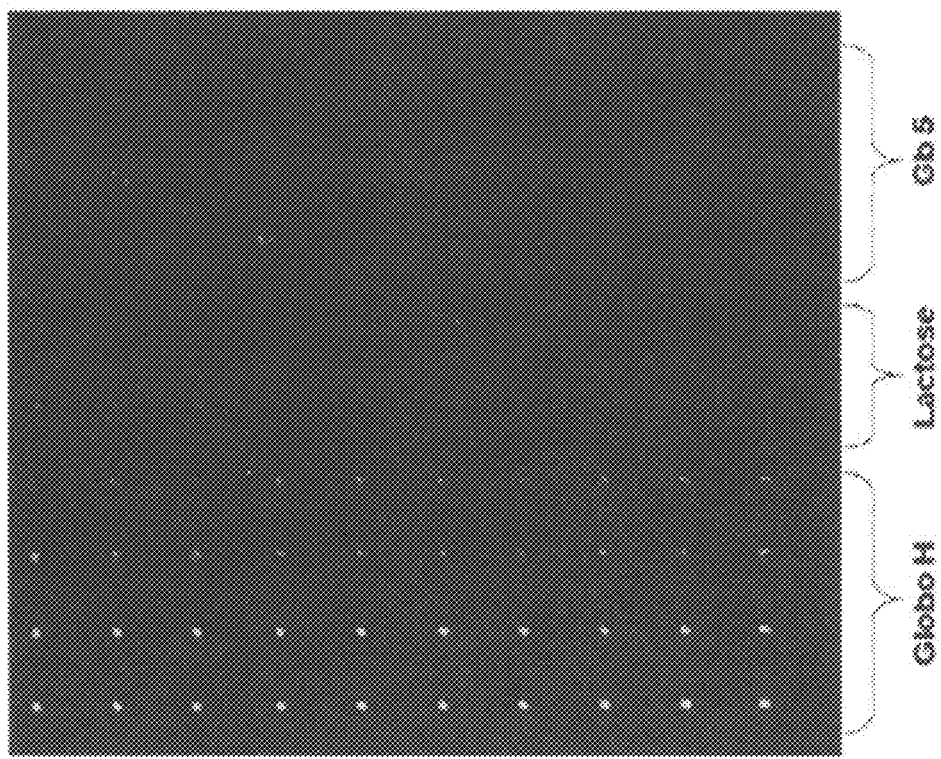

According to implementations of experimental data in FIG. 17B, these glycan arrays retained their sugar-protein binding patterns. FIG. 17B is a protein-binding assay of GloboH/VK9/anti-VK9-Cy3. FIG. 17C is a protein-binding assay of Gb5/anti-SSEA3-A488. The matrix was a 10×10 (100 spots) array of perfluorinated Globo H (left 4 columns), lactose ($5^{th}$ & $6^{th}$ columns, served as the negative control), and Gb5 (right 4 columns).

Figure 18:
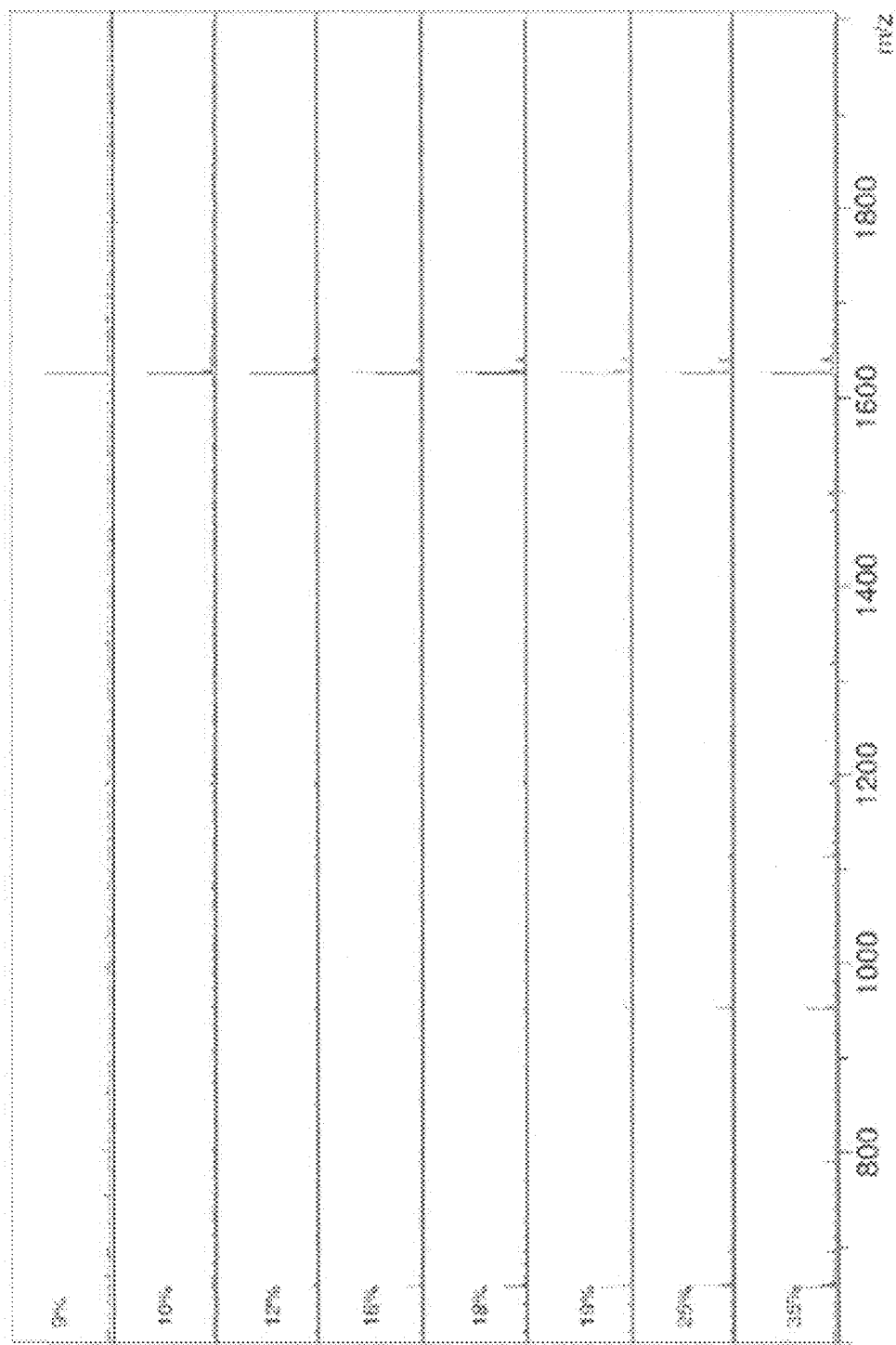
FIG. 18 are graphs of implementations of experimental data of mass spectra of Globo H on ACG slide by using different laser fluence rate without matrix addition.

The effect of laser fluence rate and matrix on this new surface was also investigated. Taking the labile carbohydrate Globo H as an example, it often loses a fucose moiety when used in MALDI-MS. By using mass spectrometry as a detector, the results were showed in table 1. Without adding matrix, a high signal to noise (S/N) ratio (22) in very low laser fluence rate (9%) is observed, and under this low laser fluence rate, no fragmented signal was found. When the fluence rate increase to 10%, the S/N ratio enhance to 40 without any fragmentation. FIG. 18 illustrates the resulting mass spectroscopy data under various laser fluence conditions without matrix added.

Figure 19:
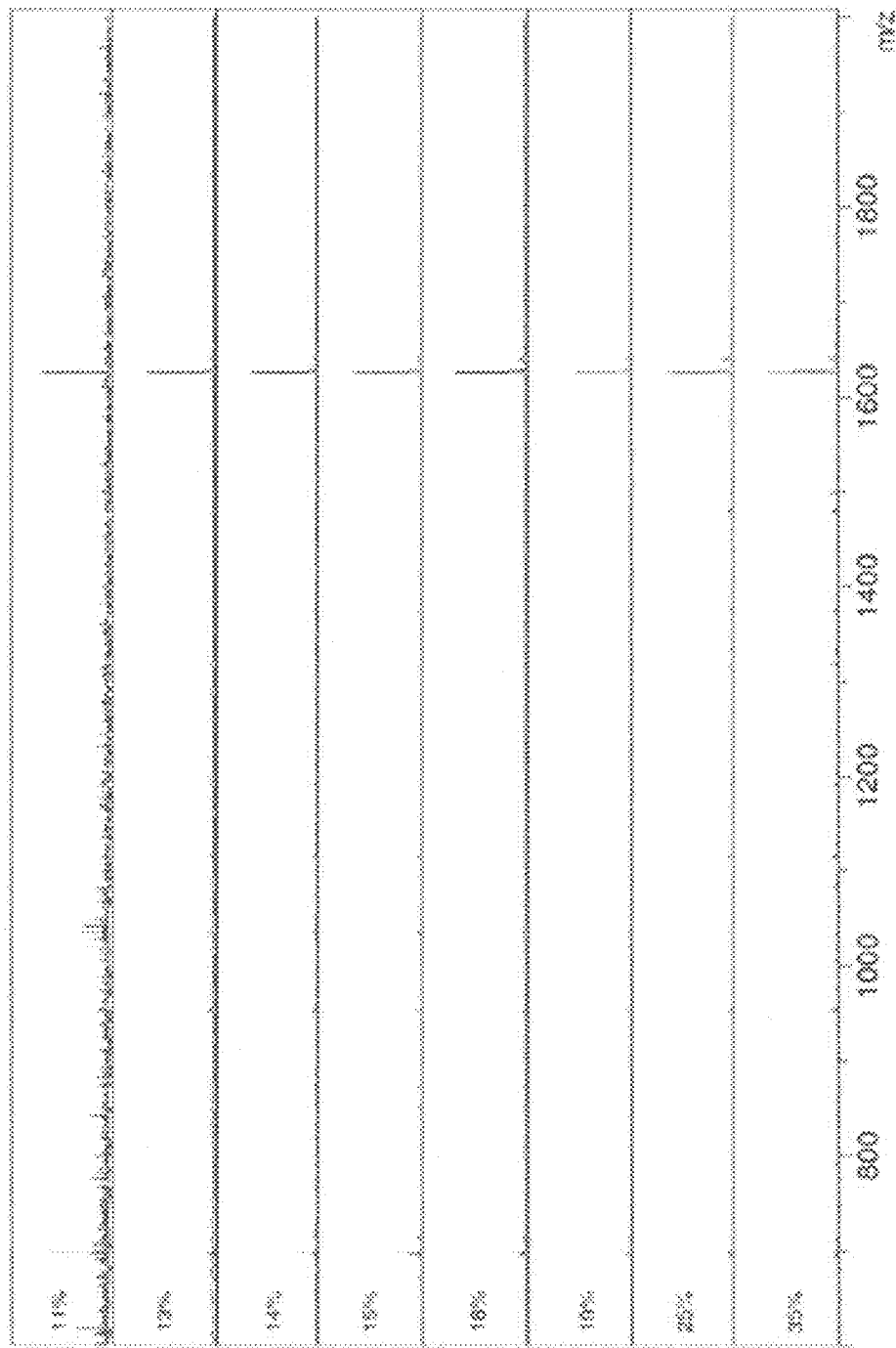
FIG. 19 are graphs of implementations of experimental data of mass spectra of Globo H on ACG slide by using different laser fluence rate with matrix.

FIG. 19 illustrates the same experiments, but with matrix. DHB was added as a matrix to check the matrix effect on the ACG surface. The S/N is only 7.3 when the fluence rate is 11%. To increase the fluence rate to 13%, the S/N is 61% with 6% fragmentation signal. The DHB matrix therefore doesn't enhance the S/N signal when low laser fluence rate be used. However, it can play a role to enhance S/N and reduce the fragmentation when the fluence rate over 25%, as shown in Table 1.

TABLE 1

S/N ratio of Globo H under different laser fluence rate with or without matrix addition. (Fluence: the laser power (or fluence rate) applied on the slide surface; GH S/N: the Signal/Noise ratio for globo H; Frag. S/N: the Signal/Noise ratio for the peak of fragmentation of globo H.)

| Matrix-assisted Desorption/Ionization | | | Matrix-free Desorption/Ionization | | |
|---|---|---|---|---|---|
| Fluence Rate | GH S/N | Frag. S/N | Fluence Rate | GH S/N | Frag. S/N |
| 11% | 7.3 | 0 | 9% | 22 | 0 |
| 13% | 61 | 6 | 10% | 40 | 0 |
| 14% | 157 | 13 | 12% | 218 | 5 |
| 15% | 316 | 25 | 16% | 275 | 10 |
| 18% | 1690 | 87 | 18% | 375 | 17 |
| 19% | 1956 | 108 | 19% | 741 | 64 |
| 25% | 3128 | 168 | 25% | 2184 | 356 |
| 35% | 1445 | 125 | 35% | 1514 | 373 |

Example 11: Cellulase Activity Studies

From the previous studies, poly-fluorinated carbohydrate immobilized on the PTFE-like ACG slide is easily ionized/desorbed by low laser energy. High S/N mass spectrum without fragmentation is therefore obtained, making the devices of the present disclosure suitable for glycosidase specificity and activity studies.

Enzymatic hydrolysis of the immobilized poly-fluorinated cellobiose 8 (see FIG. 14) was first conducted in situ on the phosphonic acid slide surface. Three commercially available cellulases, *Aspergillus niger* (*A. niger*), *Trichoderma reesei* (*T. reesei*), and *Trichoderma viride* (*T. viride*) were prepared separately at 5 U/mL in a sodium acetate (25 mM) buffer solution (pH 5) and loaded onto the functionalized slide which has been divided into 16 wells using Fast Frame reaction chambers. For comparison, an aliquot of enzyme solution (100 μL) was added to the solution of fluorinated cellobiose (100 μL of 0.5 mM) in eppendorfs to carry out the enzymatic hydrolysis reactions in solution. After the reaction, it was transferred to the empty wells of the same slide. Each well was rinsed separately three times with de-ionized water and the slide was dried again under high vacuum before subjecting to MS-TOF analysis.

Figure 20A:
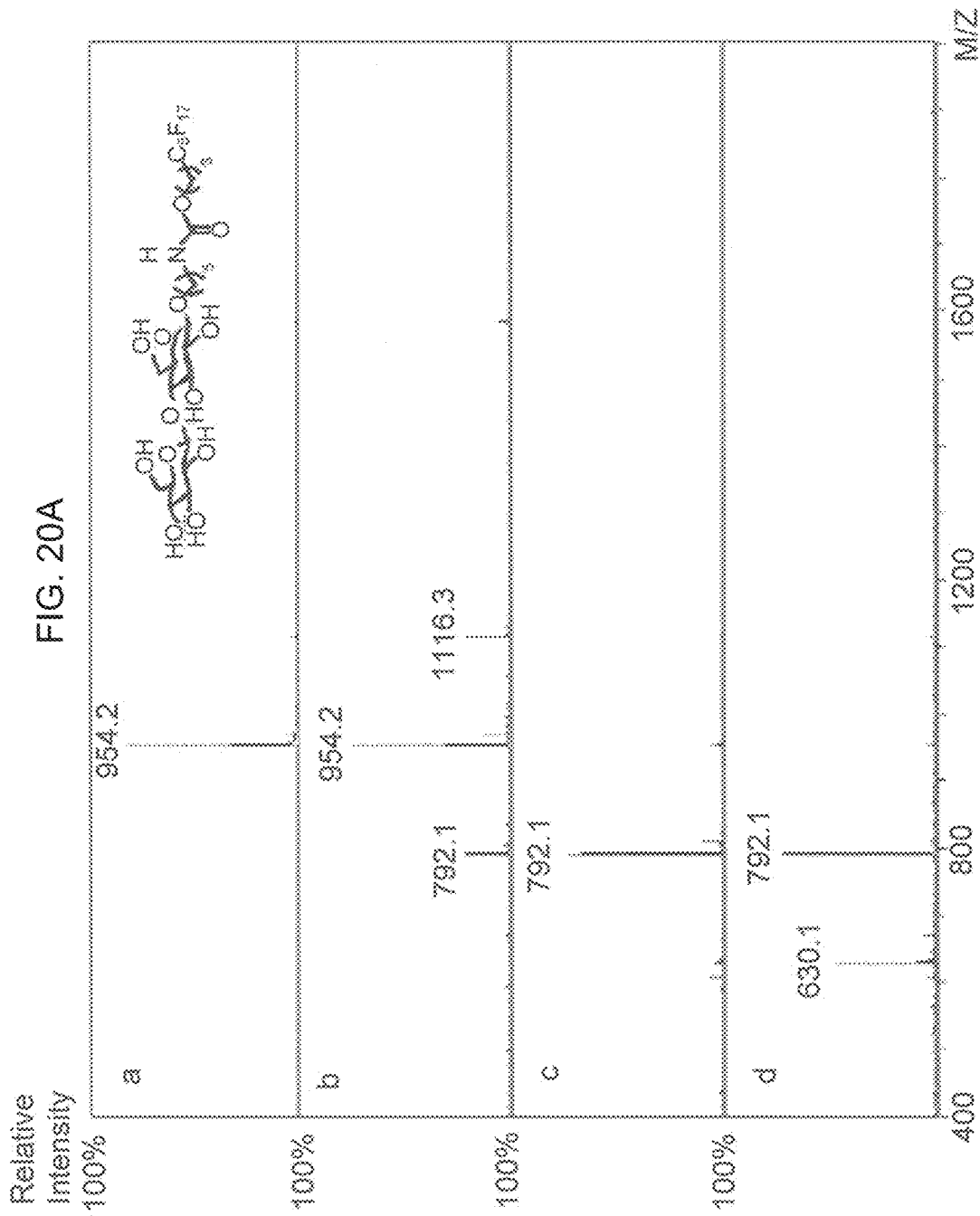
FIG. 20A-FIG. 20B are graphs of implementations of experimental data of MS-TOF data of enzymatic hydrolysis of poly-fluorinated cellobiose in solution and immobilized on PTFE-like ACG slide with the cellulase proteins from *A. niger, T reesei*, and *T. viride*. MS-TOF data of enzymatic hydrolysis of poly-fluorinated cellobiose in solution is shown in FIG. 20A and immobilized on PTFE-like ACG slide is shown in FIG. 20B.

Under MS-TOF analysis, the clean background baseline allowed calculation of the percentage of hydrolyzed components for each sample. As shown in the MS-TOF results in FIG. 20, percentages of hydrolyzed products are calculated from the peak intensities of each spectrum. According to implementations of experimental data shown in FIG. 20, MS-TOF data of enzymatic hydrolysis of poly-fluorinated cellobiose in solution in FIG. 20A and immobilized on PTFE-like ACG slide in FIG. 20B. The control are the same experimental conditions run without enzymes in (a); (b), (c), and (d) are experimental conditions with the cellulase proteins from *A. niger* (b), *T. reesei* (c), and *T. viride* (d).

These results (FIG. 20) show the rate of hydrolysis on the ACG slide surface versus hydrolysis in solution. The un-hydrolyzed cellobiose in solution were 64%, 7%, and 3%, as compared to those of 100%, 69%, and 77% on the ACG slide reacting with the cellulase from *A. niger*, *T. reesei*, and *T. viride*, respectively (Table 2).

TABLE 2

Enzymatic hydrolysis of poly-fluorinated cellobiose 8, the percentage showed hydrolyzed patterns of the reaction in solution/on the ACG slide.

| | Triose | Biose | Glucose | F-tail |
|---|---|---|---|---|
| *A. Niger* | 18/0 | 64/1 | 18/0 | 0/0 |
| *T. Reesei* | 0/0 | 7/69 | 93/25 | 0/7 |
| *T. Viride* | 0/0 | 3/77 | 58/17 | 38/6 |

Figure 21A:
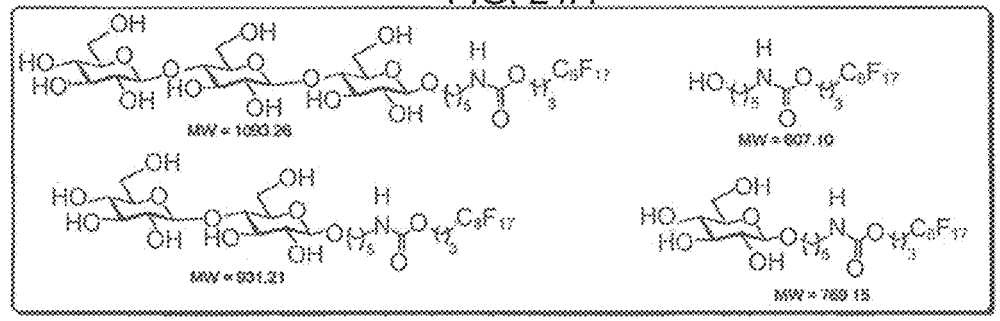
FIG. 21A-FIG. 21B are chemical structures and graphs of implementations of experimental data showing the effect of cellulases on cellotriose.
Figure 21B:
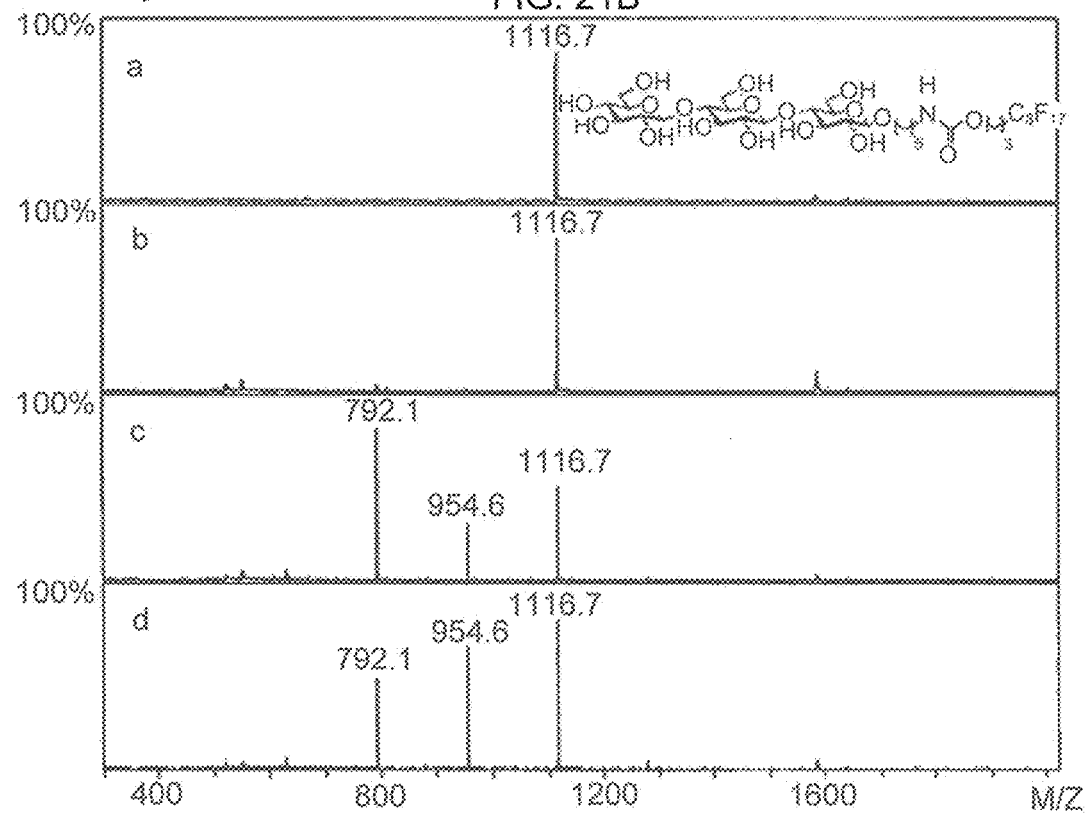

According to implementations of experimental data shown in FIG. 21A, hydrolyzed fragments of cellotriose derivatives remained on the PTFE-like ACG slide surface. FIG. 21A shows the various derivates that are possible, together with their molecular weights. FIG. 21B shows implementations of experimental MS-TOF data of enzymatic hydrolysis of poly-fluorinated cellotriose of the control run without enzymes (a), and with the cellulase proteins from *A. niger* (b), *T. reesei* (c), and *A. viride* (d).

The enzyme from *T. viride* functions the best for cellobiose in solution, and that from *T. reesei* hydrolyzed the disaccharide most effectively among the three enzyme sources on the slide. In solutions, the enzyme from *A. niger* seems to also act as a synthetase that the overall reaction produced 8% of cellotriose (MW 1093) detected as sodium adduct at m/z of 1116.3 $[M+Na]^+$. The enzyme from *A. niger* was characterized as a typical endo-type cellulose which cleaved five glucose units in length at a time. It did not hydrolyze either cellobiose or p-nitrophenyl-ß-D-glucoside. To further understand the mode of action, poly-fluorinated ($-C_8F_{17}$) cellotriose 9 (FIG. 14) was subjected to enzymatic hydrolysis in solution.

Using the same analytical procedure, the results (FIG. 21B) indicated that the enzyme from *T. reesei* hydrolyzed the cellotriose substrate most efficiently among the enzymes from three different species. For *A. niger*, the result shown in FIG. 20 and FIG. 21 indicated that this enzyme does not function well in hydrolyzing cellobiose or cellotriose. However, in solution, it hydrolyzed the poly-fluorinated cellobiose 8, and cellotriose 9 with one glucose unit at a time at a very slow reaction rate. Since this commercial enzyme is not pure, this phenomena may be due to the contamination of a small quantity of ß-glucosidase in the mixture.

The cellulase from *T. viride* could effectively degrade the newspaper material and *T. reesei* could hydrolyze the crystalline form of cellulose. In general, the enzymatic hydrolysis on the ACG slide surface is more site-specific but much slower than that in solution, as indicated by the data shown in FIG. 20.

Example 12: Cellulase Specificity Studies and Define the Cellulase Type by Using Glycan Array Combined with Mass Spectrometry Cellulases are usually divided into several subclasses of isozymes based upon their function: 1,4-ß-glucosidases [EC 3.2.1.74], which cleave cellobiose into individual glucose molecule, exoglucanases (1,4-ß-D-glucan cellobiohydrolase [EC 3.2.1.91]), which cleaves cellobiose units from the end of the cellulose chain, and endoglucanases (1,4-ß-D-glucan glucanohydrolase [EC 3.2.1.6]), which cleave the chain randomly at internal positions, creating new ends for exoglucanases. HPLC analysis of the products of hydrolysis of MUF-glucosides is often used to determine the hydrolytic specificity of these purified enzymes. From the above results, the devices and methods of this disclosure serve as another platform for studying the specificity of various types of cellulases.

To verify, the exoglucanases (L3) and endoglucanase (44A) were prepared according methods well known in the literature with minor modifications. First, enzymatic hydrolysis reactions were conducted in solution with the purified enzymes using substrates 8, 9 and 10. At the completion of the reaction, the solution mixtures were transferred to the PTFE-like ACG slide, and prepared by using the same washing procedures before being subjected to MS-TOF assay.

Figure 22:
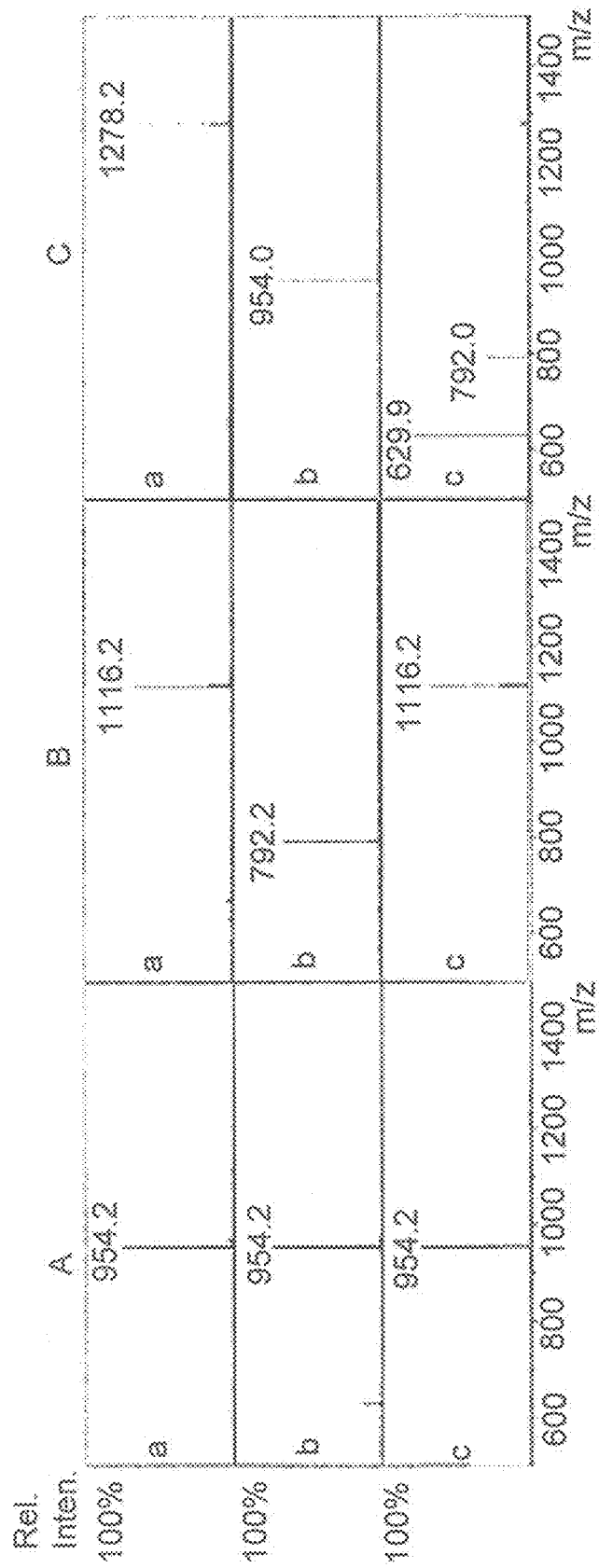
FIG. 22 is a graph of an implementation of experimental MS-TOF data of enzymatic hydrolysis of poly-fluorinated cellobiose (A), poly-fluorinated cellotriose (B) and poly-fluorinated cellotetraose (C) in solution.
Figure 23:
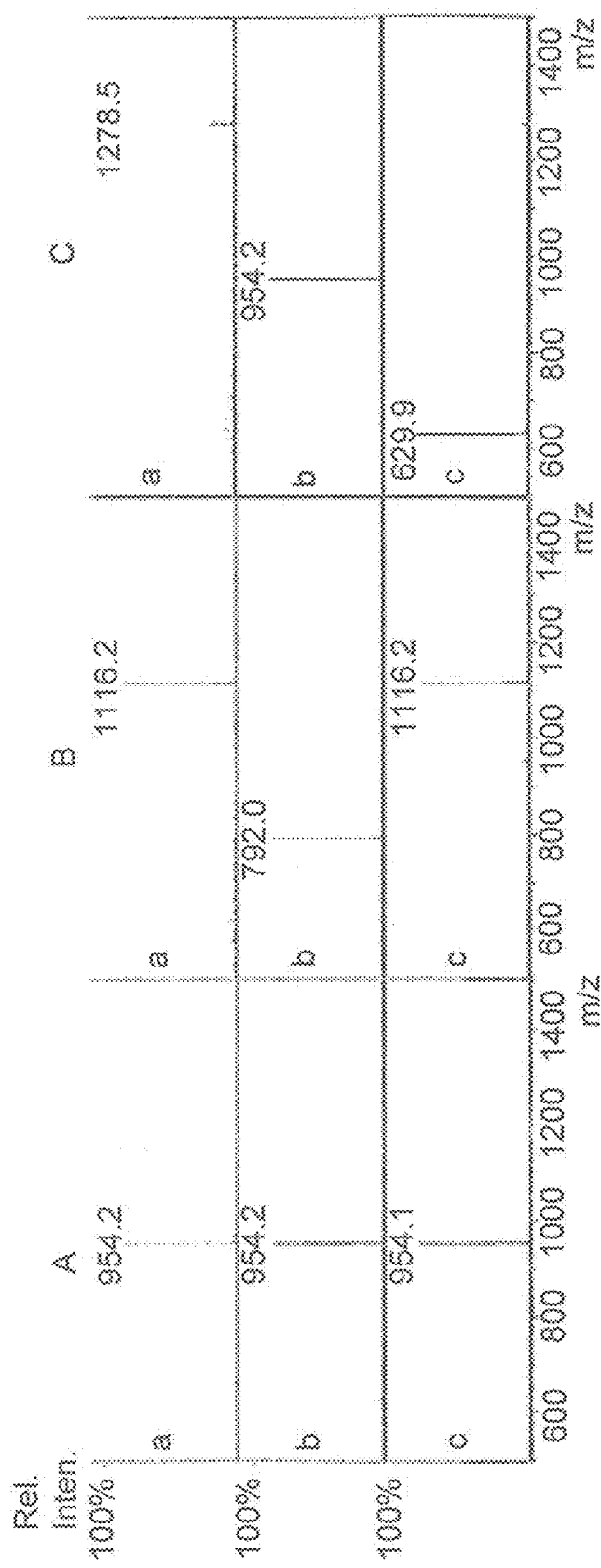
FIG. 23 is a graph of an implementation of experimental MS-TOF data of enzymatic hydrolysis of poly-fluorinated cellobiose (A), poly-fluorinated cellotriose (B) and poly-fluorinated cellotetraose (C) on an ACG glass slide.

FIG. 22 shows MS-TOF data of enzymatic hydrolysis of poly-fluorinated cellobiose (A), poly-fluorinated cellotriose (B) and poly-fluorinated cellotetraose (C) in solution. For each carbohydrate, a specific enzyme was added: (a) is the control run without enzymes, (b) is exoglucanase L3, and (c) is endoglucanase 44A. FIG. 23 shows MS-TOF data of enzymatic hydrolysis of poly-fluorinated cellobiose (A), poly-fluorinated cellotriose (B) and poly-fluorinated cellotetraose (C) on an ACG glass slide. For each carbohydrate, a specific enzyme was added: (a) is the control run without enzymes, (b) is exoglucanase L3, and (c) is endoglucanase 44A.

As shown according to the implementations of experimental data shown in FIG. 22, exoglucanase L3 cleaves cellobiose units slowly from the end of substrate 8 and cleave cellobiose quickly when compound 9 or 10 is the substrate, consistent with the definition of the exoglucanase. Endoglucanase 44A can't accept the cellobiose substrate 8 or cellotriose substrate 9, but cleaves the trisaccharide or tetrasaccharide unit of cellotetraose substrate 10.

Figure 20B:
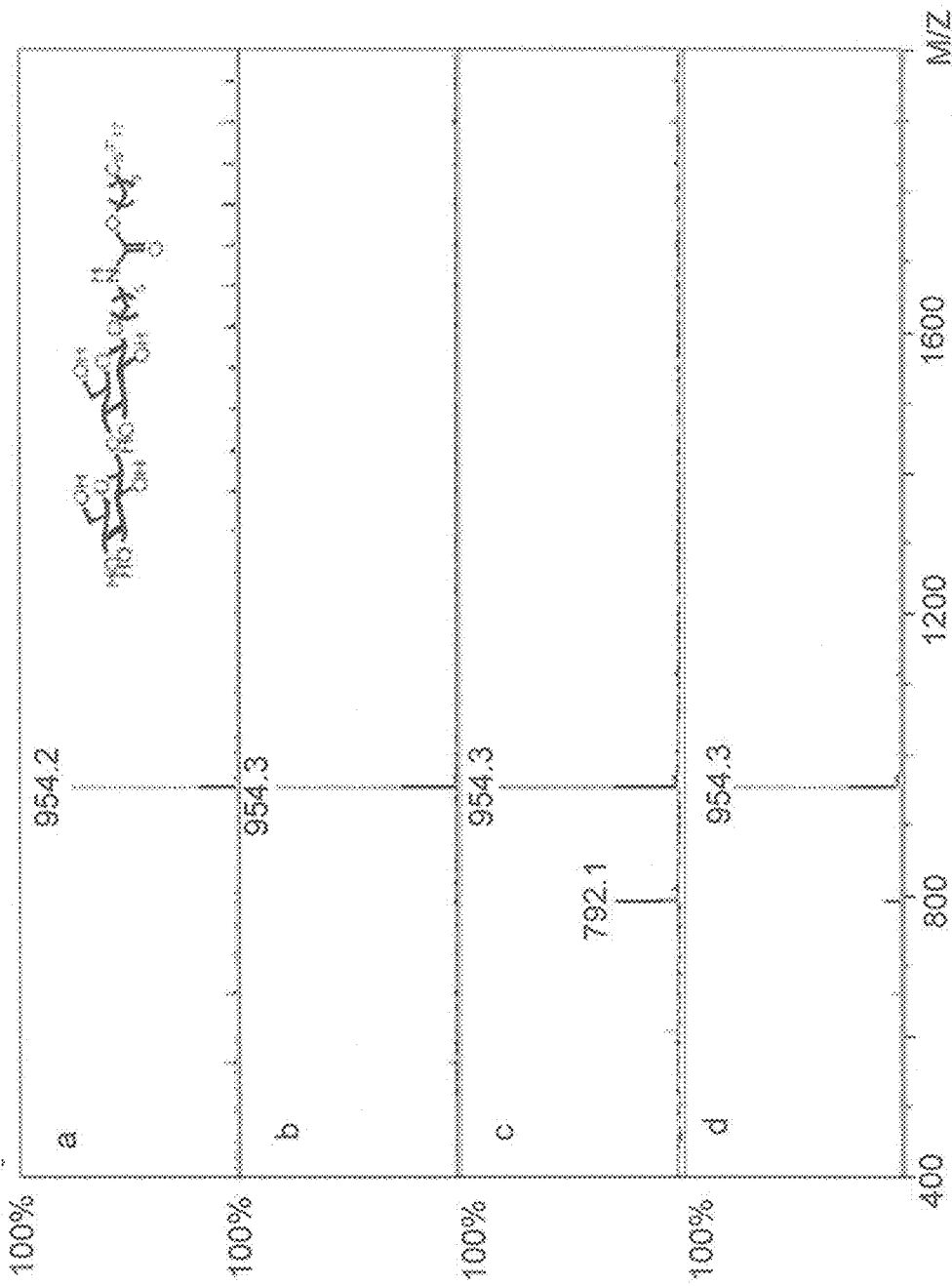

For comparison and as illustrated according to implementations shown in FIG. 23, substrate 8, 9, and 10 were immobilized on the PTFE-like ACG surface and carried out the cellulase hydrolysis on the surface directly, after the same washing procedures, these slides were subjected to MS-TOF assay. As shown in FIG. 20B, exoglucanase L3 only cleaved a fraction of cellobiose substrate 8 after 24 hours of incubation and cleaved the cellobiose quickly when compound 9 or 10 as the substrate. The endoglucanase 44A can't accept compound 8 or 9 as a substrate. However, it cleaved cellotetraose quickly when compound 10 as a substrate. In contrast to the hydrolysis reaction run in solution, endoglucanase 44A cleaved cellotetraose at a time and did not cleave cellotriose when cellotetraose 10 as a substrate. From the above results, the cellotetraose substrate 10 was the best carbohydrate to create array on the PTFE-like ACG surface for the experiments conducted. By using this array, the activity and specificity of unknown cellulase may be examined.

Example 13: Creation of Covalent Bond Glycan Array on PTFE-Like ACG Slides

There are several functionalized glass slides are commercial available for glycan array, for example glass slides coated with: amine, carboxylate, N-hydroxysuccinimide (NHS), avidin, epoxy, aldehyde, chelating nickel group, etc. When creating glycan array on these surfaces, suitable buffer and repeated blocking and washing steps are needed. According to implementations, substrates with a phosphonic acid functional group are easy to chelating on the ACG slide and can tolerate repeated washing steps. Accordingly, a novel method for effective glycan array preparation is hereby disclosed.

Figure 24:
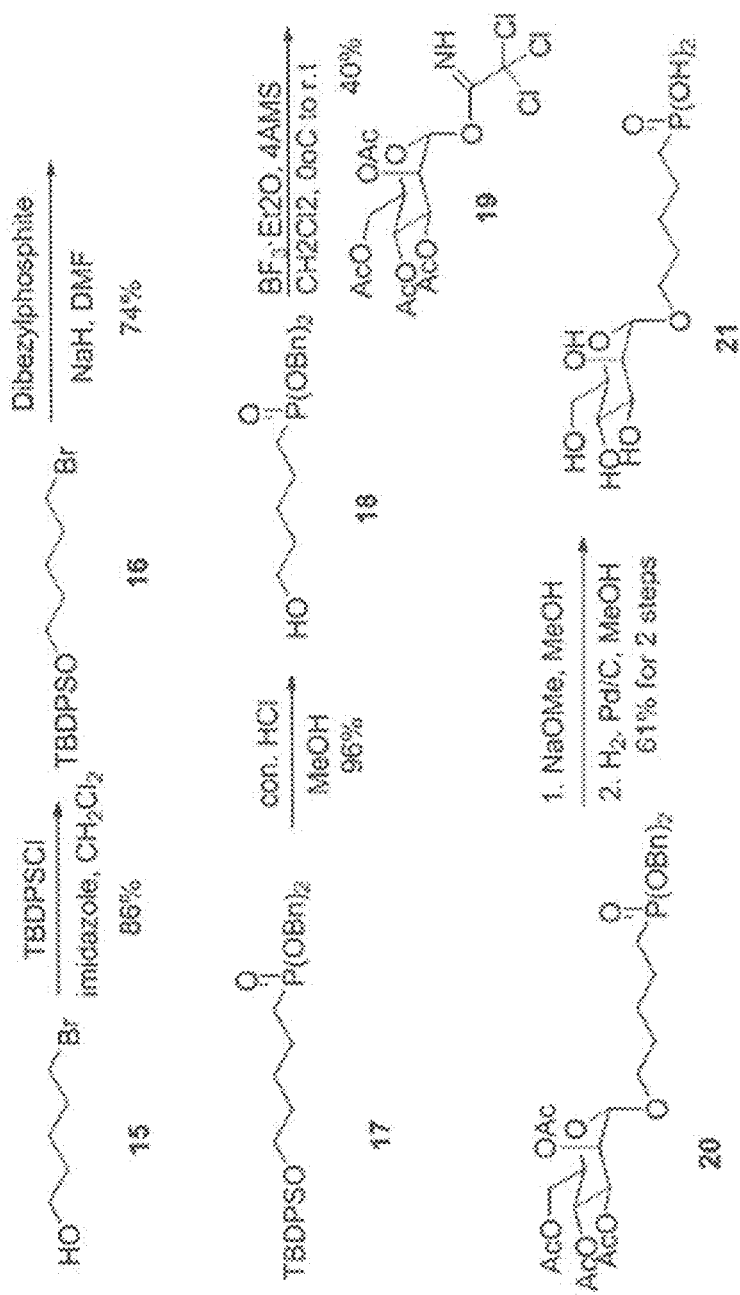
FIG. 24 is a scheme for the synthesis of mannose derivative 21.

Mannose with phosphonic acid compound 21 was synthesized via the scheme illustrated in FIG. 24. Commercial available compound 15 was protected with TBDPS group, and then bromide was changed to phosphonate by using Arbuzov reaction. After desilylation, compound 18 was obtained for the following glycosylation reaction. By using $BF_3.OEt_2$ as a promoter, compound 19 was used as the sugar donor, which yielded mannose molecule with the phosphonate group derivative 20. After global deprotection, mannose with a phosphonic acid compound 21 was obtained.

Figure 25:
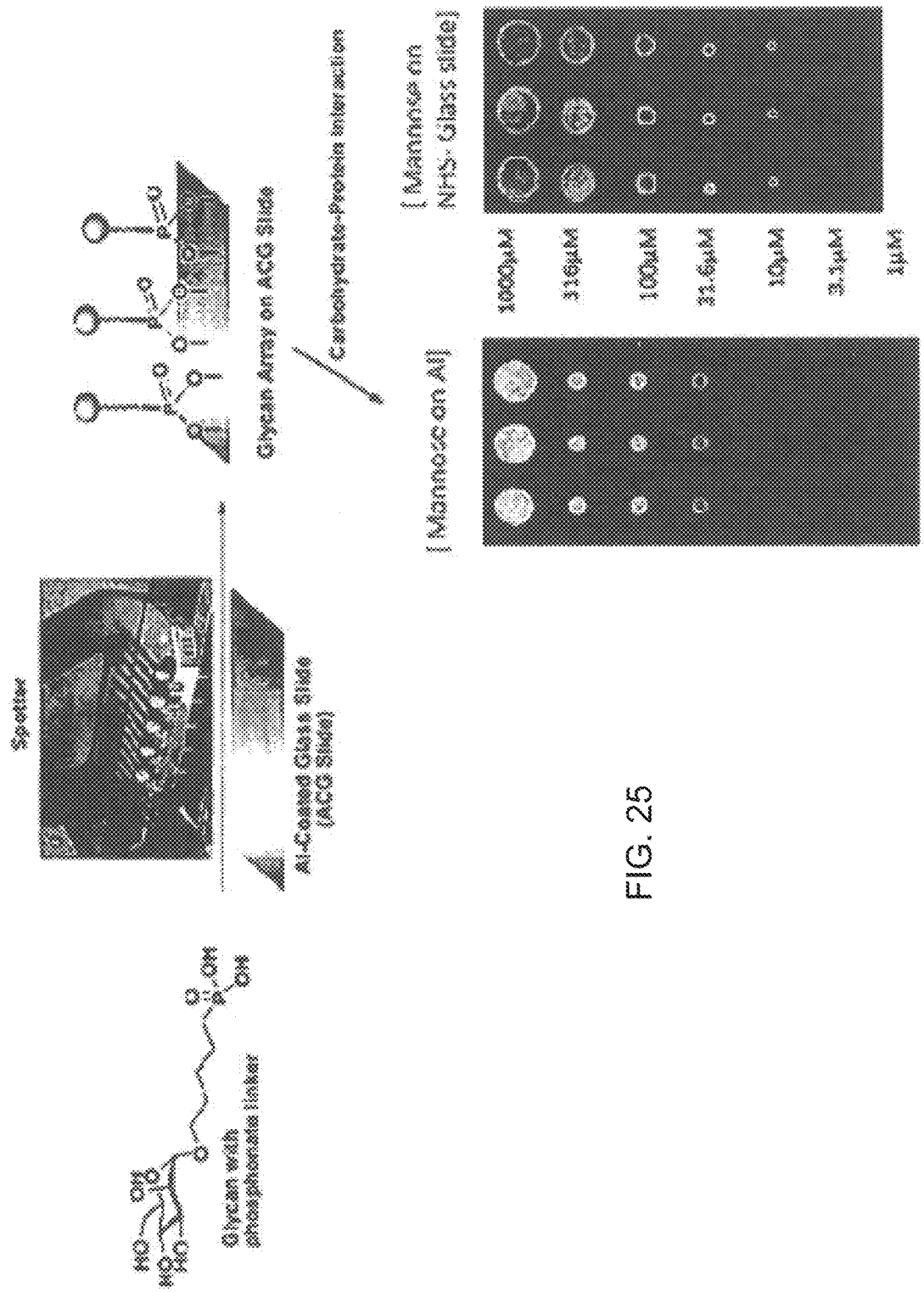
FIG. 25 is a block diagram of an implementations of a method of creation of covalent bonding glycan array on the ACG slide.

Compound 21 was dissolved in methanol. A solution of this sugar derivative was spotted robotically onto the PTFE-like ACG slide surface. After incubation, without blocking, the slides were rinsed repeatedly with distilled water, and used for protein binding analysis by using Alexa 488-labeled Concanavalin A as a protein source. Different incubation times were evaluated and 15 minutes was determined to be enough for the sugar derivative to chelate on the ACG slide. Different concentrations of compound 21 were also spotted on the ACG slide wherein the result was an ACG slide comparable to the NHS coated glass slide, as illustrated in FIG. 25.

Example 14: Materials and Methods

All chemicals and anhydrous solvents were purchased from a commercial source and used without further purification. Molecular Sieves (MS) for glycosylation were AW-300 (Aldrich). FluoroFlash® SPE cartridge was purchased from Sigma. Reactions were monitored with analytical thin-layer chromatography (TLC) in EM silica gel 60 F254 plates and visualized under UV (254 nm) and/or by staining with $KMnO_4$ or p-Anisadehyde. $^1H$ NMR spectra were recorded on a Bruker ULTRASHIELD-600 PLUS (600 MHz) spectrometer at 298K. Chemical shifts (in ppm) were assigned according to the internal standard signal of $CDCl_3$ ($\delta$=7.24 ppm). $^{13}C$ NMR spectra were obtained with Bruker ULTRASHIELD-600 PLUS spectrometer and were calibrated with $CDCl_3$ ($\delta$=77.00 ppm). Coupling constants (J) are reported in hertz (Hz) Splitting patterns are described by using the following abbreviations: s, singlet; brs, broad singlet, doublet; t, triplet; m, multiplet.

Substrate Materials

Micro glass slides (75.5×25.4×1 $mm^3$) were cleaned in piranha solution, a mixture of concentrated $H_2SO_4$ and 30% $H_2O_2$ (70:30 v/v), at 120° C. for 30 min, rinsed with plenty of deionized water until pH 7, and purge dried with high-quality nitrogen gas. The high-purity aluminum targets (99.999% pure) were obtained from Summit-Tech Resource Corp. (Hsin-Chu, Taiwan). These raw materials were provided to vendors Cheng-Jen Corp. (Kao-Hsiung, Taiwan) and Yujay-Tech Corp. (Chin-Ju, Taiwan) for the fabrication of ACG slides by using different coating techniques such as magnetron sputtering, cathode arc evaporation, and thermal evaporation. The fabricated ACG slides were either used directly or anodized with a DC current at 20 V (Keithley 2400 Model) at 48 C in 0.3M aqueous oxalic acid for 60-90 s. The surface properties of the fabricated ACG slides are shown in FIG. 1. The surfaces were sputtered with gold and examined by SEM (FEI XL30 SFEG, FEI Company). The surface roughness and thickness of the aluminum coating were measured by AFM (Dimension 3100 Veeco Instruments, Inc.). The surface compositions of these slides were analyzed by XPS by using an Omicron ESCA spectrometer with a monochromatic $Al_{K\alpha}$ X-ray (1486.6 eV) source under ultrahigh vacuum ($1\times10^{-10}$ Torr). All spectra were calibrated by the carbon is spectrum at 284.5 eV and the oxygen is spectrum at 532 eV.

Fabrication of $NH_2$-ACG Slides

The ACG slide was washed with acetone and water consecutively on a multishaker (FMS2 FINEPCR) for 2-3 min, purge-dried with high-purity nitrogen gas, and further dried in an oven at 100° C. for 10-15 min. Surface activation was conducted by a plasma cleaner (Harrick PDC 32 G, 200-600 mTorr) with oxygen, argon, or mixed gases at room temperature for 10 min. Immediately after plasma treatment, APDMES (0.8 mL) was placed evenly on the surface (in bulk), which was covered with a sealed petri dish and heated directly on a hot plate at 658 C for 40 min 1 h. When the reaction was completed, the sample slide was rinsed thoroughly, sonicated in methanol for 3 min (20% power), and purge-dried with high-purity nitrogen gas. The surface with aminosilane-grafted substrate was used for amide-linkage formation in situ with the mannose derivative compound 27 and HBTU. The commercial $NH_2$-glass slides (#40004 from Corning Inc.) were used for comparison of protein binding.

Fabrication of NHS-ACG Slides

ACG slides coated by thermal evaporation were further anodized in 0.2M oxalic acid for 90 s, rinsed with deionized water, and activated by argon plasma as usual. Without any contamination, the slide was assembled in a designed PTFE sealed, heat-transferable reaction cell, and APTES (1 mL, bulk) was immediately added to the cell. The PTFE cell was covered with a glass plate. Under moisture-free conditions, the cell was heated at 658 C for 30 min and rinsed thoroughly with methylene chloride and methanol. The slides were then purge-dried with nitrogen gas. Beforehand, a saturated solution of DSS (0.5 g; CAS #68528-80-30) in DMF (4 mL) and diisopropylethylamine (220 mL) was prepared. A portion (1.33 mL) of this saturated solution was added to each reaction cell. The NHS-ACG slide was formed within 3 h with constant swirling at room temperature. The slide was rinsed thoroughly with ethyl acetate and purge-dried with high-quality nitrogen gas. After the PTFE cell was dried and disassembled, the slide was ready for Globo H—$NH_2$ microarray.

ACG Slides Preparation—Fabrication of the Silane Based PTFE-Like ACG Slides

In a moisture-free condition, the argon plasma activated ACG slide was reacted with 3-aminopropyltriethylsilane in bulk at 65° C. for 30 minutes then washed with methylene chloride thoroughly and dried by nitrogen gas under atmospheric condition. The silanated ACG slide was immersed in a solvent mixture (DMF/IPA/DIPEA 12/6/1 volume ratio) of N-succinimidyl 3-perfluorooctylpropionate (0.05 wt %) solution for two hours at room temperature. After the reaction, the slide was rinsed with IPA thoroughly, and purged dried with nitrogen gas. Water contact angle ($\geq 115°$) measurement was quickly checked for the completion of the slide fabrication.

ACG Slides Preparation—Fabrication of the Phosphonic Acid Based PTFE-Like ACG Slides The aluminum coated glass slide was washed by acetone and water for three times, and then dried by dry clean air. The clean slide was then activated and cleaned by oxygen plasma (Harrick plasma, PDC-32G) for 15 mins. After activation, the slide was immersed into 3,3,4,4,5,5,6,6,7,7,8,8,9,9,10,10,10-heptadecafluorodecylphosphonic acid (HDFDPA) 3 solution (1M, 65% 2-propanol in $H_2O$, pH=6.17) immediately. The solution was vibrated by gentle sonication (50 W) for 15 mins. Following the ultrasonic treatment, the slide was removed from the solution and then immersed into another pure 2-propanol solution for 15 mins. The solution was also sonicated to assist the removal of excess phosphonic acid on the slide surface. The slide was dried by dry nitrogen and reduced pressure. Upon the completion of the reaction, the slide was washed thoroughly with IPA, and nitrogen purge dried. Water contact angle ($\geq 115°$) measurement was quickly checked for the completion of the slide fabrication.

Reference-Controlled NHS-Glass Slides

NETS-glass slides (from SCHOTF, North America) were used directly. The $NH_2$-glass slide (#40004 from Corning, Inc.) was modified by using the same preparation method for the NHS-ACG slide. The slide was assembled in a designed PTFE sealed, heat-transferable reaction cell. A portion (1.33 mL) of saturated DSS solution was added for reaction with the $NH_2$-glass surface. After constant swirling at room temperature for 3 h, the slide was rinsed thoroughly with ethyl acetate and purge-dried with high-quality nitrogen gas. After the PTFE cell was dried and disassembled, the slides were ready for Globo H—$NH_2$ microarray.

Chemical Materials

All chemicals employed in the synthesis of 6 were purchased from Aldrich or the specified individual chemical companies and used without any further purification.

Synthesis

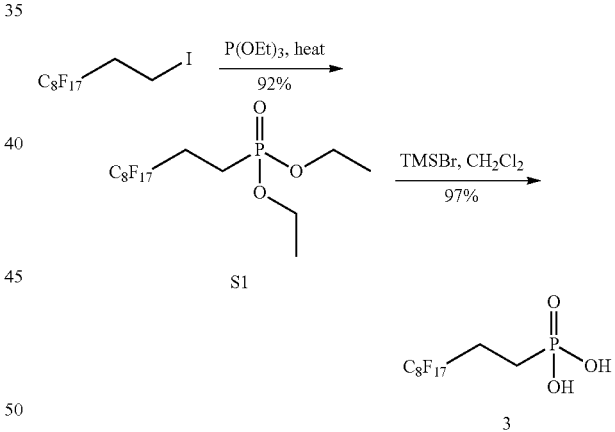

Preparation of 3

Diethyl 3,3,4,4,5,5,6,6,7,7,8,8,9,9,10,10,10-heptadecafluorodecylphosphonate (S1): 1,1,1,2,2,3,3,4,4,5,5,6,6,7,7,8,8-heptadecafluoro-10-iododecane (1.02 g, 1.78 mmol) and $P(OEt)_3$ (15 ml, excess) was added to 50 ml round bottom flask. The mixture was heated to 120° C. under nitrogen for 40 hours and then purified with Fluor® Flash® SPE cartridge. The remaining light yellow oil was chromatographed with Ethyl Acetate/Hexane to give product. (0.96 g, 92%). $^1H$ NMR (600 MHz, $CDCl_3$): δ (ppm) 4.10-4.00 (m, 4H, $CH_2CH_3$), 2.35-2.23 (m, 2H, $CH_2CF_2$), 1.92-1.86 (m, 2H, $PCH_2$), 1.25 (t, J=7.2 Hz, 6H, $CH_2CH_3$). $^{13}C$ NMR (150 MHz, $CDCl_3$): δ (ppm) 121-106 (m, C—F coupling unsolved), 62.28 (d, $^2J_{cp}$=6 Hz, CH$_2$CH$_3$), 25.33 (t, $^2J_cF$=23 Hz, CH$_2$CF$_2$), 17.24 (d, $^2J_{cp}$=148 Hz, PCH$_2$), 16.38, $^3J_{cp}$=6 Hz, CH$_2$CH$_3$), HRMS calcd for C$_{14}$H$_{14}$F$_{17}$O$_3$P: [M+H]$^+$, 585.0487. found: 585.0433.

3,3,4,4,5,5,6,6,7,7,8,8,9,9,10,10,10-heptadecafluorodecylphosphonic acid (3): Bromotrimethylsilane (0.74 mL, 5.75 mmol) was added via syringe to a solution of Si (1.12 g, 1.92 mmol) in anhydrous CH$_2$Cl$_2$ (15 ml) under nitrogen. The mixture was stirred for 30 hours. Volatiles were removed in vacuo completely to give white powder. The white powder can be used for next experiment directly without further purification. (0.99 g, 97%). $^1$H NMR (600 MHz, MeOD): δ (ppm) 2.48-2.42 (m, 2H, CH$_2$CF$_2$), 1.99-1.96 (m, 2H, PCH$_2$). $^{13}$C NMR (150 MHz, MeOD): δ (ppm) 121-106 (m, C—F coupling unsolved), 25.55 (t, $^2J_cF$=23 Hz, CH$_2$CF$_2$), 18.26 (d, $^2J_{cp}$=143 Hz, PCH$_2$). HRMS calcd for C$_{10}$H$_5$F$_{17}$O$_3$P: [M−H]$^−$, 526.9699. found: 526.9669.

Preparation of Polyfluorinated Mannose 4

2,5-dioxopyrrolidin-1-yl 4,4,5,5,6,6,7,7,8,8,9,9,10,10,11,11,11-heptadecafluoroundecyl carbonate (S2): To a stirred solution of 4,4,5,5,6,6,7,7,8,8,9,9,10,10,11,11,11-heptadecafluoroundecan-1-ol (214 mg, 0.45 mmol) and DSC (184 mg, 0.72 mmol) in acetonitrile was added triethylamine (0.5 ml, 3.60 mmol) at 0° C. under nitrogen and then the solution warmed up slowly to room temperature and stirred for 16 hours. The reaction was washed with H$_2$O three times. The organic layer was dried over Na$_2$SO$_4$, filtered and concentrated under reduced pressure. The product was purified by flash chromatography to give white solid. (242 mg, 87%). $^1$H NMR (600 MHz, CDCl$_3$): δ (ppm) 4.40 (t, 2H, J=6.3 Hz, CH$_2$O), 2.83 (s, 4H), 2.27-2.18 (m, 2H, CH$_2$CH$_2$F), 2.10-2.05 (m, 2H, FCH$_2$). $^{13}$C NMR (150 Mhz, CDCl$_3$): δ (ppm) 168.73 (NCO), 151.65 (OCO), 121-106 (m, C—F coupling unsolved), 69.87 (OCH$_2$), 25.66 (FCH$_2$), 20.12 (FCH$_2$CH$_2$)

[(4,4,5,5,6,6,7,7,8,8,9,9,10,10,11,11,12,12,12-nonadecafluorododecoxycarbonyl-amino)pentyl] α-D-mannopyranoside (4): To a stirred solution of S2 (250 mg, 0.40 mmol) and 5-Aminopentyl α-D-manno-pyranoside (112 mg, 0.39 mmol) in CH$_2$Cl$_2$ was added triethylamine (0.2 mL) at 0° C. under nitrogen and then the ice bath was removed. The reaction warmed up to room temperature and stirred overnight. The solvent was removed in vacuo and the product was purified by Fluor® Flash® SPE cartridge and flash chromatography to give white solid. (253 mg, 83%). 1H NMR (600 MHz, CDCl$_3$): δ (ppm) 7.97 (s, 1H, NH), 4.72 (d, J=1.6 Hz, 1H, 1-H of Man), 4.10 (t, J=6.2 Hz, 2H, O—CH$_2$), 3.82-3.80 (m, 1H), 3.77-3.76 (m, 1H), 3.73-3.70 (m, 2H), 3.69-3.66 (m, 1H), 3.59 (t, J=9.6 Hz, 1H), 3.52-3.49 (m, 1H), 3.42-3.38 (m, 1H), 3.08 (t, J=7.1 Hz, 1H, O—CH$_2$), 2.32-2.23 (m, 2H, CH$_2$CH$_2$F), 1.94-1.89 (m, 2H, FCH$_2$), 1.63-1.54 (m, 2H), 1.51-1.46 (m, 2H), 1.42-1.32 (m, 4H), $^{13}$C NMR (150 MHz, CDCl$_3$): δ (ppm) 157.44 (NCO), 120-105 (m, C—F coupling unsolved), 100.12 (1-C of Man), 73.19, 71.25, 70.87, 67.22, 67.04, 62.80, 61.51, 40.27 (CH$_2$N), 29.41, 19.10, 26.20, 25.63, 24.86, 20.07. HRMS calcd for C$_{23}$H$_{28}$F$_{17}$NO$_8$: [M+Na]$^+$, 806.1598. found: 806.1643.

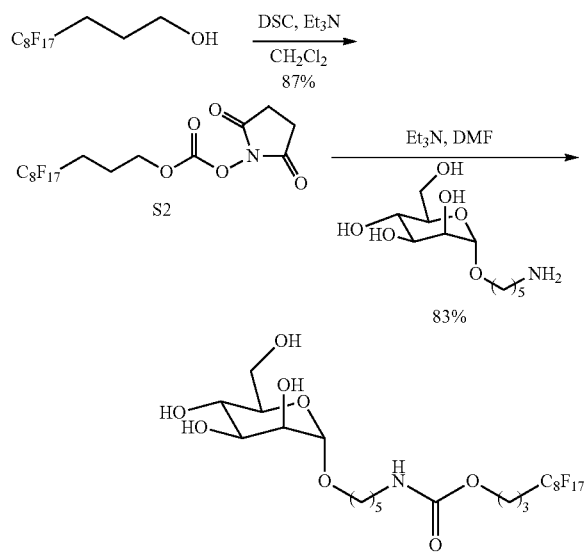

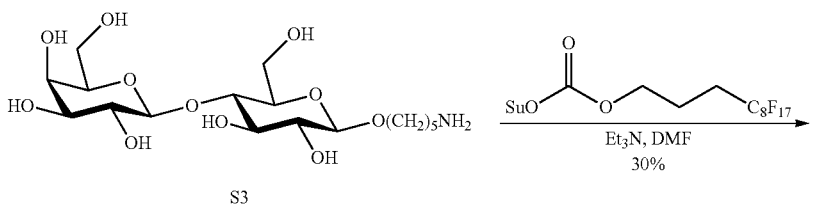

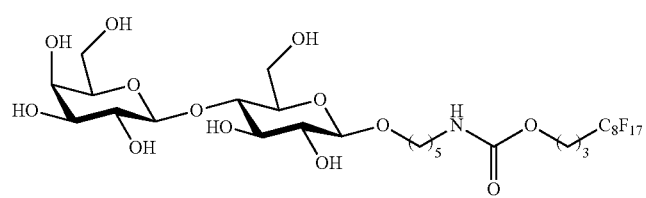

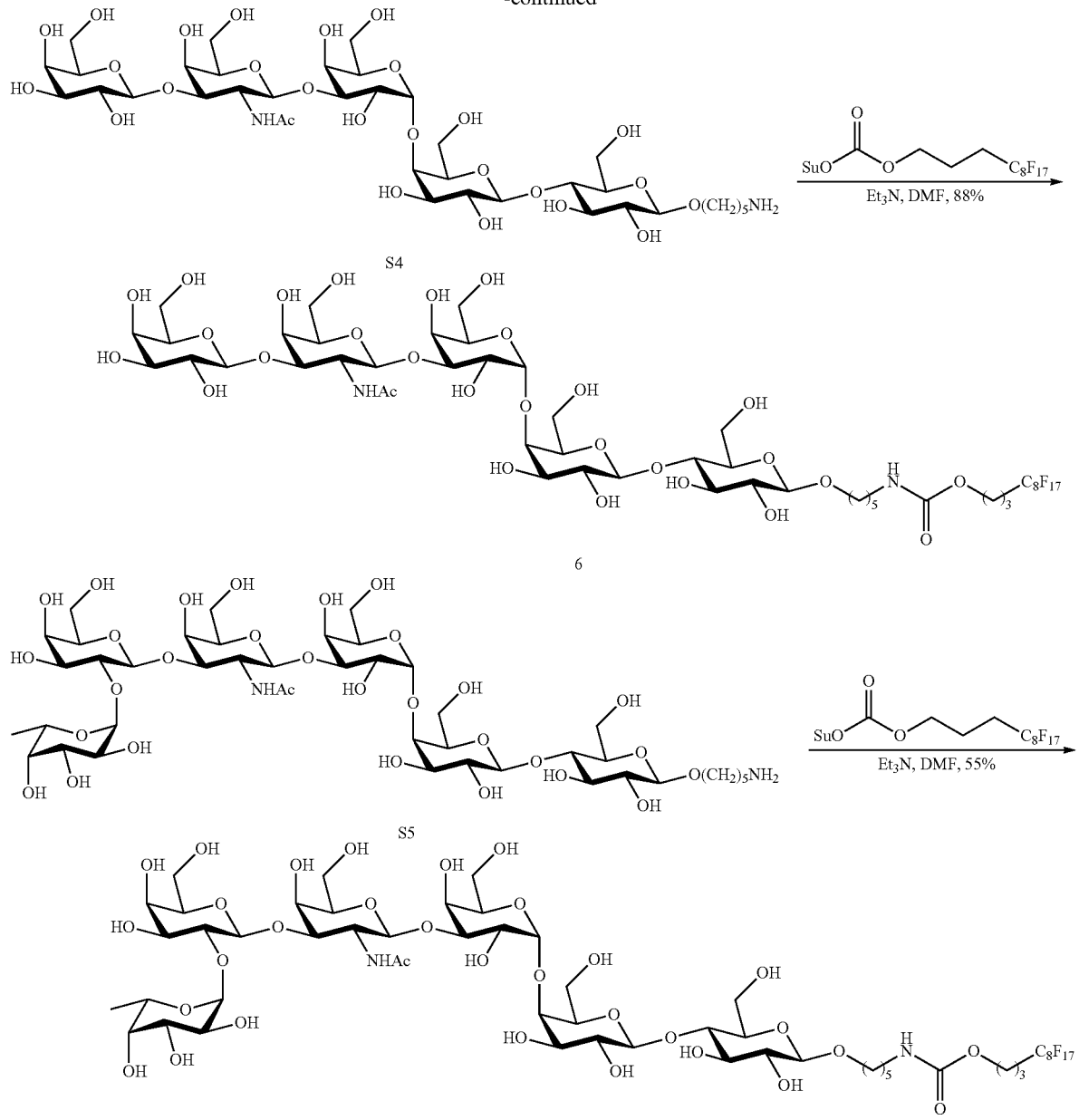

Synthesis of Polyfluorinated 5, 6, and 7

[(4,4,5,5,6,6,7,7,8,8,9,9,10,10,11,11,12,12,12-nonadeca-flourododecoxycarbonyl-amino)pentyl] ß-D-lactoside (5): The solution of S3 (44 mg, 0.10 mmol) and S2 (76 mg, 0.12 mmol) in DMF (5 mL) was added Et$_3$N (28 μL, 0.20 mmol) at 0° C. After stirring at room temperature overnight, the reaction mixture was concentrated in vacuo and purified by column chromatography and FluoroFlash® SPE cartridge to give 5 as white foamy solid (29 mg, 30%). Rf: 0.68 (EtOAc:MeOH=5:1). $^1$H NMR (600 MHz, MeOD): δ 4.36 (d, J=7.6 Hz, 1H), 4.27 (d, J=7.8 Hz, 1H), 4.15 (bt, 1H), 4.10 (t, J=6.0 Hz, 2H), 3.90-3.40 (m, 12H), 3.39 (m, 1H), 3.25 (t, J=8.1 Hz, 1H), 3.09 (t, J=6.9 Hz, 2H), 2.31-2.26 (m, 2H), 1.93-1.90 (m, 2H), 1.64-1.62 (m, 2H), 1.52-1.49 (m, 2H), 1.42-1.40 (m, 2H). $^{13}$C NMR (150 MHz, MeOD): δ 157.53, 120.62-110.33 (m, C—F coupling unresolved), 103.79, 102.93, 79.38, 75.79, 75.16, 75.13, 73.52, 73.46, 71.26, 69.38, 69.00, 62.90, 61.19, 60.62, 40.36, 29.29, 29.05, 27.33 (t), 22.96, 20.18. MS (ESI) Calcd for C$_{29}$H$_{38}$F$_{17}$NO$_{13}$Na+: 954.1970 [M+Na]$^+$. found: 954-1964.

[(4,4,5,5,6,6,7,7,8,8,9,9,10,10,11,11,12,12,12-nonadeca-fluorododecoxycarbonyl-amino)pentyl] ß-D-galactopyranosyl-(1→3)-2-acetamido-2-deoxy-ß-D-galactopyranosyl-(1→3)-α-D-galactopyranosyl-(1→4)-ß-D-galactopyranosyl-(1→4)-ß-D-glucopyranoside (6): Compound 6 was prepared from compound S4 according to the procedure as described for 5 in 55% yields after purification by column chromatography and Fluor® Flash® SPE cartridge. R$_f$: 0.18 (EtOAc:MeOH=1:1). White foamy solid. $^1$H NMR (600 MHz, MeOD): δ 4.72 (d, J=8.4 Hz, 1H), 4.44 (d, J=7.0 Hz, 1H), 4.37 (d, J=7.4 Hz, 1H), 4.31 (d, J=7.7 Hz, 1H), 4.29 (m, 1H), 4.19 (d, J=2.1 Hz, 1H), 4.13 (t, d, J=6.0 Hz, 2H), 4.09 (m, 1H), 4.01 (bs, 1H), 3.95-3.67 (m, 20H), 3.60-3.42 (m, 11H), 3.26 (t, J=8.6 Hz, 1H), 3.12 (t, J=7.0 Hz, 2H), 2.34-2.26 (m, 2H), 2.01 (s, 3H), 1.98-1.91 (m, 2H), 1.69-1.64 (m, 2H), 1.55-1.52 (m, 2H), 1.46-1.43 (m, 2H). $^{13}$C NMR (150 MHz, MeOD): δ 173.69, 157.44, 120.11-108.43 (m, C—F coupling unresolved), 105.22, 104.06, 102.91, 102.80, 101.38, 80.11, 79.83, 79.34, 78.55, 75.38, 75.11, 75.05, 74.97, 74.94, 73.46, 73.24, 73.17, 71.17, 71.07, 71.00, 69.31, 69.21, 68.87, 68.14, 68.07, 62.81, 61.21, 60.50, 60.16, 51.98, 40.26, 29.22, 28.97, 22.87, 21.95, 20.08, 19.47. MS (MALDI) Calcd for $C_{49}H_{71}F_{17}N_2O_8Na^+$: 1481.382 [M+Na]$^+$. found: 1481.452.

[(4,4,5,5,6,6,7,7,8,8,9,9,10,10,11,11,12,12,12-nonadeca-fluorododecoxycarbonyl-amino)pentyl] α-L-fucopyranosyl-(1→2)-ß-D-galactopyranosyl-(1→-3)-2-acetamido-2-de-oxy-ß-D-galactopyranosyl-(1→3)-ß-D-galactopyranosyl-(1→4)-ß-D-galacto-pyranosyl-(1→4)-ß-D-glucopyranoside (7): Compound 7 was prepared from compound S5 according to the procedure as described for 5 in 88% yields after purification by column chromatography and FluoroFlash® SPE cartridge. R$_f$: 0.18 (EtOAc:MeOH=1:1). White foamy solid. $^1$H NMR (600 MHz, MeOD): δ 5.26 (d, J=3.8 Hz, 1H), 4.96 (d, J=3.8 Hz, 1H), 4.58 (d, J=7.9 Hz, 1H), 4.44 (d, J=7.0 Hz, 1H), 4.30 (d, J=7.6 Hz, 1H), 4.29 (m, 1H), 4.17-4.10 (m, 5H), 4.01 (bs, 1H), 3.93-3.69 (m, 24H), 3.68-3.53 (m, 8H), 3.44-3.41 (m, 1H), 3.26 (t, J=8.6 Hz, 1H), 3.12 (t, J=7.0 Hz, 2H), 2.32-2.28 (m, 2H), 2.04 (s, 3H), 1.97-1.93 (m, 2H), 1.69-1.64 (m, 2H), 1.56-1.52 (m, 2H), 1.47-1.42 (m, 2H), 1.27 (d, J=6.5 Hz, 3H). $^{13}$C NMR (150 MHz, MeOD): δ 173.17, 157.55, 104.20, 104.07, 102.93, 102.59, 101.54, 99.78, 80.05, 79.26, 78.81, 77.83, 76.82, 75.50, 75.21, 75.09, 74.23, 73.56, 73.41, 72.25, 71.33, 71.22, 70.25, 69.41, 69.32, 69.09, 68.37, 68.33, 66.83, 62.91, 61.31, 61.26, 60.65, 60.25, 51.82, 40.37, 29.32, 29.07, 22.97, 22.18, 20.19, 15.40. MS (MALDI) Calcd for $C_{55}H_{81}F_{17}N_2O_{32}Na^+$: 1627.440 [M+Na]+. found: 1627.526.

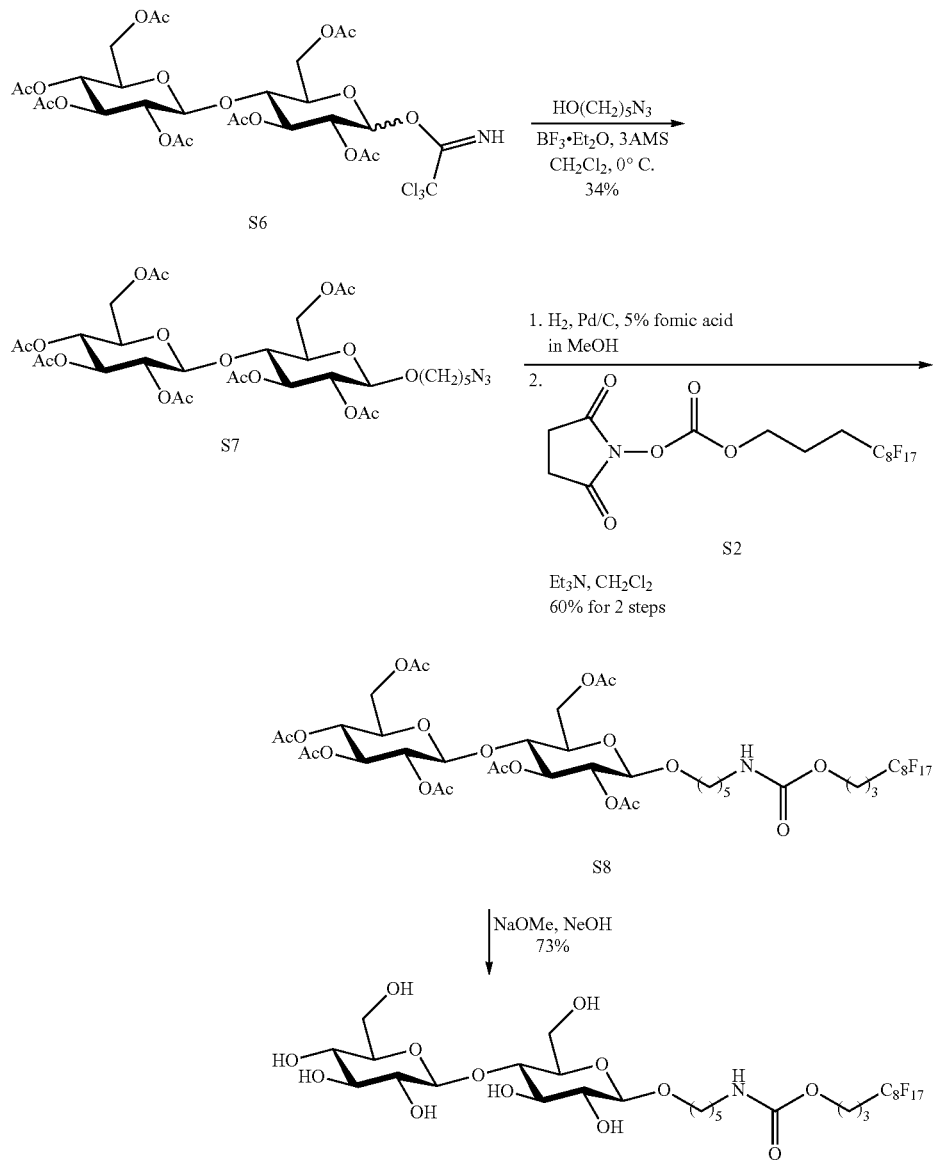

Synthesis of Polyflouro-Cellobioside 8

5-Azidopentyl 2,3,6,2,3,4,6'-hepta-O-acetyl-ß-D-cellobioside (S7): A suspension of the compound S6 (1.01 g, 1.29 mmol), s-azido-1-pentanol (0.84 g, 6.47 mmol), and 3 Å molecular sieves in CH$_2$Cl$_2$ (10 mL) was stirred at room temperature for 1 h. The reaction mixture was cooled to 0° C. and treated dropwise with BF$_3$.Et$_2$O (33 μL, 0.26 mmol). After stirring at 0° C. for 2 h, saturated aqueous NaHCO$_3$ was added and the reaction mixture was filtered with Celite. The mixture was diluted with CH$_2$Cl$_2$ and then washed with brine. The organic phase was dried over Na$_2$SO$_4$ and evaporated the solvent and purified by chromatography (Hexane:EtOAc=3:1→2:1→1:1) to give S7 as a white foamy solid (330 mg, 34%). R$_f$: 0.48 (Hexane:EtOAc=1:1). $^1$H NMR (600 MHz, CDCl$_3$): δ 5.16 (t, J=9.4 Hz, 1H), 5.13 (t, J=9.4 Hz, 1H), 5.04 (t, J=9.7 Hz, 1H), 4.91-4.85 (m, 2H), 4.50-4.47 (m, 2H), 4.42 (d, J=8.2 Hz, 1H), 4.34 (dd, J=12.5, 4.3 Hz, 1H), 4.06 (dd, J=12.0, 4.7 Hz, 1H), 4.01 (dd, J=12.3, 1.9 Hz, 1H), 3.81 (m, 1H), 3.74 (t, J=9.5 Hz, 1H), 3.64-3.62 (m, 1H), 3.56 (m, 1H), 3.43 (m, 1H), 3.23 (t, J=6.8 Hz, 2H), 2.10 (s, 3H), 2.06 (s, 3H), 2.01 (s, 3H), 2.00 (s, 3H), 1.99 (s, 3H), 1.98 (s, 3H), 1.96 (s, 3H), 1.59-1.54 (m, 4H), 1.40-1.35 (m, 2H). $^{13}$C NMR (150 MHz, CDCl$_3$): δ 170.54, 170.34, 170.26, 169.86, 169.60, 169.34, 169.08, 100.81, 100.64, 76.51, 72.94, 72.67, 72.49, 71.96, 71.61, 71.56, 69.73, 67.76, 61.84, 61.54, 51.33, 28.94, 28.52, 23.14, 21.08, 20.90, 20.69, 20.57. FIRMS (ESI) Calcd for C$_{31}$H$_{45}$N$_3$O$_{18}$Na$^+$: 770.2590 [M+Na]$^+$. found: 770.2570.

[(4,4,5,5,6,6,7,7,8,8,9,9,10,10,11,11,12,12,12-nonadecafluorododecoxycarbonyl-amino)pentyl] 2,3,6,2,3,4,6'-hepta-O-acetyl-ß-D-cellobioside (S8): A suspension of S7 (50 mg, 0.07 mmol), catalytic amount of Pd/C in 5% formic acid in MeOH (5 mL) was stirred under H$_2$ balloon for 2 h. After filtration through Celite, the filter cake was washed with MeOH. The filtrate was evaporated and co-evaporated with toluene. The residue underwent to next step without purification.

The residue described above was dissolved in CH$_2$Cl$_2$ (5 mL) and then Compound S2 (50 mg, 0.08 mmol) was added. The mixture was cooled to 0° C. Triethylamine (19 .mu.L, 0.13 mmol) was added and the solution continued stirring at room temperature for 12 h. The reaction mixture was concentrated and purified by chromatography (Hexane:EtOAc=1:1) to give S8 as a white foamy solid (49 mg, 60% in two steps). $^1$H NMR (600 MHz, CDCl$_3$): δ 5.14 (t, J=9.5 Hz, 1H), 5.11 (t, J=9.5 Hz, 1H), 5.03 (t, J=, 9.5 Hz, 1H), 4.91-4.84 (m, 2H), 4.76 (br, 1H), 4.50 (dd, J=12.0, 1.7 Hz, 1H), 4.48 (d, J=7.9 Hz, 1H), 4.40 (d, J=8.0 Hz, 1H), 4.34 (dd, J=12.5, 4.3 Hz, 1H), 4.09 (t, J=6.1 Hz, 2H), 4.05 (dd, J=12.0, 4.9 Hz, 1H), 4.01 (dd, J=12.5, 2.2 Hz, 1H), 3.80 (m, 1H), 3.73 (t, J=9.5 Hz, 1H), 3.64-3.61 (m, 1H), 3.55-3.53 (m, 1H), 3.43 (m, 1H), 3.12 (m, 2H), 2.18-2.13 (m, 2H), 2.09 (s, 3H), 2.05 (s, 3H), 2.00 (2xs, 6H), 1.98 (s, 3H), 1.97 (s, 3H), 1.95 (s, 3H), 1.92-1.88 (m, 2H), 1.56-1.52 (m, 2H), 1.49-1.44 (m, 2H), 1.34-1.29 (m, 2H). $^{13}$C NMR (150 MHz, CDCl$_3$): δ 170.51, 170.35, 170.25, 169.84, 169.62, 169.33, 169.06, 156.25, 120.18-108.01 (m, C—F coupling unresolved), 100.78, 100.62, 76.47, 72.91, 72.68, 72.45, 71.94, 71.60, 71.56, 69.77, 67.74, 63.17, 61.76, 61.52, 40.83, 29.68, 29.49, 28.92, 27.99, 27.84, 27.69, 23.02, 21.03, 20.84, 20.64, 20.53, 20.33. HRMS (ESI) Calcd for C$_{43}$H$_{52}$F$_{17}$NO$_2$ONa$^+$: 1248.2703 [M+Na]$^+$. found: 1248.2675.

[(4,4,5,5,6,6,7,7,8,8,9,9,10,10,11,11,12,12,12-nonadecafluorododecoxycarbonyl-amino)pentyl] ß-D-cellobioside (8): The solution of S8 (222 mg, 0.18 mmol) and NaOMe (50 mg, 0.09 mmol) in MeOH (7 mL) was stirred at room temperature overnight. The mixture was neutralized with Amberlyst-15 ion-exchange resign for 5 min and filtered through a sintered funnel packed with Celite. The filter pad was rinsed with methanol after filtration. The combined filtrates were concentrated under reduced pressure and then purified by flash column chromatography (EtOAc:MeOH=10:1→8:1) to give 8 as a white solid (123 mg, 73%). R$_f$: 0.47 (EtOAc:MeOH=5:1). $^1$H NMR (600 MHz, MeOD): δ 4.40 (d, J=7.9 Hz, 1H), 4.27 (d, J=7.8 Hz, 1H), 4.10 (t, J=6.1 Hz, 2H), 3.89-3.86 (m, 4H), 3.65 (dd, J=11.8, 5.7 Hz, 1H), 3.57-3.53 (m, 2H), 3.50 (t, J=9.0 Hz, 1H), 3.39-3.32 (m, 3H), 3.30 (m, 1H), 3.22 (m, 2H), 3.09 (t, J=6.7 Hz, 2H), 2.32-2.23 (m, 2H), 1.94-1.89 (m, 2H), 1.66-1.61 (m, 2H), 1.53-1.48 (m, 2H), 1.43-1.38 (m, 2H). $^{13}$C NMR (150 MHz, MeOD): δ 157.51, 120.11-108.43 (m, C—F coupling unresolved), 103.20, 102.79, 79.31, 76.69, 76.43, 75.03, 73.47, 69.95, 69.29, 61.00, 60.74, 60.42, 40.32, 29.52, 28.95, 27.36, 27.21, 27.07, 22.86, 20.07. HRMS (ESI) Calcd for C$_{29}$H$_{38}$F$_{17}$NO$_{13}$Na$^+$: 954.1964 [M+Na]$^+$. found: 954.1966.

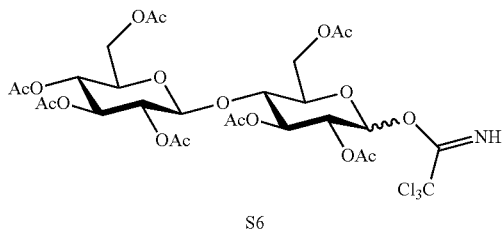 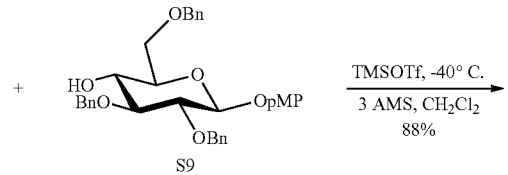

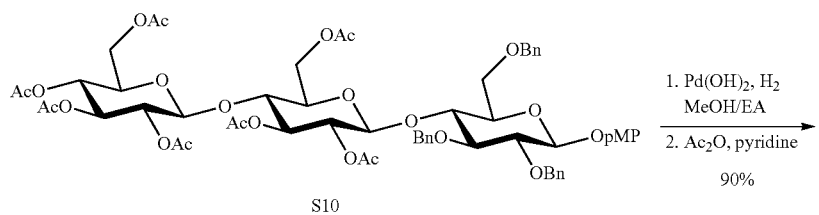

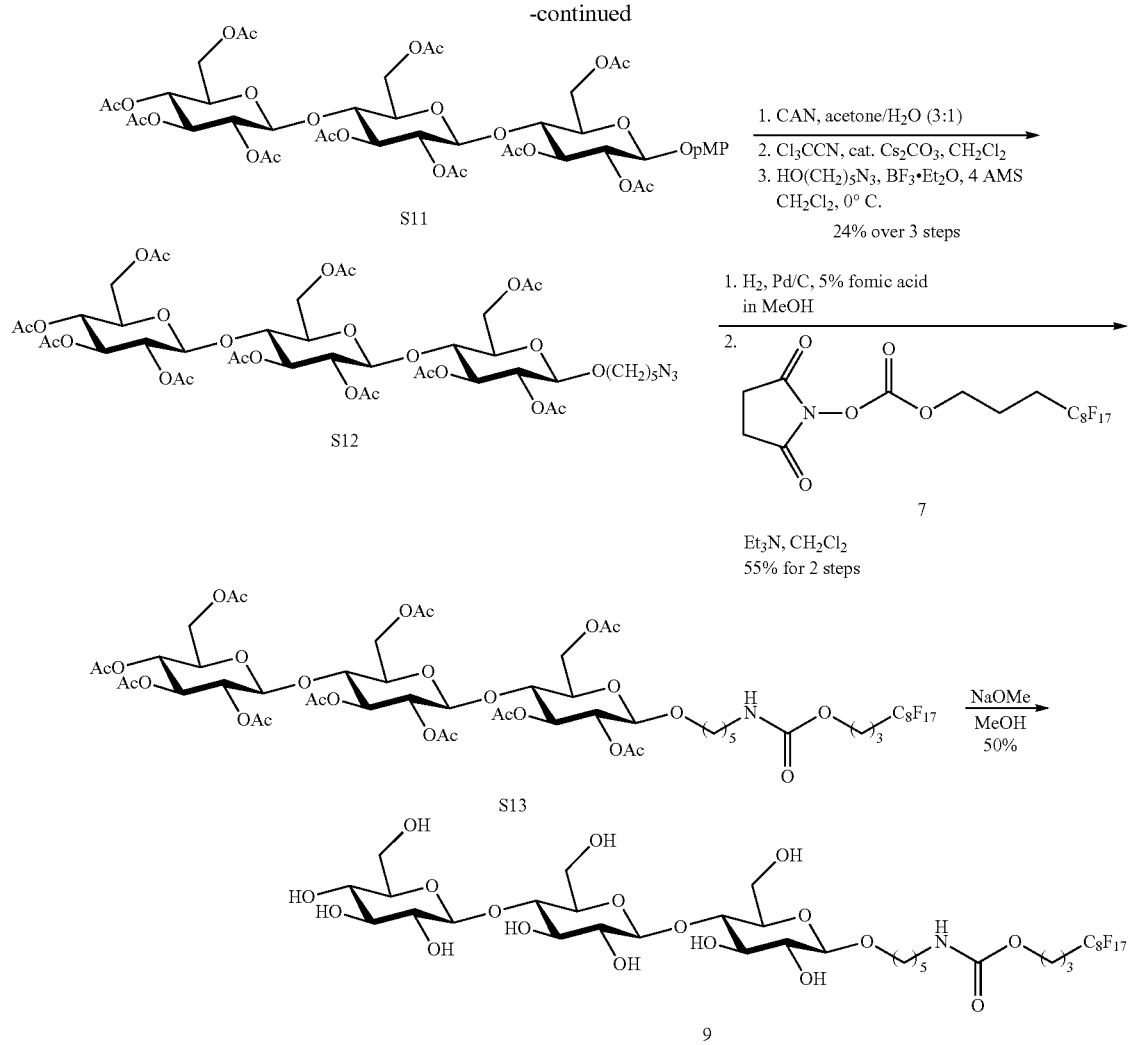

Synthesis of Polyflouro-Cellotrioside 9 para-Methoxyphenyl 2,3,4,6-tetra-O-acetyl-ß-D-glucopyranosyl-(1→4)-2,3,6-tri-O-acetyl-ß-D-glucopyranosyl-(1→4)-2,3,6-tri-O-benzyl-ß-D-glucopyranoside (S10): According to similar procedures reported by Vesalla, a suspension of S6 (1.68 g, 2.16 mmol), S9 (1.0 g, 1.8 mmol) and 3 Å mol. sieves in $CH_2Cl_2$ (20 mL) was stirred at room temperature for 1 h. The reaction mixture was cooled to −40° C. and treated dropwise with TMSOTf (98 μl, 0.54 mmol). After stirring at −40° C. for 2 h, saturated aqueous $NaHCO_3$ was added and the reaction mixture was filtered with Celite. The mixture was diluted with $CH_2Cl_2$ and then washed with brine. The organic phase was dried over $Na_2SO_4$ and evaporated the solvent and purified by chromatography (Hexane:EtOAc=3:1→2:1→1:1) to give S10 as a white foamy solid (1.86 g, 88%). $R_f$: 0.55 (Hexane:EtOAc=1:1). $^1H$ NMR (600 MHz, $CDCl_3$): δ 7.38-7.25 (m, 15H), 7.00 (d, J=9.1 Hz, 2H), 6.81 (d, J=9.1 Hz, 2H), 5.10-5.05 (m, 2H), 5.00-4.98 (m, 2H), 4.94-4.91 (m, 2H), 4.85-4.82 (m, 2H), 4.78 (d, J=11.6 Hz, 1H), 4.72 (d, J=11.6 Hz, 2H), 4.64 (d, J=8.2 Hz, 1H), 4.49 (d, J=12.0 Hz, 1H), 4.39 (d, J=7.9 Hz, 1H), 4.37 (dd, J=12.5, 4.3 Hz, 1H), 4.23 (dd, J=12.0, 2.0 Hz, 1H), 4.01 (dd, J=12.0, 2.2 Hz, 1H), 3.95 (t, J=9.2 Hz, 1H), 3.90 (dd, J=12.0, 4.6 Hz, 1H), 3.78 (s, 3H), 3.78-3.62 (m, 6H), 3.46-3.44 (m, 1H), 3.19-3.16 (m, 1H), 2.08 (s, 3H), 2.02 (s, 3H), 2.00 (s, 3H), 1.99 (s, 3H), 1.98 (s, 3H), 1.97 (s, 3H), 1.95 (s, 3H). $^{13}C$ NMR (150 MHz, $CDCl_3$): δ 170.71 170.46, 170.42, 170.01, 169.68, 169.53, 169.22, 155.53, 151.64, 139.42, 138.34, 138.01, 128.79, 128.48, 128.38, 128.35, 128.26, 128.20, 127.86, 127.40, 127.13, 118.70, 114.71, 102.91, 101.04, 100.15, 82.77, 81.60, 76.39, 75.20, 74.92, 74.89, 73.85, 73.11, 72.67, 72.37, 72.09, 71.65, 67.99, 67.93, 61.98, 61.70, 55.85, 20.93, 20.88, 20.75. HRMS (ESI) Calcd for $C_{60}H_{70}O_{24}Na^+$: 1197.4149 [M+Na]$^+$. found: 1197.4142.

para-Methoxyphenyl 2,3,4,6-tetra-O-acetyl-ß-D-glucopyranosyl-(1→4)-2,3,6-tri-O-acetyl-ß-D-glucopyranosyl-(1→4)-2,3,6-tri-O-acetyl-ß-D-glucopyranoside (S11): A suspension of S10 (1.01 g, 0.86 mmol), catalytic amount of $Pd(OH)_2$ in MeOH/EA (1/1, 10 mL) was stirred under $H_2$ balloon for 12 h. After filtration through Celite, the filter cake was washed with MeOH. The filtrate was evaporated and the residue underwent to next step without purification.

The residue described above was dissolved in pyridine (5 mL) and acetic anhydride (5 mL). The mixture was stirred at room temperature overnight. The solution was added MeOH to destroy the excess acetic anhydride and then concentrated in vacuo. $CH_2Cl_2$ was added and the reaction mixture was washed with 1M aqueous HCl, saturated aqueous $NaHCO_3$ and brine. The organic phase was dried over Na$_2$SO$_4$ concentrated and purified by chromatography (Hexane:EtOAc=1:1) to give S11 as a white foamy solid (794 mg, 90% in two steps). R$_f$: 0.24 (Hexane:EtOAc=1:1). $^1$H NMR (600 MHz, CDCl$_3$): δ 6.88 (d, J=9.0 Hz, 2H), 6.76 (d, J=9.0 Hz, 2H), 5.19 (t, J=9.2 Hz, 1H), 5.11-5.07 (m, 3H), 5.02 (t, J=9.7 Hz, 1H), 4.88-4.81 (m, 4H), 4.50 (dd, J=12.0, 2.0 Hz, 1H), 4.46 (d, J=8.0 Hz, 1H), 4.44 (d, J=8.0 Hz, 1H), 4.37 (dd, J=12.0, 2.0 Hz, 1H), 4.32 (dd, J=12.5, 4.3 Hz, 1H), 4.10-4.06 (m, 2H), 4.00 (dd, J=12.5, 2.0 Hz, 1H), 3.80 (t, J=9.5 Hz, 1H), 3.73 (t, J=9.5 Hz, 1H), 3.72 (s, 3H), 3.67-3.64 (m, 1H), 3.61-3.55 (m, 2H), 2.11 (s, 3H), 2.07 (s, 3H), 2.05 (s, 3H), 2.02 (s, 3H), 2.00 (s, 3H), 1.99 (s, 3H), 1.97 (2s, 6H), 1.96 (s, 3H), 1.94 (s, 3H). $^{13}$C NMR (150 MHz, CDCl$_3$): δ 170.53, 170.27, 170.23, 169.79, 169.57, 169.32, 169.10, 155.77, 150.88, 118.69, 114.53, 100.80, 100.57, 100.07, 76.44, 76.13, 72.89, 72.81, 72.77, 72.65, 72.41, 72.02, 71.75, 71.55, 71.52, 67.70, 62.15, 61.49, 55.67, 20.86, 20.80, 20.70, 20.57, 20.50. HRMS (ESI) Calcd for C$_{45}$H$_{58}$O$_{27}$Na$^+$: 1053.3058 [M+Na]$^+$. found: 1053.3051.

5-Azidopentyl 2,3,4,6-tetra-O-acetyl-ß-D-glucopyranosyl-(1→4)-2,3,6-tri-O-acetyl-ß-D-glucopyranosyl-(1→4)-2,3,6-tri-O-acetyl-ß-D-glucopyranoside (S12): Compound S11 (866 mg, 0.84 mmol) was dissolved in acetone-H$_2$O (20 mL 3:1), and the mixture was cooled (ice-water bath). A solution of CAN (2.3 g, 4.20 mmol) in acetone/H$_2$O (10 mL 3:1) was added, and the mixture was stirred at room temperature for 30 min. The mixture was concentrated to a volume of 10 mL, diluted with CH$_2$Cl$_2$, washed with saturated aqueous NaHCO$_3$, dried (Na$_2$SO$_4$), filtered, and concentrated. The residue was then dissolved in CH$_2$Cl$_2$, and treated with trichloroacetonitrile (1.0 mL) and Cs$_2$CO$_3$ (250 mg, 0.77 mmol). After stirring at room temperature for 12 h, the reaction was washed with water, brine, dried (Na$_2$SO$_4$), filtered, and concentrated. A suspension of the tricholoroacetimidate compound, 5-azido-1-pentanol (0.54 g, 4.20 mmol), and 3 Å molecular sieves (1.5 g) in CH$_2$Cl$_2$ (10 mL) was stirred at room temperature for 1 h. The reaction mixture was cooled to 0° C. and treated dropwise with BF$_3$.Et$_2$O (0.11 mL, 0.84 mmol). After stirring at 0° C. for 2 h, saturated aqueous NaHCO$_3$ was added and the reaction mixture was filtered with Celite. The mixture was diluted with CH$_2$Cl$_2$ and then washed with brine. The organic phase was dried over Na$_2$SO$_4$ and evaporated the solvent and purified by chromatography (Hexane:EtOAc=3:1→2:1→1:1) to give S12 as a white foamy solid (210 mg, 24% in three steps). R$_f$: 0.31 (Hexane:EtOAc=1:1). $^1$H NMR (600 MHz, CDCl$_3$): δ 5.12-5.05 (m, 3H), 5.00 (t, J=9.7 Hz, 1H), 4.87-4.79 (m, 3H), 4.48 (dd, J=11.8, 2.0 Hz, 1H), 4.43 (d, J=7.9 Hz, 1H), 4.42 (d, J=7.9 Hz, 1H), 4.38 (d, J=8.0 Hz, 1H), 4.35 (dd, J=12.0, 2.0 Hz, 1H), 4.31 (dd, J=12.5, 4.3 Hz, 1H), 4.07 (dd, J=12.1, 5.2 Hz, 1H), 3.99 (dd, J=12.5, 2.0 Hz, 1H), 3.80-3.74 (m, 1H), 3.71 (dt, J=10.0, 9.5 Hz, 2H), 3.60-3.58 (m, 2H), 3.55-3.52 (m, 2H), 3.45-3.40 (m, 1H), 3.21 (t, J=6.8 Hz, 2H), 2.09 (s, 3H), 2.08 (s, 3H), 2.04 (s, 3H), 1.99 (s, 3H), 1.98 (s, 3H), 1.97 (s, 3H), 1.96 (s, 3H), 1.95 (s, 3H), 1.94 (2xs, 6H), 1.60-1.52 (m, 4H), 1.42-1.33 (m, 2H). $^{13}$C NMR (150 MHz, CDCl$_3$): δ 170.52, 170.31, 170.21, 169.82, 169.79, 169.54, 169.31, 169.10, 100.79, 100.59, 100.55, 76.49, 76.14, 72.87, 72.67, 72.41, 71.75, 71.62, 71.53, 67.72, 62.14, 61.72, 61.48, 51.34, 28.91, 28.50, 23.12, 20.87, 20.68, 20.55, 20.48. HRMS (ESI) Calcd for C$_{43}$H$_{61}$N$_3$O$_{26}$Na$^+$: 1058.3436 [M+Na]$^+$. found: 1058.3419.

[(4,4,5,5,6,6,7,7,8,8,9,9,10,10,11,11,12,12,12-nonadecafluorododecoxycarbonyl-amino)pentyl] 2,3,4,6-tetra-O-acetyl-ß-D-glucopyranosyl-(1→4)-2,3,6-tri-O-acetyl-ß-D-glucopyranosyl-(1→4)-2,3,6-tri-O-acetyl-ß-D-glucopyranoside (S13): Compound S13 was prepared from compound S12 according to the procedure as described for S8 in 55% yields (two steps) after column chromatography (Hexane:EtOAc=1:1→2:3). White solid. R$_f$: 0.41 (Hexane:EtOAc=1:1). $^1$H NMR (600 MHz, CDCl$_3$): δ 5.13-5.06 (m, 3H), 5.01 (t, J=9.7 Hz, 1H), 4.88-4.81 (m, 4H), 4.79 (br, 1H), 4.50 (dd, J=11.8, 1.3 Hz, 1H), 4.44 (d, J=7.2 Hz, 1H), 4.43 (d, J=7.6 Hz, 1H), 4.38 (d, J=8.1 Hz, 1H), 4.36 (dd, J=12.0, 1.8 Hz, 1H), 4.32 (dd, J=12.5, 4.3 Hz, 1H), 410-4.06 (m, 3H), 4.02 (dd, J=12.0, 4.8 Hz, 1H), 3.99 (dd, J=12.4, 2.0 Hz, 1H), 3.79-3.74 (m, 1H), 3.72 (dt, J=11.5, 9.6 Hz, 2H), 3.63-3.58 (m, 1H), 3.56-3.50 (m, 2H), 3.43-3.40 (m, 1H), 3.11 (m, 1H), 2.20-2.10 (m, 2H), 2.10 (s, 3H), 2.09 (s, 3H), 2.05 (s, 3H), 1.99 (s, 3H), 1.98 (2xs, 6H), 1.97 (s, 3H), 1.96 (s, 3H), 1.94 (2xs, 6H), 1.91-1.86 (m, 2H), 1.54-1.52 (m, 2H), 1.48-1.43 (m, 2H), 1.34-1.26 (m, 2H). $^{13}$C NMR (150 MHz, CDCl$_3$): δ 170.53, 170.35, 170.22, 169.81, 169.58, 169.32, 169.11, 153.25, 120.2-108.01 (m, C—F coupling unresolved), 100.79, 100.58, 100.55, 76.47, 76.14, 72.88, 72.70, 72.66, 72.39, 72.00, 71.75, 71.63, 71.54, 71.34, 69.76, 67.69, 63.67, 63.18, 62.13, 61.65, 61.48, 40.84, 29.50, 28.93, 27.99, 27.84, 27.70, 23.02, 20.89, 20.76, 20.67, 20.54, 20.48, 20.34. HRMS (ESI) Calcd for C$_{55}$H$_{68}$F$_{17}$NO$_{28}$Na$^+$: 1536.3656 [M+Na]$^+$. found: 1536.3548.

[(4,4,5,5,6,6,7,7,8,8,9,9,10,10,11,11,12,12,12-nonadecafluorododecoxycarbonyl-amino)pentyl] ß-D-glucopyranosyl-(1→4)-ß-D-glucopyranosyl-(1→4)-ß-D-glucopyranoside (9): Compound 9 was prepared from compound S13 according to the procedure as described for 8 in 50% yields after purification by column chromatography (EtOAc:MeOH=3:1→1:1) and Fluor® Flash® SPE cartridge. White solid. R$_f$: 0.66 (EtOAc:MeOH=3:1). $^1$H NMR (600 MHz, MeOD): δ 4.44 (d, J=8.0 Hz, 1H), 4.39 (d, J=7.8 Hz, 1H), 4.27 (d, J=7.9 Hz, 1H), 4.10 (t, J=6.1 Hz, 1H), 3.91-3.84 (m, 6H), 3.67-3.63 (m, 3H), 3.58-3.48 (m, 7H), 3.39-3.32 (m, 3H), 3.30 (m, 1H), 3.22 (m, 2H), 3.09 (t, J=6.9 Hz, 1H), 2.31-2.26 (m, 2H), 1.97-1.90 (m, 2H), 1.65-1.61 (m, 2H), 1.52-1.48 (m, 2H), 1.43-1.37 (m, 2H). $^{13}$C NMR (150 MHz, MeOD): δ 157.71, 120.11-108.43 (m, C—F coupling unresolved), 103.44, 103.21, 103.05, 79.40, 79.00, 76.95, 76.66, 75.47, 75.25, 75.02, 73.75, 73.48, 70.19, 69.56, 63.07, 61.26, 60.58, 60.30, 40.50, 29.45, 29.20, 27.61, 27.46, 27.32, 23.10, 20.32. HRMS (ESI) Calcd for C$_{35}$H$_{48}$F$_{17}$NO$_{18}$Na$^+$: 1116.2492 [M+Na]$^+$. found: 1116.2520.

[(4,4,5,5,6,6,7,7,8,8,9,9,10,10,11,11,12,12,12-nonadecafluorododecoxycarbonyl-amino)pentyl] ß-D-glucopyranosyl-(1→4)-ß-D-glucopyranosyl-(1→4)-ß-D-glucopyranosyl-(1→4)-13-D-glucopyranoside (10): Compound 10 was prepared from according to the procedure as described for 9 in 86% yields after purification by column chromatography. δ 4.47 (d, J=8.0 Hz, 1H), 4.46 (d, J=8.0 Hz, 1H), 4.42 (d, J=7.8 Hz, 1H), 4.30 (d, J=7.9 Hz, 1H), 4.10 (t, J=6.1 Hz, 2H), 3.91-3.89 (m, 9H), 3.68-3.63 (m, 3H), 3.60-3.50 (m, 14H), 3.39-3.25 (m, 14H), 3.12 (t, J=6.9 Hz, 2H), 2.33-2.26 (m, 2H), 1.96-1.90 (m, 2H), 1.70-1.61 (m, 2H), 1.55-1.52 (m, 2H), 1.43-1.37 (m, 2H). FIRMS (ESI) Calcd for C$_{41}$H$_{58}$F$_{17}$NO$_{23}$Na$^+$: 1255.3128 [M+Na]$^+$. found: 1255.3225.

Mass Spectrometry

The immobilized slide was analyzed with a Bruker Ultraflex MALDI-TOF mass spectrometer equipped with a nitrogen pulsed laser (355 nm). Each data point was collected at the average of 500-1000 shots of the laser beam, and the laser fluence was applied at 40-95%, with the best results obtained mostly at 50-80%. A standard aqueous solution of mannose-NH$_2$ was manually deposited on a defined area of the ACG slide and used to calibrate the data obtained from the immobilized sugars on the same slide substrate. For quantitative comparison of the grafted mannose derivatives at different concentrations, all analyses were made at a single measurement of 500 shots at 80% fluence. The variation in average peak intensity with S/N ratio was plotted.

Protein-Binding Assay

Mannose-protein-binding assay of immobilized mannose with biotinylated ConA and Cy3-tagged streptavidin. The same slide used for MS analysis was washed again with poly-distilled water under mild sonication and then rinsed with PBS (phosphate-buffered saline) buffer. Biotin-labeled ConA (Invitrogen C 21420) was diluted 500-1000 times in PBST buffer (PBS with 0.05% Tween 20). The protein solution (50 mL) was applied to each array substrate and incubated in a Whatman 16-pad incubation chamber. These slides were wrapped with foil and incubated for 1 h in a shaker at room temperature. After the incubation, the slides were washed three times with PB ST buffer. Streptavidin-Cy3 (Sigma S 6402) was diluted in PBS buffer 100 times, and the slides were covered with aluminum foil and incubated again with streptavidin-Cy3 for another hour. After the second incubation, the slides were washed with PBST buffer and distilled water and then purge-dried with high-quality nitrogen gas. The array pattern was analyzed in reflective mode with 540-nm laser light by using the fluorescence light scanner, Array WoRx, made by Applied Precision. The best block on each slide was selected for statistical fluorescence-intensity analysis.

Globo H-protein-binding assay of immobilized Globo H with monoclonal antibody VKg (IgG) from mouse and Cy3-tagged secondary antibody. The Globo H microarray slides were blocked with aqueous ethanolamine (50 mM) to remove the unreacted NHS on the slide surface. The slides were assembled again in the reaction cell and washed with PBS buffer (pH 7.4). Next, a solution of VK9 (1 mL, 50 μg/mL in each cell), the anti-Globo H monoclonal antibody (IgG) from mouse, in PBST (pH 7.4) was added to the cell. The binding experiment was conducted with constant shaking for 1 h. The slide was washed three times (with 10 minutes constant swirling each time) with PBST buffer (pH 7.4). Cy3-tagged goat anti-mouse IgG for VK9 was added to the cell, and the mixture was incubated with shaking in the dark for 1 h. The protein-bound slides were washed five times each with PB ST buffer (pH 7.4), PBS buffer (pH 7.4), and water and then purge-dried with nitrogen gas.

MS-TOF Analysis and Glycan Array Preparation of 4-MS-TOF Analysis of the Poly-Fluorinated Mannose Adsorbed on the PTFE-Like ACG Slides Compound 4 was dissolved in methanol/water (6/4) solvent mixture at approximately 10 mM, 1 mM, 100 uM in series. The solutions (1 μL each) were spotted manually, and also, microarrayed on the slides with the BioDot AD3200 instrument (Agilent Technology) by robotic pin (Array It, SMP4), a deposition of approximately 1.1 nL of the solution per spots of the array. The slides were stored in 30% humidity chamber overnight then analyzed by mass spectroscopy. The blank and poly-fluorinated mannose slides, which contain both silane based and phosphonic acis based ACG slides, were analyzed with Bruker Ultraflex MALDI-TOF mass spectrometer equipped with a nitrogen pulsed laser (355 nm). Equal volume of BSA Trypsin digested (1 pmoel/μL) solution was mixed homogeneously with DHB (dihydroxybenzoic acid, 10 mg in 1:1 acetonitrile/water) solution, and was used as the standard for MS-TOF mass calibration. Each data point was collected at the average of 500 shots of the laser beam, and the laser fluence between 2 to 20% was applied. Most of the experiments were carried out under positive polarized electrical field.

Figure 26A:
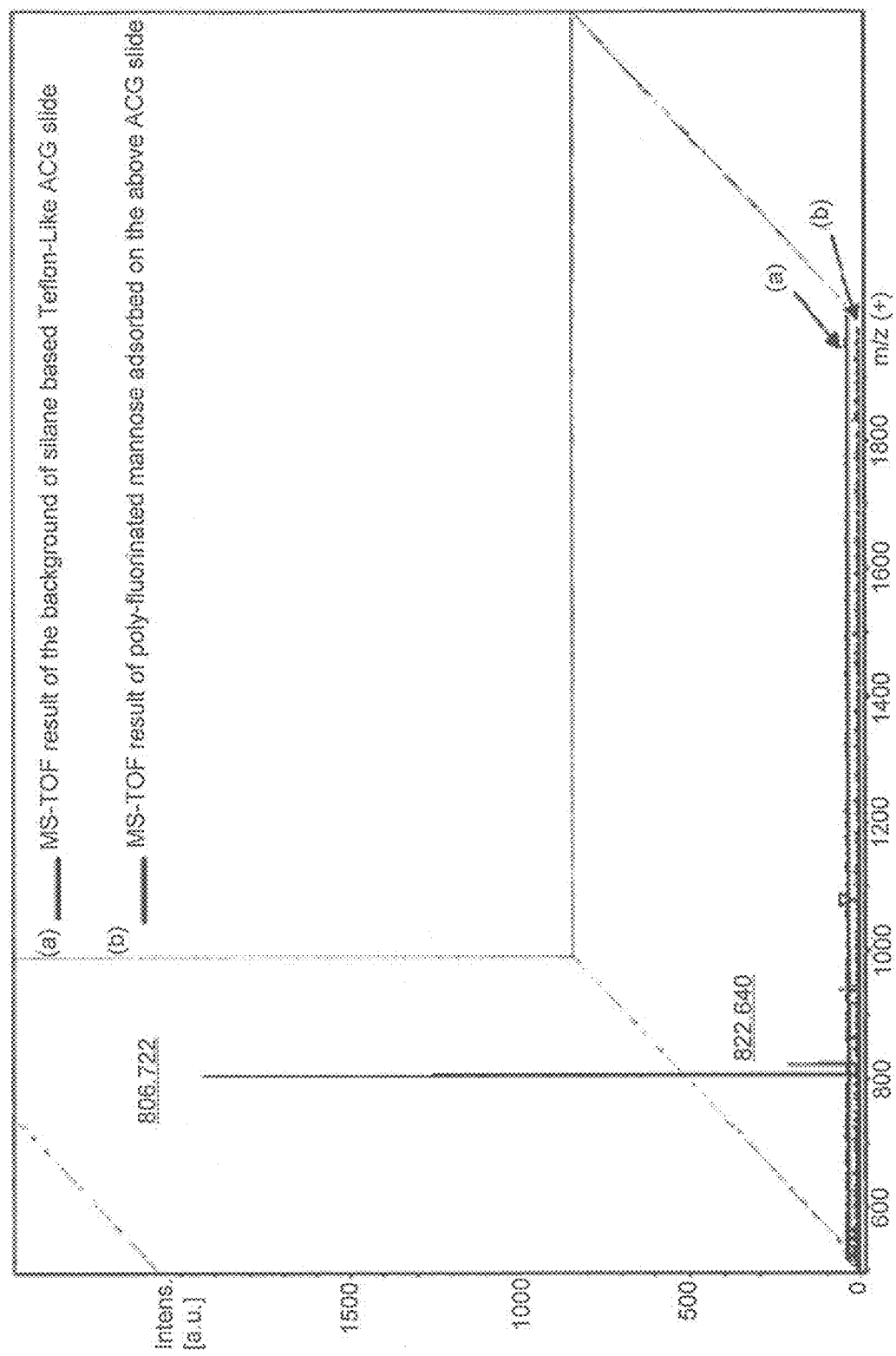
FIG. 26A-FIG. 26B are graphs of implementations of experimental data characterizing silane-based PTFE-like ACG slide by MS-TOF and protein-sugar binding.
Figure 27A:
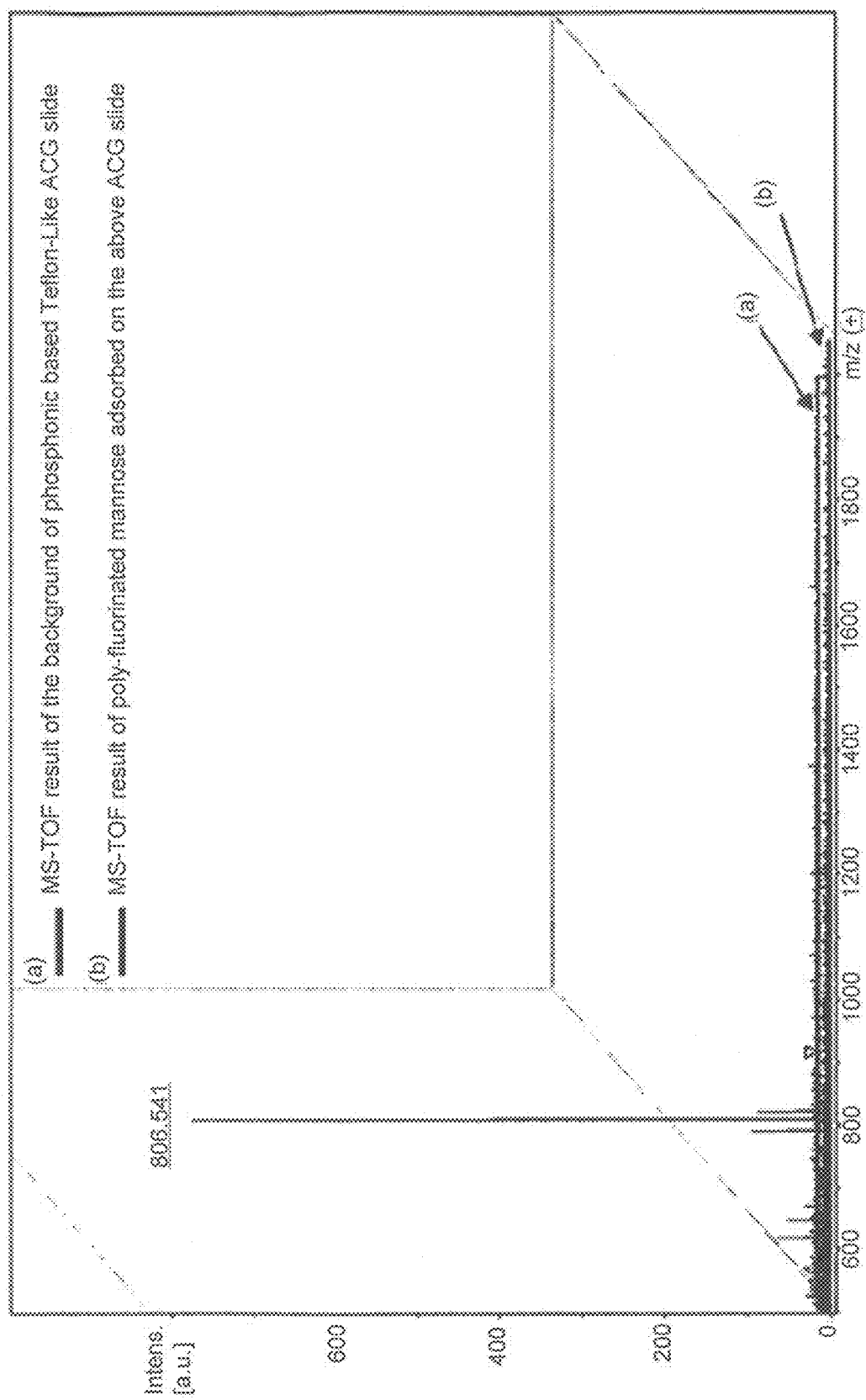
FIG. 27A-FIG. 27B are graphs of implementations of experimental data characterizing phosphonic acid-based PTFE-like ACG slides by MS-TOF and protein-sugar binding.
Figure 28:
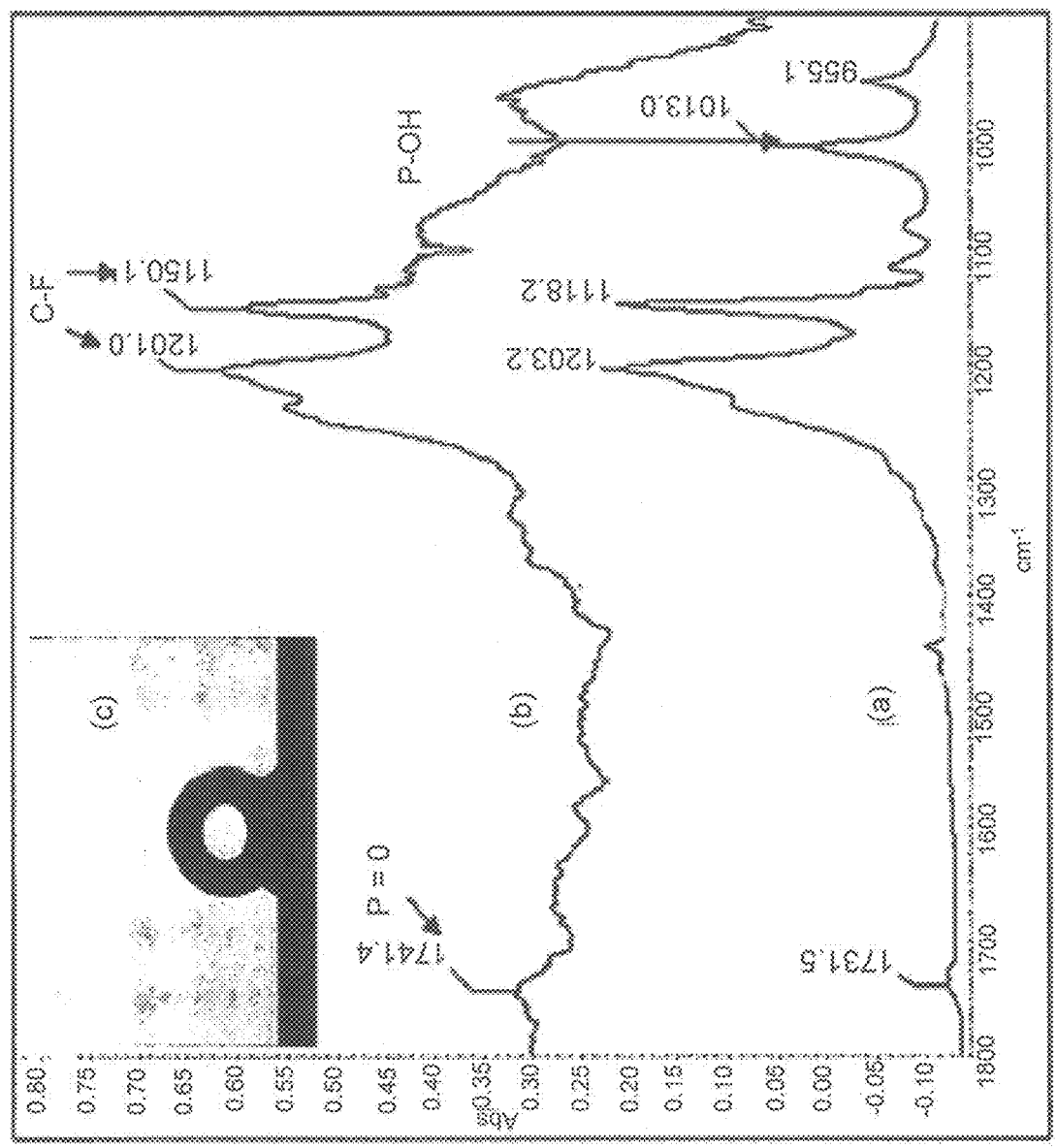
FIG. 28 are graphs of implementations of experimental an FTIR spectrum of Pure Compound 3 (HDFDPA, 3,3,4,4,5, 5,6,6,7,7,8,8,-9,9,10,10,10-heptadecafluorodecylphosphonic acid) and an FTIR spectrum of ACG surface grafted compound 3.

FIG. 26A and FIG. 27A show the MS-TOF background results of these newly fabricated PTFE-like ACG slides. In FIG. 26A, (a) represents an MS-TOF result of the background of silane based PTFE-Like ACG; (b) represents an MS-TOF result of poly-fluorinated mannose adsorbed on the above ACG slide. In FIG. 27A, (a) represents an MS-TOF result of the background of phosphonic acid based PTFE-Like ACG and (b) represents MS-TOF result of poly-fluorinated mannose adsorbed on the above ACG slide. Molecular ions of mannose derivatives (Mw. 783) were observed at 806 [M+Na], and 822 [M+K]$^+$ with very clean baseline since organic chemicals do not adhere to the PTFE-like ACG slide surface.

Figure 26B:
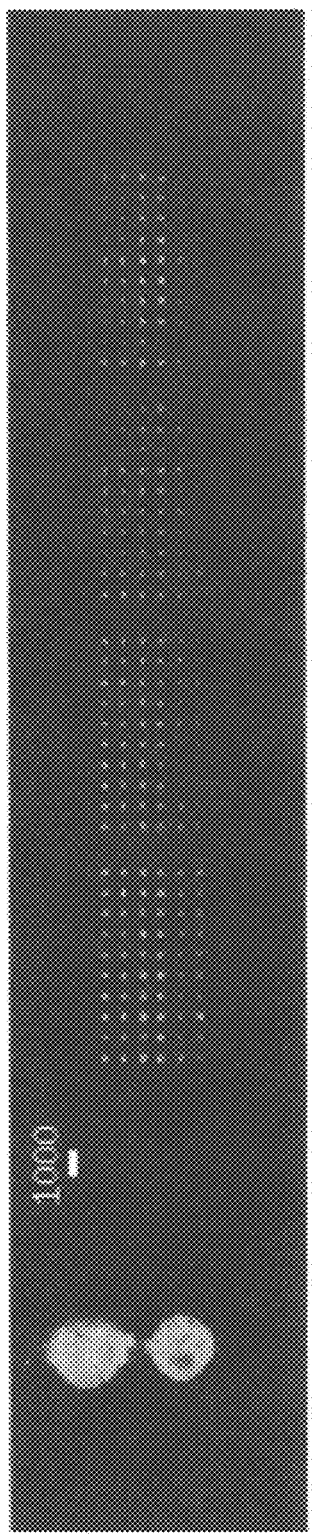
Figure 27B:
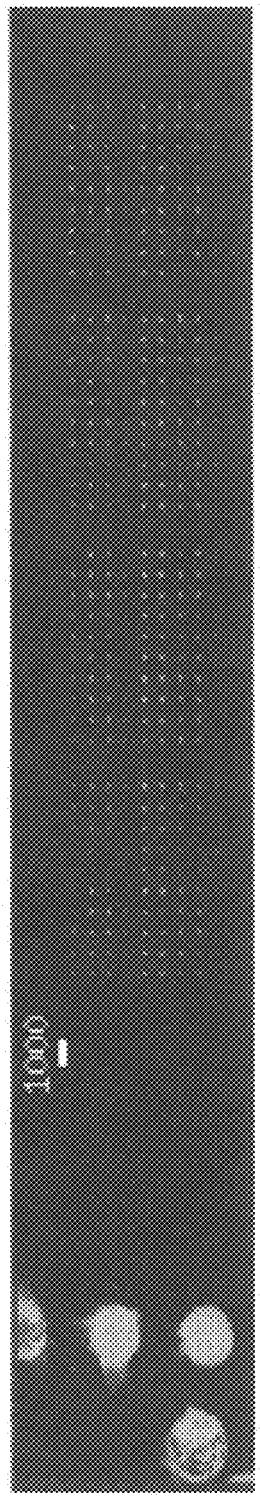

FIG. 26B and FIG. 27B give the results of poly-fluorinated mannose silane based and phosphonic acid based slides. FIG. 26B represents implementations of a microarray of silane based PTFE-like ACG slide. The mannose solutions (1.1 μL/spot) varied in concentration (from 12 mM, 1.2 mM, to 120 μM). Similarly, 27B shows a microarray of a phosphonic acid based PTFE-like ACG slide. The mannose solutions (1.1 μL/spot) varied in concentration (from 14 mM, 1.4 mM, to 140 μM). The fluorescence-tagged Con A-Mannose binding where the mannose derivatives were micro arrayed on the PTFE-like ACG Slide.

Fluorescence-Tagged Con A/Mannose Binding of the Poly-Fluorinated Mannose Adsorbed on the PTFE-Like ACG Slides.

100 μL of Alex 488-tagged Concanavalin A in phosphate-BSA buffer (25 μg/mL, pH 6.5) was applied on the ACG slide surface immobilized with mannose derivative. These slides with Con A solution were incubated at room temperature for approximately 2 hours. After incubation, the slides were washed three times each with 12 ml of Phosphate-BSA buffer, PB ST buffer, and de-ionized water in petri dishes with gentle swirling. Then nitrogen purge dried and analyzed by Array WoRx (Applied Precision) in reflective mode of the fluorescence light scanner at 530 nm. FIG. S1(c) and FIG. S2(c) show the results of these bioassay.

On-Chip Analysis by MALDI-TOF (Ultra-Flex II) (Reaction in Eppendorf)

Cellulase was prepared (5 U/mL in 25 mM pH 5.05 NaOAc buffer solution). Substrate was also dissolved in NaOAc buffer solution (25 mM, pH 5.05) to give 0.5 mM substrate solution. Add 100 uL cellulase solution to 100 uL substrate solution in eppendorf to have a 2.5 U/mL cellulase solution with 0.25 mM substrate. This solution was incubated in 37° C. for 18 hours. Add 100 μL incubated solution onto the slide loaded in FAST® Frame. Put the slide in dry box to remove the water, and then use high vacuum to remove trace water. 100 μL water was used to rinse each well of the FAST® Frame multi-slide plate to solve and remove the salt of the buffer solution. Remove any residual water on the plate by high vacuum and then analyzed the slide by MALDI-TOF Ultra-Flex II.

On-Chip Analysis by MALDI-TOF (Ultra-Flex II) (Reaction on Chip Directly)

Cellulase was prepared (5 U/mL in 25 mM pH 5.05 NaOAc buffer solution). Substrate was also dissolved in NaOAc buffer solution (25 mM, pH 5.05) to give 0.5 mM substrate solution. Add 50 μL cellulase solution to 50 μL substrate solution onto the glass slide which was loaded in FAST® Frame multi-slide plate to have a 2.5 U/mL cellulase solution with 0.25 mM substrate. The well of the plate was sealed and the whole assembly was incubated in 37° C. for 18 hours. Put the slide in dry box to remove the water, and then use high vacuum to remove trace water. 100 uL water was used to rinse each well of the FAST® Frame multi-slide plate to solve and remove the salt of the buffer solution. Remove any residual water on the plate by high vacuum and then analyzed the slide by MALDI-TOF Ultra-Flex II.

Cellulase Purification and MS-TOF Analysis of Cellulase Activity, Cloning, Expression and Purification of Exoglucanase and Endoglucanase The genomic DNA of *Sulfolobus solfataricus* (ATCC 35092) and *Clostridium thermocellum* (ATCC 27405) were obtained from the ATCC biological resource center. The Sso7d (NCBI accession number: AAK42090) gene fragment was amplified directly from the *Sulfolobus solfataricus* genome by polymerase chain reaction (PCR) with forward 5' GGAATFCCATATGGCAACAGTAAAGTFCAAG 3' (SEQ ID NO: 1) and reverse 5' CGGGATCCCTTCTTTTGCTTCTCTAACATTTG 3' (SEQ ID NO: 2) primers. The PCR product encoding Sso7d was digested with NdeI and BamHI and subsequently cloned into expression vector pET-28a (Novagen) to generate pET-28-Sso7d. A two sticky-ends linker, generated by denaturing and annealing with 5' GATCTGATCTGTACGACGATGACGATAAGGGATCTATCGAAGGTCGTG 3' (SEQ ID NO: 3) and 5' GATCCACGACCTFCGATAGATCCCTFATCGTCATCGTCGTACAGATCA 3' (SEQ ID NO: 4) primers, was inserted into the BamHI cleaved pET-28-Sso7d to generate pET-28-Sso7d-Fxa. The functional domains of CtCbhA (NCBI accession number: X80993) gene fragment was amplified directly from the *Clostridium thermocellum* genome by polymerase chain reaction (PCR) with forward 5' GAAGATCTATACTFCCGCAGCCTGATG 3' (SEQ ID NO: 5) and reverse 5' ACGCGTCGACTTAGGTTTCACTGTCTGTGTACTG 3' (SEQ ID NO: 6) primers. The PCR product encoding CtCbhA was digested with BglII and SalI and subsequently cloned into BamHI and SalI cleaved pET-28-Sso7d-Fxa to generate pET-28-Sso7d-Fxa-CtCbhA. The functional domains of CtCel44A (NCBI accession number: D83704) gene fragment was amplified directly from the *Clostridium thermocellum* genome by polymerase chain reaction (PCR) with forward 5' GAAGATCTGAACCTGCAAAAGTGGTFGAC 3' (SEQ ID NO: 7) and reverse 5' ACGCGTCGACTTAGGGCTCCGCAGCTFCAAGCAC 3' (SEQ ID NO: 8) primers.

The PCR product encoding CtCel44A was digested with BglII and SalI and subsequently cloned into BamHI and SalI cleaved pET-28-Sso7d-Fxa to generate pET-28-Sso7d-Fxa-CtCel44A. All DNA constructs were verified by nucleotide sequencing. The correct constructs were transformed into *Escherichia coli* strain BL21 (DE3) competent cell for protein expression. The 10 ml overnight culture of a single transformant was used to inoculate 1 liter of fresh LB medium containing 30 μg/ml kanamycin at 30° C. The incubated temperature was changed to 16° C. until the cells were grown to A600 nm=0.8~1. One hour later isopropyl ß-thiogalactopyranoside (IPTG) was added to a final concentration of 0.5 mM. After 16 h, the cells were harvested by centrifugation at 7,000×g for 15 min to collect the cell paste. The cell pellet was resuspended immediately in the lysis buffer containing 20 mM Tris-HCl, 400 mM NaCl, 10 mM imidazole, pH 7.5. The cell suspension was disrupted by Constant Cell Disruption System (CONSTANT SYSTEM Ltd., UK) and centrifuged at 17,000×g to remove cell debris. The cell-free extract was loaded onto a $Ni^{2+}$–NTA column, which had been previously equilibrated with lysis buffer. The column was washed with lysis buffer, subsequently the His6-tagged protein was eluted by a linear gradient from 10 mM to 300 mM imidazole. The purified His6-tagged Sso7d fusion CtCbhA and CtCel44A proteins were concentrated and changed to stored buffer (50 mM Tris-HCl, 100 mM NaCl, pH 8.0) by 30 kDa cut-off size membrane of Amicon-Ultra-15 (Millipore, Mass., USA) for storage at −80° C.

According to implementations, the devices and methods (e.g., mass spectroscopy) of the present disclosure are operational in an environment comprising numerous general purpose or special purpose computing systems or configurations. Examples of well known computing systems, environments, or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, telephony systems, distributed computing environments that include any of the above systems or devices, and the like.

The devices and methods of the present disclosure may be described in the general context of computer-executable instructions, such as program modules, being executed by a computer. Generally, program modules include routines, programs, objects, components, data structures, etc., that perform particular tasks or implement particular abstract data types. The system may also be practiced in distributed computing environments where tasks are performed by remote processing devices that are linked through a communications network. In a distributed computing environment, program modules may be located in both local and remote computer storage media including memory storage devices. The computer programs are stored in a memory medium or storage medium or they may be provided to a processing unit through a network or I/O bus.

In one aspect, the devices and methods of the present disclosure include at least one central processing unit (CPU) or processor. The CPU can be coupled to a memory, ROM or computer readable media containing the computer-executable instructions. Computer readable media can be any available media that can be accessed by the system and includes both volatile and nonvolatile media, removable and non-removable media implemented in any method or technology for storage of information such as computer readable instructions, data structures, program modules or other data. Computer storage media includes, but is not limited to, RAM, ROM, EEPROM, flash memory, portable memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the fingerprint generation and matching systems. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of any of the above should also be included within the scope of computer readable media. The computer readable media may store instructions or data which implement all or part of the system described herein.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

All publications and patent applications cited in this specification are herein incorporated by reference as if each individual publication or patent application was specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for fabricating an array of carbohydrates immobilized directly on an aluminum oxide surface of a single aluminum-coated glass slide, the method comprising:

(a) immobilizing a plurality of carbohydrates at discrete locations directly and covalently bound to a single underivatized surface of an aluminum-coated glass slide, wherein the single aluminum-coated glass slide is conductive or semi-conductive of an electrical field, wherein the single aluminum-coated glass slide comprises an aluminum oxide surface, and each carbohydrate of the plurality of carbohydrates in the array comprises a phosphonic acid functional group, such that each carbohydrate of the plurality of carbohydrates is a phosphonic acid-derivatized carbohydrate, such that each carbohydrate of the plurality of carbohydrates in the array is immobilized by a covalent bond to said aluminum oxide surface, and wherein the single aluminum-coated glass slide comprises an aluminum oxide layer configured to be in contact with an aluminum layer, which is configured to be in contact with a single glass slide.

2. The method of claim 1, further comprising;

(b) performing a mass spectroscopic (MS) characterization of the array of immobilized carbohydrates on the single aluminum-coated glass slide to identify the presence or absence of binding reactions in the absence of a matrix.

3. The method of claim 1, wherein each carbohydrate of the plurality of carbohydrates is selected from the group consisting of a sugar, a glycoprotein, a glycolipid, and a mannose.

4. The method of claim 1, wherein the phosphonic acid derivatized carbohydrates are immobilized on the surface of the single aluminum-coated glass slide by a covalent interaction between the phosphonic acid group and the aluminum oxide on the surface of the single aluminum-coated glass slide.

5. The method of claim 1, wherein the phosphonic acid-derivatized carbohydrates are immobilized onto the single aluminum-coated glass slide by manual spotting or robotic spotting.

6. The method of claim 2, wherein the MS characterization is matrix-assisted laser desorption-ionization time-of-flight (MS-TOF) characterization.

7. The method of claim 2, wherein the MS characterization is selected from the group consisting of a signal/noise (S/N) ratio that is greater than 22, a laser fluence rate that is less than 10%, and a zero fragmentation of signal.

8. The method of claim 3, wherein each sugar comprises an internal or non-reducing terminal alpha-mannosyl group.

* * * * *

SEQUENCE LISTING

```
<160> NUMBER OF SEQ ID NOS: 8

<210> SEQ ID NO 1
<211> LENGTH: 48
<212> TYPE: DNA
<213> ORGANISM: Artificial Sequence
<220> FEATURE:
<223> OTHER INFORMATION: Linker

<400> SEQUENCE: 1
gatctgatct gtacgacgat gacgataagg gatctatcga aggtcgtg                48

<210> SEQ ID NO 2
<211> LENGTH: 48
<212> TYPE: DNA
<213> ORGANISM: Artificial Sequence
<220> FEATURE:
<223> OTHER INFORMATION: Linker

<400> SEQUENCE: 2
gatccacgac cttcgataga tcccttatcg tcatcgtcgt acagatca                48

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
gaagatctat acttccgcag cctgatg                                       27

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
acgcgtcgac ttaggtttca ctgtctgtgt actg                               34

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gaagatctga acctgcaaaa gtggttgac                                     29

<210> SEQ ID NO 6
<211> LENGTH: 34
<212> TYPE: DNA
<213> ORGANISM: Artificial Sequence
```

```
<220> FEATURE:
<223> OTHER INFORMATION: Primer

<400> SEQUENCE: 6
acgcgtcgac ttagggctcc gcagcttcaa gcac                               34

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
ggaattccat atggcaacag taaagttcaa g                                  31

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
cgggatccct tcttttgctt ctctaacatt tg                                 32
```